(12) United States Patent
George et al.

(10) Patent No.: US 10,010,560 B2
(45) Date of Patent: Jul. 3, 2018

(54) SMALL MOLECULE HSP70 INHIBITORS

(71) Applicants: THE TRUSTEES OF THE UNIVERSITY OF PENNSYLVANIA, Philadelphia, PA (US); THE WISTAR INSTITUTE OF ANATOMY AND BIOLOGY, Philadelphia, PA (US)

(72) Inventors: Donna L. George, Blue Bell, PA (US); Maureen E. Murphy, Glenside, PA (US); Julia I-Ju Leu, Philadelphia, PA (US)

(73) Assignees: The Trustees of the University of Pennsylvania, Philadelphia, PA (US); The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 15/121,345

(22) PCT Filed: Feb. 26, 2015

(86) PCT No.: PCT/US2015/017736
§ 371 (c)(1),
(2) Date: Aug. 24, 2016

(87) PCT Pub. No.: WO2015/130922
PCT Pub. Date: Sep. 3, 2015

(65) Prior Publication Data
US 2017/0014434 A1   Jan. 19, 2017

Related U.S. Application Data

(60) Provisional application No. 61/944,798, filed on Feb. 26, 2014.

(51) Int. Cl.
| | |
|---|---|
| A61K 31/66 | (2006.01) |
| A61K 31/662 | (2006.01) |
| G06F 19/16 | (2011.01) |
| C07F 9/54 | (2006.01) |
| A61K 45/06 | (2006.01) |

(52) U.S. Cl.
CPC ............ *A61K 31/662* (2013.01); *A61K 31/66* (2013.01); *A61K 45/06* (2013.01); *C07F 9/5442* (2013.01); *G06F 19/16* (2013.01)

(58) Field of Classification Search
CPC ............................. A61K 31/662; A61K 31/66
See application file for complete search history.

(56) References Cited

U.S. PATENT DOCUMENTS

| | | |
|---|---|---|
| 5,476,659 A | 12/1995 | Goodman et al. |
| 5,863,938 A | 1/1999 | Martin |
| 2002/0090358 A1 | 7/2002 | Spaner |
| 2004/0024639 A1 | 2/2004 | Goldman |
| 2005/0004211 A1 | 1/2005 | Wu et al. |
| 2008/0193928 A1 | 8/2008 | Castro et al. |
| 2013/0225567 A1 | 8/2013 | Reiser |

FOREIGN PATENT DOCUMENTS

| | | |
|---|---|---|
| DE | 10-2011054972 | 5/2013 |
| JP | 52125146 | 10/1977 |
| WO | WO-2003/032999 | 4/2003 |
| WO | WO-2010/033771 | 3/2010 |
| WO | WO-2012/111017 | 8/2012 |

OTHER PUBLICATIONS

Bestmann, H.J. et atl., "Eine Neue Methode zur Darstellug von Ethinyltriphenyl-phosp honiumsalzen, A New Method for the Preparation of Ethynyltriphenylphisphonium Salts", Chemische Berichte, Jan. 1983, 116: 1320-1326.

Baktharaman, S. et al., "Unprotected Vinyl Aziridines: Facile Synthesis and Cascade Transformations", Organic Letters, Nov. 2009, 12(2): 240-243.

Bestmann, H.J, et al., "Einfache Synthese von (Arylethiny)triphenylphosphonium-Salzen", Angewandte Chemie, Jan. 1977, 89(1): 55.

Balaburski, G.M. et al., "A Modified HSP70 Inhibitor Shows Broad Activity as an Anticancer Agent", Molecular Cancer Research, Jan. 2013, 11(3): 219-229.

(Continued)

*Primary Examiner* — Sahar Javanmard
(74) *Attorney, Agent, or Firm* — Howson & Howson LLP

(57) ABSTRACT

In an effort to discover therapies for treating HSP70 related diseases, a previously unidentified hydrophobic pocket was found in the C-terminal domain of DnaK and of human HSP70. A novel chemical scaffold was also discovered for identifying compounds that treat diseases related to this hydrophobic pocket. The compounds have the structure of the formula (I), wherein L, M, and $R^1$-$R^5$ are defined herein and are, therefore, in these therapies, optionally with other pharmaceutical agents such as genotoxic agents. Accordingly these compounds are useful in inhibiting HSP70 or DnaK, reducing HSP70 in mitochondria of a cancer cell, treating malignant neoplastic disease, or inhibiting or reducing bacterial growth. These compounds also resulted in novel methods of screening for a HSP70 inhibitor or DnaK inhibitor by using the three-dimensional structure of the hydrophobic pocket in DnaK or HSP70.

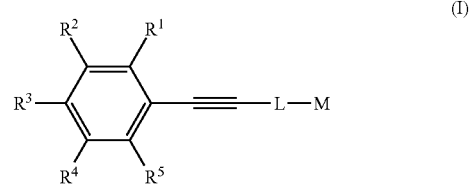

(I)

6 Claims, 14 Drawing Sheets

(56) References Cited

OTHER PUBLICATIONS

Figures 1A, 1B, 1C, 1D, 1E, 1F, 1G:
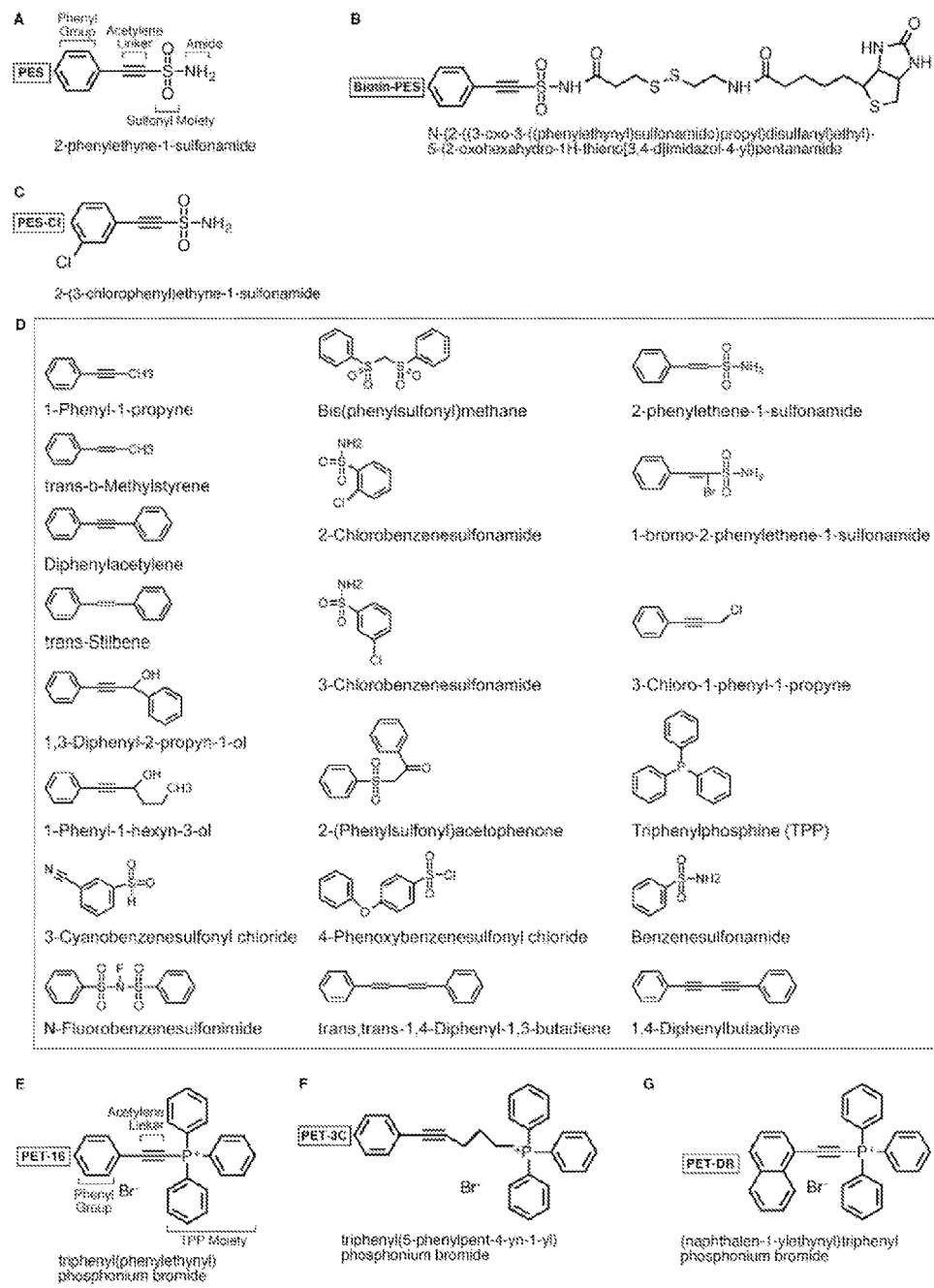

Zahn, M. et al., "Structural Studies on the Forward and Reverse Binding Modes of Peptides to the Chaperone DnaK", Journal of Molecular Biology, Apr. 2013, 425(14): 2463-2479.
Leu, J.I. et al., "Structural Basis for the Inhibition of HSP70 and DnaK Chaperones by Small-Molecule Targeting of a C-Terminal Allosteric Pocket", ACS Chemical Biology, Nov. 2014, 9(11): 2508-2516.
Stang, P.J. et al., "A Simple High-Yield Preparation of Alkynylphosphonium Triflates", Journal of Organic Chemistry, Feb. 1992, 57: 4305-4306.
International Search Report dated Aug. 28, 2015 in corresponding International Patent Application No. PCT/US2015/017736, filed Feb. 26, 2015.
Written Opinion dated Aug. 28, 2015 in corresponding International Patent Application No. PCT/US2015/017736, filed Feb. 26, 2015.
U.S. Appl. No. 14/048,540, filed Mar. 27, 2014, Fox Chase Cancer Center and The Trustees of the University of Pennsylvania.
U.S. Appl. No. 13/051,511, filed Aug. 4, 2011, The Trustees of the University of Pennsylvania.
Adams, P. D. et al., PHENIX: a comprehensive Python-based system for macromolecular structure solution, Acta Crystallogr D Biol Crystallogr, Jan. 2010, D66:213-221.
Afonine, P. V. et al., Towards automated crystallographic structure refinement with phenix.refine, Acta Crystallogr D Biol Crystallogr, Mar. 2012, D68:352-367.
Bertelsen, E. B. et al., Solution conformation of wild-type *E. coli* Hsp70 (DnaK) chaperone complexed with ADP and substrate, PNAS, May 2009, 106(21):8471-8476.
Chang, L. et al., Chemical screens against a reconstituted multiprotein complex: myricetin blocks DnaJ regulation of DnaK through an allosteric mechanism, Chem Biol, Feb. 2011, 18(2):2010-221.
Daugaard, M. et al., The heat shock protein 70 family: highly homologous proteins with overlapping and distinct functions, FEBS Letters, Jul. 2007, 581(19):3702-3710.
Iki, T. et al., In vitro assembly of plant RNA-induced silencing complexes facilitated by molecular chaperone HSP90, Molecular Cell, Jul. 2010, 39(2):282-291.
Iwasaki, S. et al., Hsc70/Hsp90 chaperone machinery mediates ATP-dependent RISC loading of small RNA duplexes, Molecular Cell, Jul. 2010, 39(2):292-299.
Kityk, R. et al., Structure and dynamics of the ATP-bound open conformation of Hsp70 chaperones, Molecular Cell, Dec. 2012, 48(6):863-874.
Leu, J. I. J. et al., A small molecule inhibitor of inducible heat shock protein 70, Molecular Cell, Oct. 2009, 36(1):15-27.
Leu, J. I. J. et al., HSP70 inhibition by the small-molecule 2-phenylethynesulfonamide impairs protein clearance pathways in tumor cells, Mol Cancer Res, Jul. 2011, 9(7):936-947.
Liu, B. et al., Co-translational response to proteotoxic stress by elongation pausing of ribosomes, Mol Cell, Feb. 2013, 49(3):453-463.
Mayer, M. P. and Bukau, B., Hsp70 chaperones: cellular functions and molecular mechanism, Cellular and Molecular Life Sciences, Mar. 2005, 62(6):670-684.
McCoy, A. J. at el., Phaser crystallographic software, Journal of Applied Crystallography, Aug. 2007, 40(4):658-674.
Millard, M. et al., Preclinical evaluation of novel triphenylphosphonium salts with broad-spectrum activity, PLoS ONE, Oct. 2010, 5(10):e13131.
Murphy, M. E., The HSP70 family and cancer, Carcinogenesis, May 2013, 34(6):1181-1188.
Nylandsted, J. et al., Heat shock protein 70 promotes cell survival by inhibiting lysosomal membrane permeabilization, The Journal of Experimental Medicine, Aug. 2004, 200(4):425-435.
Patury, S. et al., Pharmacological targeting of the Hsp70 chaperone, Curr Top Med Chem, Nov. 2009, 9(15):1337-1351.
Powers, M. V. et al., Targeting HSP70: the second potentially druggable heat shock protein and molecular chaperone?, Cell Cycle, Apr. 2010, 9(8):1542-1550.
Qi, R. et al., Allosteric opening of the polypeptide-binding site when an Hsp70 binds ATP, Nat Struct Mol Biol, Jul. 2013, 20(7):900-907.
Rérole, A. L. et al., Peptides and aptamers targeting HSP70: a novel approach for anticancer chemotherapy, Cancer Research, Jan. 2011, 71(2):484-495.
Rodina, A. et al., Identification of an Allosteric Pocket on Human Hsp70 Reveals a Mode of Inhibition of This Therapeutically Important Protein, Chem Biol, Dec. 2013, 20(12):1469-1480.
Rousaki, A. et al,. Allosteric drugs: the interaction of antitumor compound MKT-077 with human Hsp70 chaperones, J. Mol Biol, Aug. 2011, 411(3):614-632.
Ryhänen, T. et al., Crosstalk between Hsp70 molecular chaperone, lysosomes and proteasomes in autophagy-mediated proteolysis in human retinal pigment epithelial cells, J. Cell Mol Med, Sep. 2009, 13(9B):3616-3631.
Schlecht, R. et al., Functional analysis of hsp70 inhibitors, PLoS ONE, Nov. 2013, 8(11):e78443.
Swain, J. F. et al., Hsp70 chaperone ligands control domain association via an allosteric mechanism mediated by the interdomain linker, Mol Cell, Apr. 2007, 26(1):27-39.
Zhuravleva, A. et al., An interdomain energetic tug-of-war creates the allosterically active state in Hsp70 molecular chaperones, Cell, Dec. 2012, 151(6):1296-1307.
Moulin, M. et al., Sensitization of chronic lymphocytic leukemia cells to TRAIL-induced apoptosis by hyperthermia, Cancer Letters, May 2007, 250(1):117-127.
Hasegawa, K. et al., 'The photobromination of beta-styrenesulfonamides and syntheses of 2-arylacetylene-l-sulfonamides, Bulletin of the Chemical Society of Japan, Sep. 1977, 50(9):2346-2350.
Leu, J. I. J. et al., Structural Basis for the Inhibition of HSP70 and DnaK Chaperones by Small-Molecule Targeting of a C-Terminal Allosteric Pocket, ACS Chemical Biology, Aug. 2014, 9(11):2508-2516.
Patani, G. A. and Edmond, J. L. V., Bioisosterism: A Rational Approach in Drug Design, Chem. Rev., May 1996, 96(8):3147-3176.
Tanaka, Y. and Miller. S. I., Synthesis and nucleophilic properties of 4-aryl-5-triphenylphosphonium-1,2,3-triazole ylides or 4-aryl-1,2,3-triazol-5-yltriphenylphosphoranes, J. Org. Chem., Jul. 1973, 38(15):2708-2712.
Kwak, P. K. and Tomari, Y., The N domain of argonaute drives duplex unwinding during RISC assembly, Nature Structural & Molecular Biology, Feb. 2012, 19(2):145-151.
Morishima, Y. et al., Heme-dependent activation of neuronal nitric oxide synthase by cytosol is due to an Hsp70-dependent, thioredoxin-mediated thiol-disulfide interchange in the heme/substrate binding cleft, Biochemistry, Jul. 2011, 50(33):7146-7156.
Pellecchia, M. et al., Structural insights into substrate binding by the molecular chaperone DnaK, Nature Structure Biology, Apr. 2000, 7(4):298-303.
Wang, H. et al., NMR solution structure of the 21 kDa chaperone protein DnaK substrate binding domain: a preview of chaperone-protein interaction, Biochemistry, May 1998, 37(22):7929-7940.
Zhu, X. et al., Structural analysis of substrate binding by the molecular chaperone DnaK, Science Jun. 1996, 272(5268):1606-1614.
Kettern, N. et al., Chaperone-assisted degradation: multiple paths to destruction, Biol. Chem., May 2010, 391:481-489.
Steele, A. J. et al., 2-Phenylacetylenesulfonamide Upregulates Noxa and Induces p-53 Independent Apoptosis of CLL Cells, Blood (ASH Annual Meeting Abstracts), Nov. 2007, 110(11):Abstract.
Notice to File Missing Parts of Nonprovisional Application dated Apr. 5, 2011 in related U.S. Appl. No. 13/051,511, filed Mar. 18, 2011.
Response dated Apr. 12, 2011 in related U.S. Appl. No. 13/051,511, filed Mar. 18, 2011.
Restriction Requirement dated Sep. 17, 2012 in related U.S. Appl. No. 13/051,511, filed Mar. 18, 2011.

(56) References Cited

OTHER PUBLICATIONS

Response dated Oct. 17, 2012 in related U.S. Appl. No. 13/051,511, filed Mar. 18, 2011.
Office Action dated Nov. 20, 2012 in related U.S. Appl. No. 13/051,511, filed Mar. 18, 2011.
Response dated Feb. 20, 2013 in related U.S. Appl. No. 13/051,511, filed Mar. 18, 2011.
Office Action dated Apr. 9, 2013 in related U.S. Appl. No. 13/051,511, filed Mar. 18, 2011.
Notice to File Corrected Application Papers dated Oct. 31, 2013 in related U.S. Appl. No. 14/048,540, filed Oct. 8, 2013.
Response dated Nov. 26, 2013 in related U.S. Appl. No. 14/048,540, filed Oct. 8, 2013.
Restriction Requirement dated Nov. 18, 2014 in related U.S. Appl. No. 14/048,540, filed Oct. 8, 2013.
Response dated Jan. 16, 2015 in related U.S. Appl. No. 14/048,540, filed Oct. 8, 2013.
Office Action dated May 5, 2015 in related U.S. Appl. No. 14/048,540, filed Oct. 8, 2013.
Response dated Sep. 2, 2015 in related U.S. Appl. No. 14/048,540, filed Oct. 8, 2013.
International Preliminary Report on Patentability dated Sep. 9, 2016 in corresponding International Patent Application No. PCT/US2015/017736, filed Feb. 26, 2015.
Brodsky et al. (2006) Hsp70 molecular chaperones: emerging roles in human disease and identification of small molecule modulators. Curr. Top. Med. Chem. 6, 1215-1225.
Kim et al. (2013) Molecular chaperone functions in protein folding and proteostasis. Ann. Rev. Biochem. 82, 323-355. (Jun. 2013).
Mayer (2013) Hsp70 chaperone dynamics and molecular mechanism. Trends Biochem. Sci. 38,507-514. (Epub Sep. 5, 2013).
Smith et al. (2011) Mitochondria-targeted small molecule therapeutics and probes. Antioxid. Redox Signal 15, 3021-3038. (Epub Jun. 6, 2011).

Note: PES-Cl does not synergize with Vemurafenib (not shown).

DnaK (aa 389-607) with PET-16

DnaK (aa 389-607) with PET-16

DnaK (aa 389-607) with PET-16

HSP70 (aa 386-616) with PET-16

SMALL MOLECULE HSP70 INHIBITORS

CROSS-REFERENCE TO RELATED APPLICATIONS

This application is a national stage of International Patent Application No. PCT/US2015/017736, filed Feb. 26, 2015, which claims the benefit of the priority of US Provisional Patent Application No. 61/944,798, filed Feb. 26, 2014, which applications are incorporated herein by reference.

This invention was made with government support under Grant Nos. R01 CA118761 and P01 CA114046 awarded by the National Institutes of Health. The government has certain rights in the invention.

Applicant hereby incorporates by reference the Sequence Listing material filed in electronic form herewith. This filed is labeled "UPN-14-7001PCT_sequence_ST25.txt".

BACKGROUND

Maintaining effective protein homeostasis, or proteostasis, is critical to the survival of all cells, and it protects against disease. Misfolded or unstructured proteins are functionally impaired; they have the potential to cause formation of potentially toxic aggregates. Critical components in cellular proteostasis networks are the mammalian stress-inducible heat shock protein-70 (HSP70, also called HSPA1A, HSP72) and its evolutionarily conserved bacterial ortholog, DnaK. These proteins coordinate key processes needed to maintain protein quality control, especially under conditions of enhanced stress; their activities include protein folding, protein transport across membranes, formation/dissolution of protein-protein interactions, and preventing accumulation of toxic protein aggregates. Thus, these molecular chaperones protect against the deleterious consequences of elevated physiologic and environmental stresses that cause conformational changes in polypeptides and disrupt protein function.

Altered protein quality control is characteristic of many human diseases. Cancer cells, for example, are subject to an enhanced stress environment that promotes protein misfolding; thus, these aberrant cells are especially dependent on the activities of HSP70 to maintain proteostasis. Indeed, HSP70 is considered a cancer-critical survival protein, and it is constitutively expressed at elevated levels in most cancers. This contrasts with its typically modest expression in unstressed normal cells; this has led to the testable suggestion that HSP70 inhibitors should exhibit a therapeutic index that can be exploited for preferential killing of cancer cells. Elevated HSP70 expression confers protection against a variety of stresses, such as hypoxia, altered metabolism and exposure to chemotherapeutic agents. It also inhibits apoptosis and oncogene-induced senescence, and is a major contributor to poor therapeutic outcome in patients. Reducing HSP70 abundance in cancer cells using RNA interference, antisense approaches, or peptides promotes apoptosis and cell cycle arrest, and increases sensitization to chemotherapeutic agents. In mammalian cells, the actions of HSP70 also coordinate with autophagy and proteasome pathways to aid in the disposal and recycling of altered proteins and organelles, and to prevent the accumulation of misfolded, or otherwise unwanted, proteins. Enhanced levels of autophagy are induced by different forms of stress, and promote the survival of established cancers. An impairment of HSP70 would be predicted to disrupt critical pathways of autophagy and the proteasome, particularly in tumor cells. HSP70 is a multifunctional HSP70 protein and a critical co-chaperone for the molecular chaperone HSP90. Working together, these chaperones direct the stability, localization and activity of a large and varied group of client proteins, many of which have been implicated in promoting tumorigenesis. A number of these client proteins have been implicated in the development and/or progression of cellular transformation; they include proteins involved in signal transduction, cell proliferation, or energy production. Examples of these proteins include AKT, BRAF(V600E) and EGFR, among others.

While HSP90 inhibitors are known, one of the consequences of HSP90 inhibition is a robust upregulation of HSP70, likely reducing the overall anti-tumor efficacy of HSP90 inhibitors. Because HSP70 is an obligate co-chaperone for HSP90, but also has independent pro-survival functions in tumor cells, targeting HSP70 has the potential to simultaneously impair multiple signaling- and protein quality control-networks. This strategy offers unique advantages for developing an effective and durable therapy for cancer treatment, even in genetically heterogeneous tumor cells.

Protein misfolding and aggregation contribute to cellular toxicity in disorders such as cystic fibrosis and certain neurodegenerative diseases, and increases in HSP70 expression can modulate this phenotype. Thus, HSP70 and DnaK have emerged as attractive targets for the development of new treatments for cancers and other human disorders, as well as to address the growing need for alternative antimicrobial agents. However, despite a great deal of interest in the translational potential of these chaperones, remarkably few selective, effective modulators have been identified.

HSP70 and DnaK are part of an evolutionarily conserved family of 70 kDa heat shock proteins that have a similar overall structure: they consist of an approximately 44 kDa N-terminal nucleotide binding domain (NBD), a conserved flexible middle linker, and the approximately 25 kDa C-terminal substrate/peptide binding domain (SBD). Each major domain is composed of several highly dynamic subdomains. HSP70 and DnaK exhibit about 45-50% amino acid similarity. These molecular chaperones transiently and dynamically interact with a very large and diverse array of substrates, or clients, by binding exposed hydrophobic regions of partially folded or unfolded proteins. When ADP is bound to the NBD, the substrate binds with high affinity; ATP binding favors substrate release. Allosteric coupling involves cycles of nucleotide binding and hydrolysis, together with the binding and release of substrate.

Many previous chemical screens for HSP70 inhibitors have tended to focus on the N-terminal ATP-binding site (or surrounding regions), partly because this approach was successful in identifying inhibitors of the HSP90 molecular chaperone as well as many protein kinases. However, the ATP-binding site of HSP70 has been less amenable to this strategy. While there is great interest in targeting HSP70 and DnaK for therapeutic use, there are very few selective or well-characterized compounds that directly interact with these proteins to modulate function. Further, there are no drugs in clinical trials that directly bind HSP70. 2-Phenylethynesulfonamide (referred to as PES, FIG. 1A), a biotinylated PES analog (referred to as B-PES, FIG. 1B) and a chlorinated derivative, 2-(3-chlorophenyl) ethynesulfonamide (PES-Cl, FIG. 1C) were previously identified as selective inhibitors of HSP70/DnaK. See, e.g., International Patent Application Publication No. WO2010/033771, published Mar. 25, 2010 and US Patent Application Publication No. US2011/0189125.

SUMMARY OF THE INVENTION

In one aspect, a compound of formula (I) is provided and has the following structure or a pharmaceutically acceptable salt, prodrug, solvate, or metabolite thereof, wherein L, M, and $R^1$-$R^5$ are defined herein. In one embodiment, when (i) L is absent, (ii) M is $PPh_3$ or $PPh_2CH_3$ and (iii) the compound is a bromide salt, optionally not all of $R^1$ to $R^5$ are H.

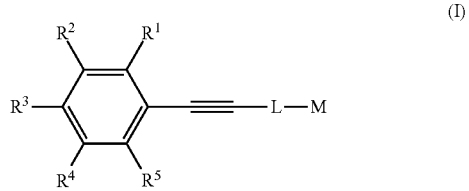

In one embodiment, the compound of formula (I) is the following, wherein X is acetate, adipate, alginate, ammonium, ascorbate, aspartate, benzenesulfonate, benzoate, bicarbonate, bisulfate, borate, bromide, bromide chloride, butyrate, camsylate, camphorate, camphorsulfonate, caproate, chloride, citrate, dibromide, dichloride, digluconate, ethylenediamine, fluoride, formate, fumarate, gluconate, glutamate, glutarate, glycerolphosphate, halogen, 2-hydroxyethansulfonate, hemisulfate, heptanoate, hexanoate, iodide, lactate, laurate, maleate, malonate, malate, maleate, mesylate, myristyl methanesulfonate, mesitylenesulfonate, naphthylenesulfonate, napsylate, nicotinate, nitrate, oleate, oxalate, oxalate, palmitate, pamoate, pectinate, persulfate, 3-phenylpropionate, phosphate, picrate, pivalate, propionate, pyruvate, saccharinate, sebacate, stearate, succinate, sulfate, sulfonate, tartrate, tetrafluoroborate, trifluoromethyl sulfonate, tosylate, trichloroacetate, trifluoroacetate, p-toluenesulfonate, undecanoate, valerate, or xinafoate.

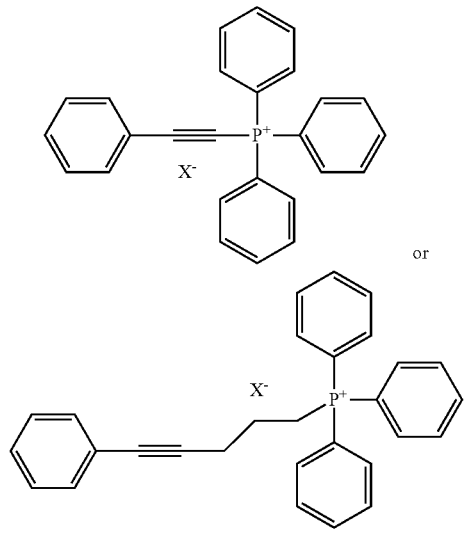

In another aspect, composition is provided and contains (i) a compound of formula (I) and (ii) a genotoxic agent. In one embodiment, the genotoxic agent is a chemotherapeutic. In another embodiment, the genotoxic agent is radiation. In a further embodiment, the genotoxic agent is an HSP90 inhibitor. In yet another embodiment, the genotoxic agent is a BRAF inhibitor. In still another embodiment, the genotoxic agent is a growth factor receptor inhibitor. In a further embodiment, the genotoxic agent is an immune checkpoint blockade inhibitor. In another embodiment, the genotoxic agent is a proteasome inhibitor.

In a further aspect, a method of inhibiting heat shock protein (HSP) 70 or DnaK is provided and includes administering a compound which co-crystallizes with HSP70 or DnaK to a subject in need thereof.

In still another aspect, a method of reducing HSP70 in mitochondria of a cancer cell is provided and includes administering a compound which co-crystallizes with HSP70 or DnaK to a subject in need thereof.

In yet a further aspect, a method of treating malignant neoplastic disease is provided and includes administering a compound that co-crystallizes with HSP70 or DnaK to a subject in need thereof. In one embodiment, the malignant neoplastic disease is epithelial cancer, Merkel cell carcinoma, liver cancer, cervical cancer, anal cancer, penile cancer, vulvar cancer, vaginal cancer, breast cancer, ovarian cancer, uterine cancer, skin cancer, melanoma, oral cancer, colon cancer, neck cancer, head cancer, eye cancer, Kaposi's sarcoma, leukemia, nasopharyngeal carcinoma, mesothelioma, bone cancer, brain cancer, prostate cancer, testicular cancer, pancreatic cancer, hepatocellular carcinoma, lung cancer, or lymphoma.

In another aspect, a method of inhibiting or reducing bacterial growth is provided and includes administering a compound which co-crystallizes with HSP70 or DnaK to a subject in need thereof.

In still a further aspect, a method for screening for a HSP70 inhibitor or DnaK inhibitor is provided and includes (a) determining the three-dimensional structure of a complex containing a HSP70 inhibitor and DnaK by X-ray diffraction to produce atomic coordinates; (b) constructing a three dimensional model of the complex utilizing the atomic coordinates or portions thereof; and (c) comparing the three dimensional model with a three dimensional model for a $HIS_6$-IEGR-DnaK-PET-16 (referred to here as DnaK-PET-16) complex, wherein the DnaK-PET-16 complex contains a hydrophobic pocket and the HSP70 inhibitor binds in the hydrophobic pocket in the three-dimensional structure of the complex.

In yet another aspect, a method for inhibiting HSP70, wherein HSP70 contains a hydrophobic pocket formed by residues in strand β1, strand β7, loop LL,1, and loop Lα,β of the substrate-binding domain β of human HSP70, is provided and includes contacting the hydrophobic pocket with a ligand which binds to strand β1, strand β7, loop LL,1, and loop Lα,β of the substrate-binding domain β of human HSP70 of the hydrophobic pocket.

In a further aspect, a computer for producing a three-dimensional representation of a DnaK-HSP70 inhibitor complex is provided and includes (a) a computer-readable data storage medium containing a data storage material encoded with computer-readable data, wherein the data includes (i) the structure coordinates of a $HIS_6$-IEGR-DnaK-PET-16 (referred to here as DnaK-PET-16) crystal and (ii) the structure coordinates of a crystal of the DnaK-HSP70 inhibitor; (b) a working memory for storing instructions for processing the computer-readable data; (c) a central-processing unit coupled to the working memory and to the computer-readable data storage medium for processing the computer-machine readable data into the three-dimensional representation; and (d) a display coupled to the central-processing unit for displaying the three-dimensional representation.

In another aspect, a machine-readable data storage medium is provided and contains a data storage material encoded with machine readable data, wherein the data is defined by at least a portion of the structure coordinates of the HIS$_6$-IEGR-DnaK-PET-16 (referred to here as DnaK-PET-16) in Table 1.

In still a further aspect, a three-dimensional structure of a hydrophobic pocket in HSP70 is provided. The hydrophobic pocket includes (i) strand β1 including L401 of SEQ ID NO: 2; (ii) strand β7 including G484 of SEQ ID NO: 2; (iii) loop LL,1 including one or both of L394 or P398 of SEQ ID NO: 2; and (iv) loop Lα,β including one or both of N505 or D506 of SEQ ID NO: 2.

In yet another aspect, a three-dimensional structure of a hydrophobic pocket in DnaK is provided. The hydrophobic pocket includes (i) strand β1 including L399 of SEQ ID NO: 4; (ii) loop LL,1 including one or both of L392 or P396 of SEQ ID NO: 4; (iii) loop L6,7 including G482 of SEQ ID NO: 4; and (iv) loop Lα,β containing one or both of A503 and S504 of SEQ ID NO: 4.

Other aspects and advantages of the invention will be readily apparent from the following detailed description of the invention.

DETAILED DESCRIPTION OF THE DRAWINGS

FIGS. 1A to 1G provide the PET-16 and analogs thereof. FIGS. 1A-1C provide the chemical structures of PES, Biotin-PES, and PES-Cl, respectively. The chemical names and the major functional groups are indicated. FIG. 1D identifies the compounds containing one or more moieties in common with PES/PES-Cl that exhibited no detectable cytotoxic effect on tumor cells when tested at concentrations of 200 μM. The chemical names are indicated. FIGS. 1E-1G are the chemical structures of PET-16, PET-3C and PET-DR, respectively. The chemical names and the major functional groups are indicated.

Figures 2A, 2B, 2C, 2D:
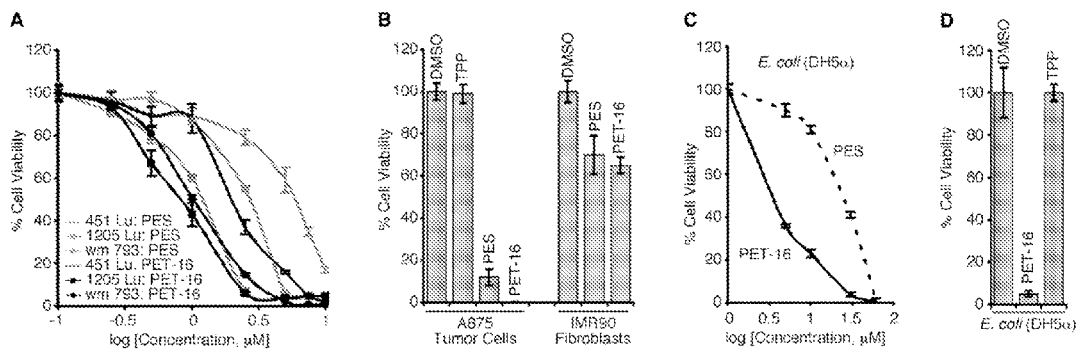

FIGS. 2A-2D illustrate the cytotoxicity of PET-16 to human tumor cells and its inhibition on *E. coli* growth. FIG. 2A is a line graph with data obtained from MTT assays of human melanoma cell lines treated with the indicated concentrations of PES or PET-16 for 72 h. The corresponding cell survival is normalized to vehicle (DMSO) treatment. Average and standard deviation (s.d.) from three independent experiments are shown. FIG. 2B are bar graphs of human melanoma (A875) cells and nontransformed human (IMR90) fibroblasts that were treated with DMSO, 10 μM PES or 10 μM PET-16 for 24 h. The data are representative of four independent experiments, and shows that PET-16 is preferentially cytotoxic for tumor cells. FIG. 2C is a line graph illustrating the growth of *E. coli* DH5α treated with different concentrations of PES or PET-16 for 6 h at 43° C. Error bars represent the s.d. of four independent experiments. FIG. 2D is a bar graph illustrating the growth of *E. coli* DH5α treated with DMSO, 30 μM PET-16 or 30 μM TPP for 6 h at 43° C. Error bars represent the s.d. of four independent experiments.

Figures 3A, 3B, 3C, 3D, 3E, 3F, 3G, 3H, 3I, 3J, 3K, 3L:
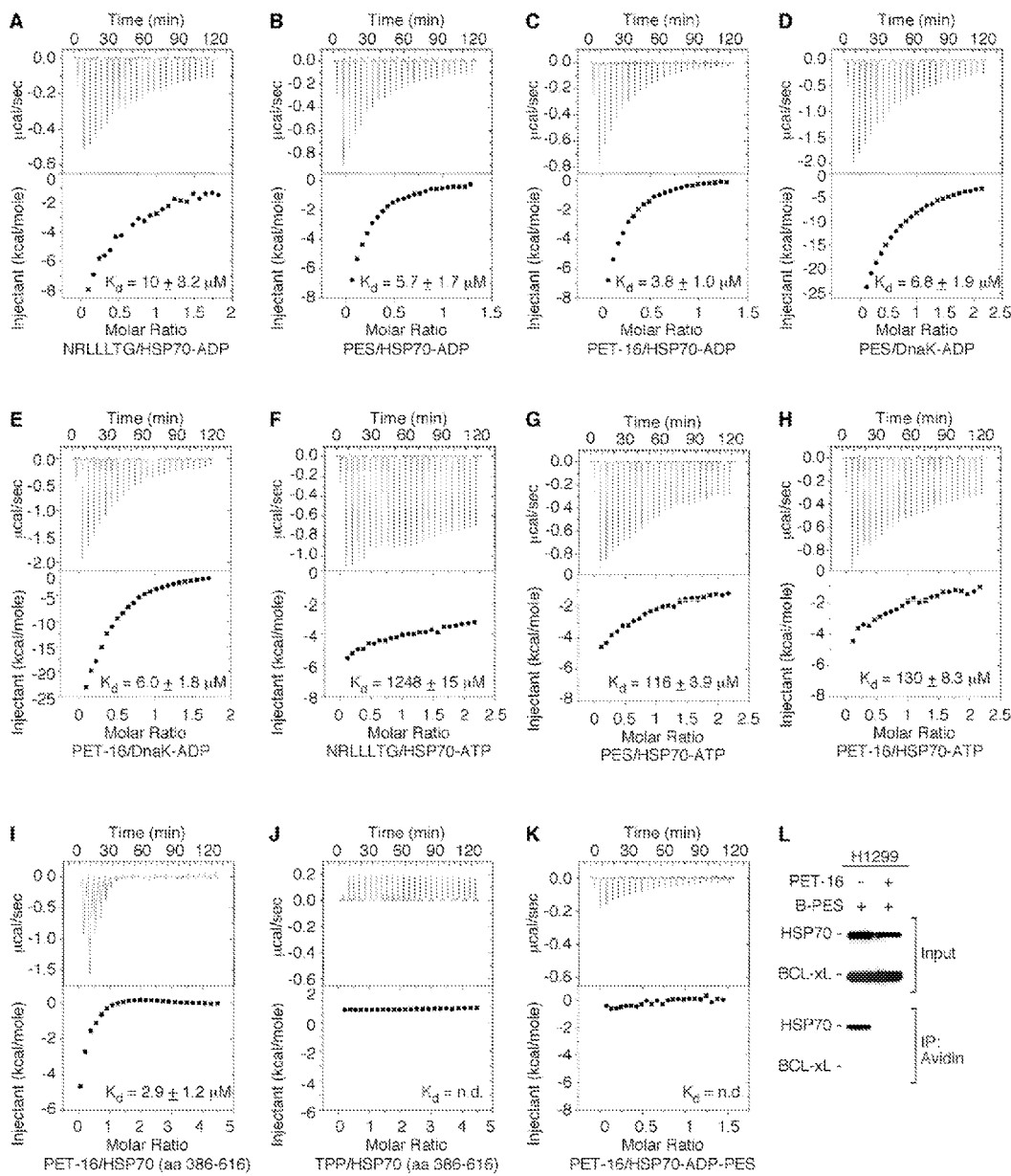

FIGS. 3A-3L illustrate that PET-16 binds directly to ADP-bound HSP70 and DnaK. Specifically, FIGS. 3A-3H are isothermal calorimetric titration (ITC) assays of the indicated compounds (NRLLLTG—SEQ ID NO: 7, PES or PET-16) with purified HSP70-ADP, DnaK-ADP or HSP70-ATP proteins. The data are representative of three independent experiments. FIGS. 3I and 3J are ITC assays for the interaction between HSP70 (aa 386-616 of SEQ ID NO: 2) protein and PET-16 (I) or TPP (J). Binding constants ($K_d$ values) are shown (average and s.d. from three independent experiments). PET-16 also binds directly to the purified, full-length, nucleotide-free HSP70 protein, with a reported dissociation constant of 5.2+/−0.1 micromolar, which is the average and standard deviation from two independent experiments (data not shown). FIG. 3K is ITC assay of HSP70 protein preincubated with ADP and PES for 1 h. The mixture was titrated into the sample cell containing PET-16. The data are representative of three independent ITC experiments. FIG. 3L are western blots of human lung carcinoma (H1299) cells that were pretreated with DMSO or excess (8×) PET-16 for 1 h prior to the addition of 20 μM B-PES for 5 h and examined for the expression of HSP70 or BCL-xL. B-PES-containing complexes were captured by Avidin resins and immunoblotted either with anti-HSP70 or anti-BCL-xL antibody. PET-16 inhibited subsequent interaction of HSP70 with B-PES.

Figures 4A, 4B, 4C, 4D, 4E, 4F, 4G, 4H, 4I, 4J, 4K, 4L:
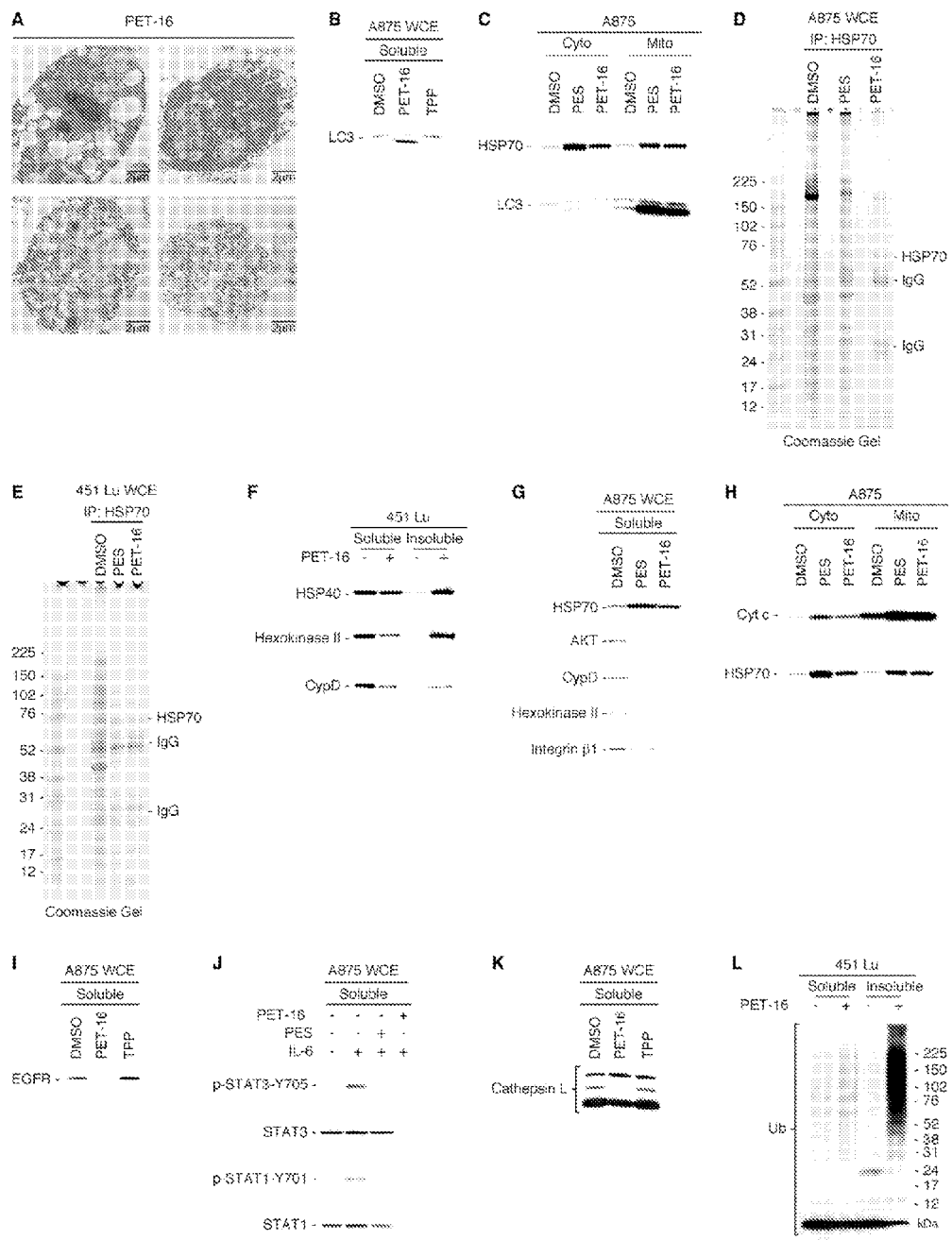

FIGS. 4A-4L illustrate that PET-16 impairs proteostasis. FIG. 4A is an EM analysis which shows altered autophagy in PET-16 treated tumor cells, with formation of autophagosomes, accumulation of vacuoles, and the appearance of granular and aggregated masses. There is a general absence of obvious nuclei in PET-16 treated tumor cells. FIGS. 4B and 4C are western blots (WB) which reveal a marked increase in the abundance of the autophagy indicator LC3 in total soluble (B) and mitochondrial fractions (C) of A875 melanoma cell line. FIGS. 4D and 4E are gels of whole-cell extracts (WCE) prepared from human melanoma A875 (D) or 451 Lu (E) cells treated with DMSO, PES or PET-16 that were immunoprecipitated using an anti-HSP70 antibody. The excised band of about 70 kDa shown in the Coomassie gel is HSP70, as confirmed by liquid chromatography—tandem mass spectrometry analysis. FIGS. 4F-4I are western blots of cell lines were treated with DMSO, PES or PET-16 for 24 h and immunoblotted for the indicated proteins. FIG. 4J are western blots of indicated melanomas pretreated with DMSO, PES or PET-16, followed by treatment with IL-6. Cell extracts were immunoblotted for the proteins indicated. Inhibition of IL-6 induced STAT3 and STAT1 phosphorylation by PET-16. FIG. 4K is a western blot analysis indicating altered processing of cathepsin L from the larger precursor form to the smaller mature form in the indicated cells following PET-16 treatment for 24 h. FIG. 4L is a western blot of the human melanoma 451 Lu cells treated with DMSO, PES or PET-16 for 24 h. Cells were harvested in 1% NP40-containing lysis buffer, fractionated into detergent-soluble and detergent-insoluble preparations, and assayed by western blot for ubiquitin.

Figures 5A, 5B, 5C, 5D, 5E, 5F:
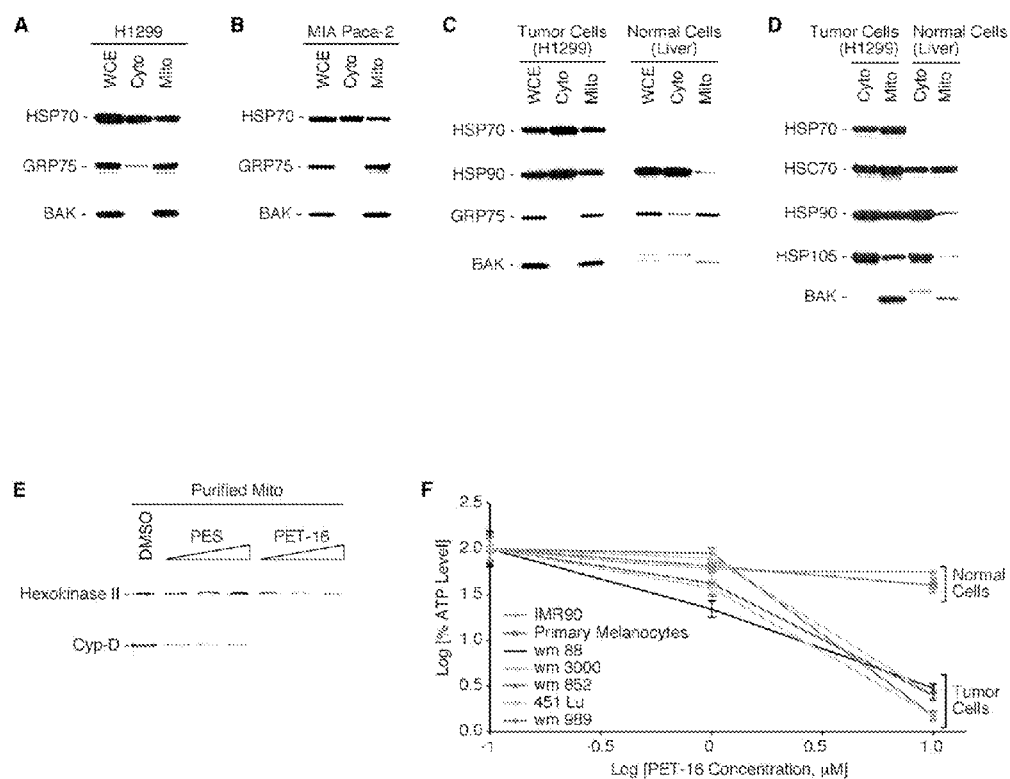

FIGS. 5A-5F illustrates that PET-16 leads to loss of mitochondrial protein Cyclophilin D and impairs bioenergetics in tumor cells. FIGS. 5A-5D are western blots of HSP70, which is present at mitochondria of tumor H1299 cells but not in normal tissue, such as liver. The constitutively expressed 70 kDa family members, HSC70 and GRP75, are present in mitochondria of normal cells. Equal amounts of whole cell (WC)-, cytosolic (cyto)-, and mitochondrial (mito)-extracts prepared from cell lines H1299 (A, C) and MIA PaCa-2 (B) or normal (liver) cells (C, D) were examined by western blot analysis for the presence of the proteins indicated. Generally, only the lower molecular weight, leaderless form of BAK is found in the mitochondria of tumor and normal cells; a higher molecular weight, unprocessed form of BAK, is the form present in cytosolic and whole cell extracts prepared from the mouse liver. FIG. 5E is a western blot of purified mitochondria from human lung carcinoma H1299 cells treated with DMSO, PES or PET-16. Mitochondrial (mito)-extracts prepared and examined by western blot analysis for the presence of the indicated proteins. PET-16 significantly reduced the abundance of Cyp-D in the soluble-protein fraction, consistent with functional inactivation. FIG. 5F is a line graph of total cellular ATP levels using the AlamarBlue® assay, an indicator of mitochondrial metabolic activity, particularly of the mitochondrial electron chain. Decreases of AlamarBlue® fluorescence, indicative of mitochondrial damage, are noted in PET-16-treated tumor cells (melanoma tumor cell line WM88 (-), melanoma tumor cell line WM3000 (x), melanoma tumor cell line WM852 (*), human melanoma 451 Lu cells (●), and melanoma tumor cell line WM989 (|), but not normal cells (nontransformed human fibroblasts (IMR90-♦) and primary melanocytes (■)). Values are normalized to the vehicle-treated cells. Error bars represent standard deviation (s.d.) of four independent experiments.

Figure 6:
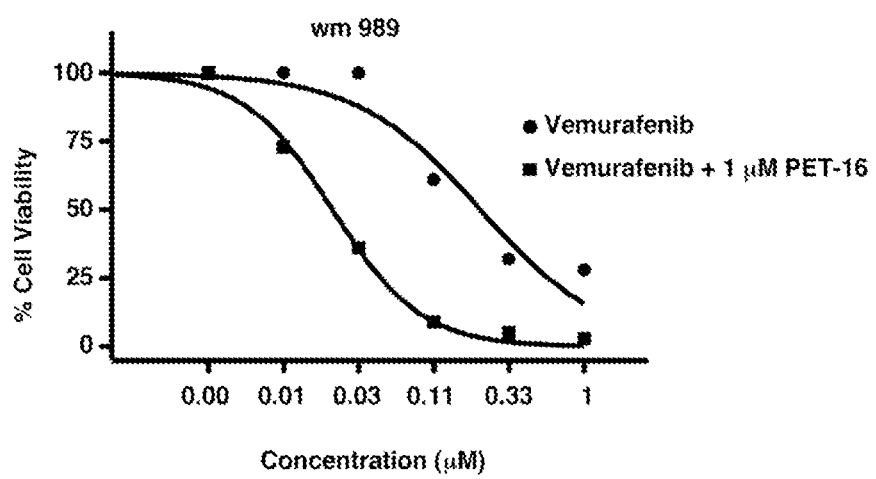

FIG. 6 is a line graph illustrating that PET-16 synergizes with the BRAF inhibitor Vemurafenib to reduce the viability of the melanoma tumor cell line WM989 (■). WM989 cells treated singularly with Vemurafenib are depicted by (●). No synergy was detected between Vemurafenib and PES-Cl.

Figures 7A, 7B, 7C:
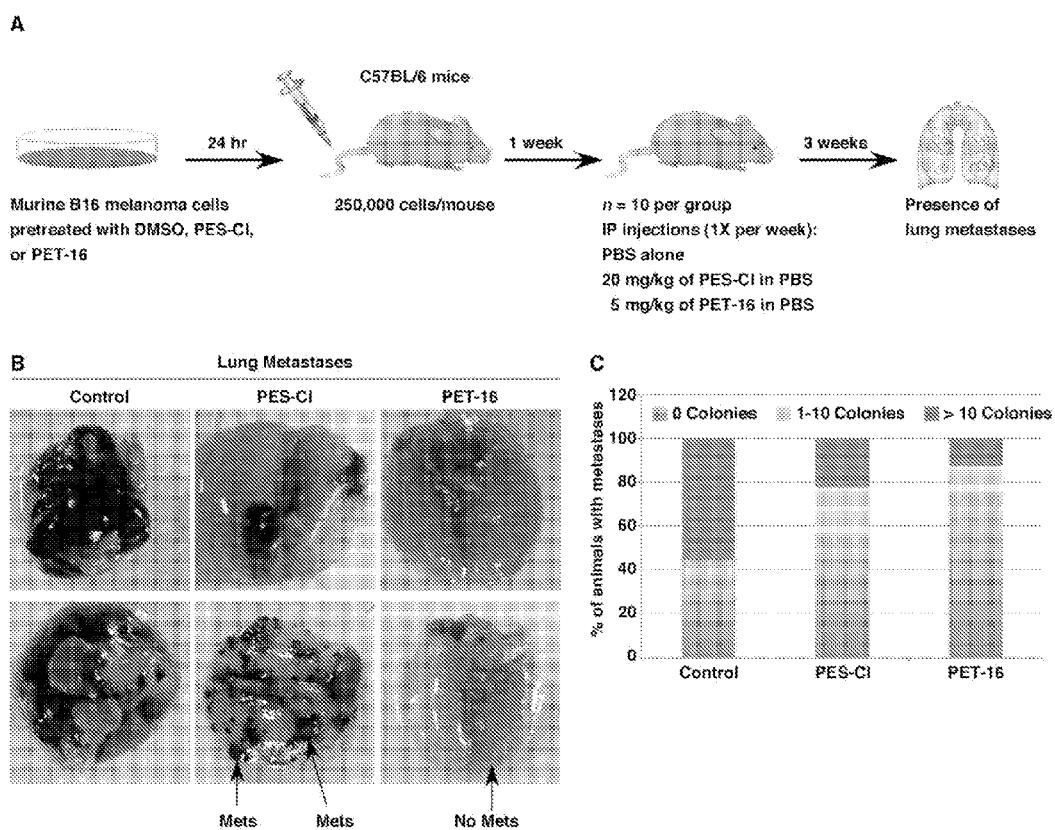

FIGS. 7A-7C illustrate that PET-16 impairs metastasis in a mouse model of melanoma. A well-recognized pulmonary metastatic model was utilized in which immunocompetent, wild-type C57BL/6 mice were injected with the highly metastatic mouse melanoma cell line B16, as indicated. The results of the experiment provide evidence that PET-16 is able to significantly impair the appearance of lung metastases. FIG. 7A is a summary of the steps entailed in the model. FIG. 7B are photographs of biopsied lungs obtained from the infected mice. FIG. 7C provides a graphical representation of counts of metastatic colonies intermediate gray square represents 0 colonies, lightest gray square represents 1-10 colonies and darkest gray square represents >10 colonies) seen in lungs of vehicle-, PES-Cl- or PET-16-treated mice.

Figure 8A:
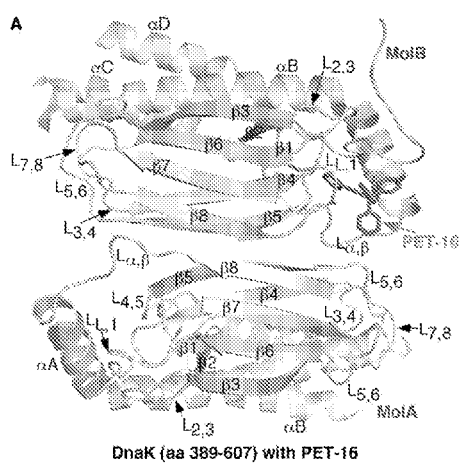
Figure 8B:
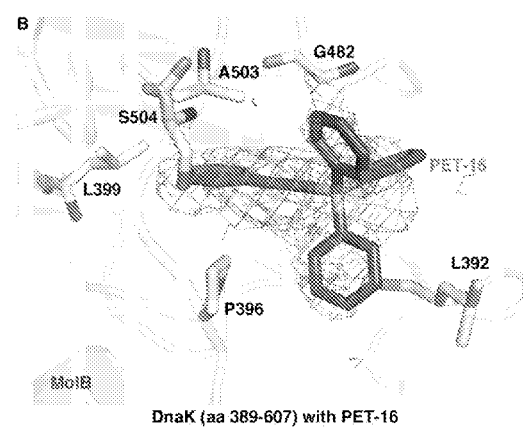
Figure 8C:
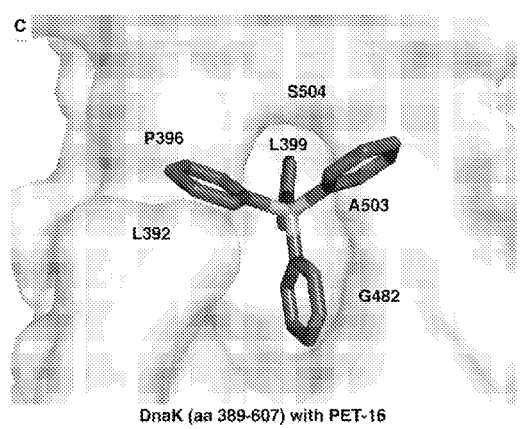
Figure 8D:
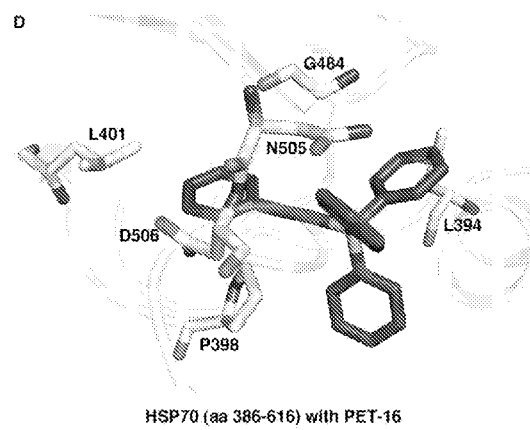

FIGS. 8A-8D provide the X-ray crystal structure of the $HIS_6$-IEGR-DnaK-PET-16 (referred to here as DnaK-PET-16) complex. FIG. 8A is the overall structure of the DnaK-PET-16 complex. The major domains and secondary structural elements are labeled, e.g., PET-16, in MolB. This figure can also be seen as FIG. 3A in Leu, J I et al, 2014 ACS Chem. Biol. 9:2508-2516, incorporated by reference herein. FIG. 8B is an electron density map corresponding to PET-16 of the DnaK-PET-16 cocrystal structure. The map is contoured at 3.0 σ from a simulated annealing $F_o$-$F_c$ omit map of the refined structure without any contribution from the PET-16 inhibitor model. $F_o$-$F_c$ difference map proximal to the PET-16 binding site of MolB following protein refinement prior to introducing the PET-16 model contoured at 3.0 σ is shown. The $2F_o$-$F_c$ electron density map of the refined structure corresponding to PET-16 contoured at 1.0 σ is shown. Key PET-16 contacting residues are in stick format and labeled. The PET-16 compound is in a stick model in blue and binds to a hydrophobic pocket formed by strand β1 (L399) and loops LL,1 (L392, P396), L6,7 (G482) and Lα,β (A503 and S504) in the C-terminus of DnaK. Note also that this additional electron density in MolB of the DnaK-PET-16 complex was modeled as PET-16, with the electron-rich phosphine in the region of greatest electron density and the phenyl group and acetylene linker pointing into the hydrophobic pocket and the TPP pointing out towards solvent, which was consistent with additional rounds of crystallographic refinement. This figure can also be seen as FIG. 3B in Leu, J I et al, 2014 cited above. FIG. 8C provides the hydrophobic pocket for PET-16 in the DnaK-PET-16 structure. Key residues of the PET-16-binding hydrophobic pocket in DnaK-SBD are highlighted and labeled. FIG. 8D provides the alignment of PET-16 from (C), modeled into the X-ray structure of the substrate-bound HSP70 complex. PET-16 is a stick model. Key residues of HSP70 around the PET-16 inhibitor are highlighted and labeled. Note that PET-16 binds to a hydrophobic cleft flanked by residues located on strands β1 (L401) and β7 (G484) and loops LL,1 (L394 and P398) and Lα,β (N505 and D506) of the SBDβ subdomain of the human stress-inducible HSP70. Note also that the phenyl group and acetylene linker of the PET-16 compound is pointing into the hydrophobic pocket and the TPP is pointing out towards solvent. See also, FIGS. 3B to 3F of Leu, JI et al, 2014 cited above, which depict the electron density map corresponding to MolB of the DnaK-PET-16 cocrystal structure. (B) Electron density map corresponding to PET-16 in the DnaK-PET-16 co-crystal structure. The $2F_o$-$F_c$ electron density map of the refined structure corresponding to PET-16 contoured at 1.0 σ is shown in blue. The $F_o$-$F_c$ difference map prior to introducing PET-16 into the model is contoured at 3.0 σ and shown in green, there is no contribution from PET-16 in this map. $F_o$ -$F_c$ PET-16 omit map contoured at 3.0 σ is shown in red. Side chain of key PET-16 contacting residues and Gly482 are shown in stick format and labeled. The PET-16 compound is shown as a stick model in gray. Note that PET-16 binds to a pocket formed by strand β1 (L399) and loops LL,1 (L392, P396), L6,7 (G482) and Lα,β (A503 and S504). (C) Electron density map corresponding to MolA of the DnaK-PET-16 co-crystal structure. The $F_o$-$F_c$ map, corresponding to the PET-16 binding site in MolB, contoured at 3.0 σ, is shown in green. The $2F_o$-$F_c$ electron density map of strand β1 (L399) and loops LL,1 (L392, P396), L6,7 (G482) and Lα,β (A503 and S504) in MolA contoured at 1.5 σ is shown in blue. Key PET-16 contacting residues are shown in yellow stick format and labeled. The electron density corresponding to PET-16, as noted in FIG. 3B, was not observed in the refined structure of MolA. (D) Structural alignment of MolA with MolB. The PET-16 compound is shown in red stick format and labeled. (E and F) Structural alignment of MolA with MolB. Structural differences noted in strand β1 and loops LL,1 and Lα,β of MolA and MolB are illustrated in that cited document, incorporated herein by reference.

Figures 9A, 9B, 9C, 9D, 9E, 9F, 9G, 9H:
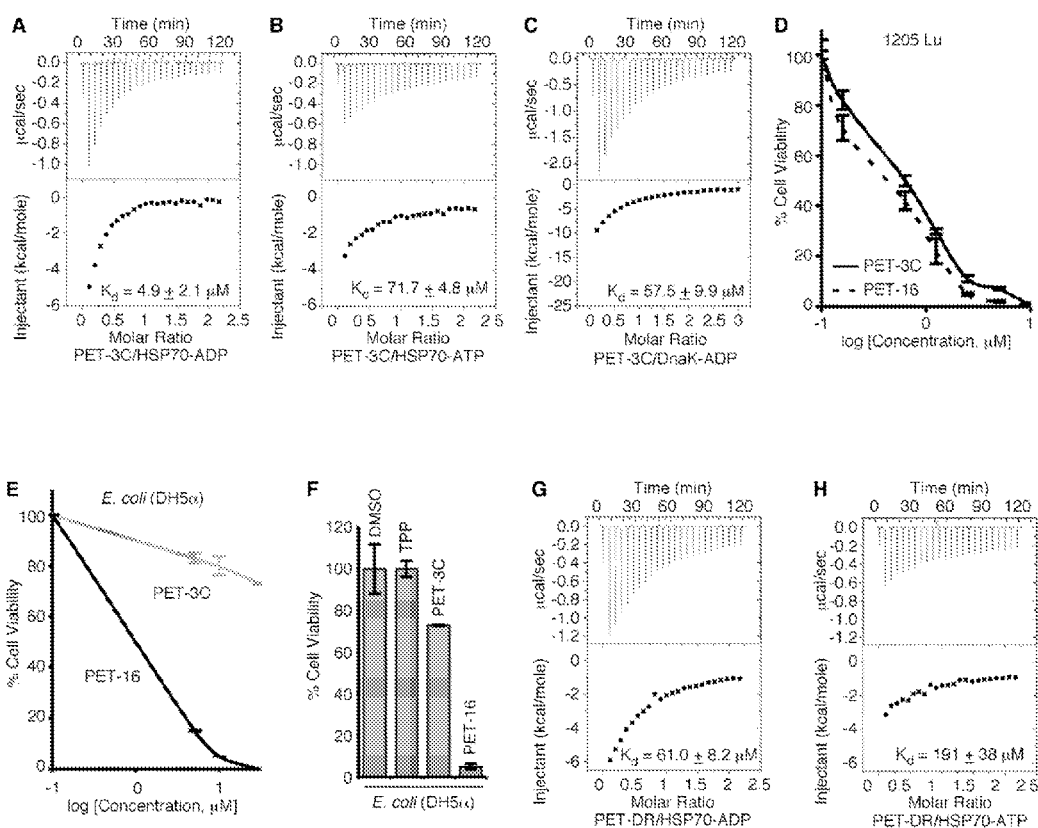

FIGS. 9A-9H illustrate that PET-16 binds directly to ADP-bound HSP70 and is cytotoxic to human tumor cells. FIGS. 9A-9C are ITC assays of the interaction of PET-3C with purified human HSP70-ADP (A), human HSP70-ATP (B) and DnaK-ADP (C) proteins. The data are representative of three independent experiments. FIG. 9D is a line graph of an MTT assay of the human melanoma cell line 1205 Lu treated with the indicated concentrations of PET-16 (---) or PET-3C (-) for 72 h. The corresponding cell survival is normalized to the DMSO-treatment. Average and standard deviation (s.d.) from three independent experiments are shown. FIG. 9E is a line graph illustrating the growth of *E. coli* DH5α strain treated with different concentrations of PET-16 (black) or PET-3C (gray) for 6 h at 43° C. Error bars represent the s.d. of four independent experiments. FIG. 9F is a bar graph illustrating the growth of *E. coli* DH5α treated with DMSO, 30 μM PET-16, 30 μM PET-3C or 30 μM TPP for 6 h at 43° C. Error bars represent the s.d. of four independent experiments. FIGS. 9G and 9H are ITC measurement of the interaction of PET-DR with purified human HSP70-ADP (G) and human HSP70-ATP (H) proteins. The data are representative of three independent experiments.

Figure 10:
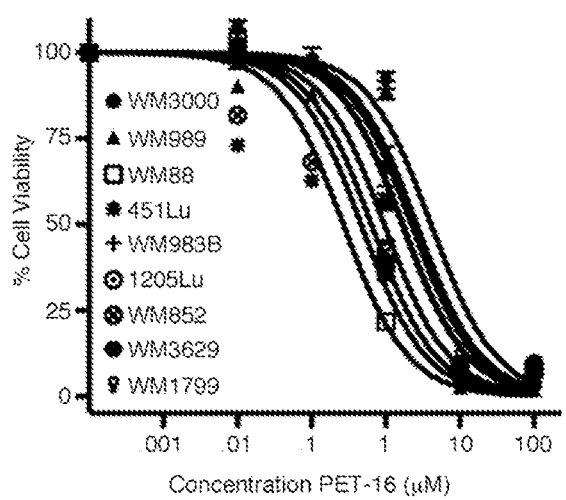
Figures 11A, 11B, 11C, 11D:
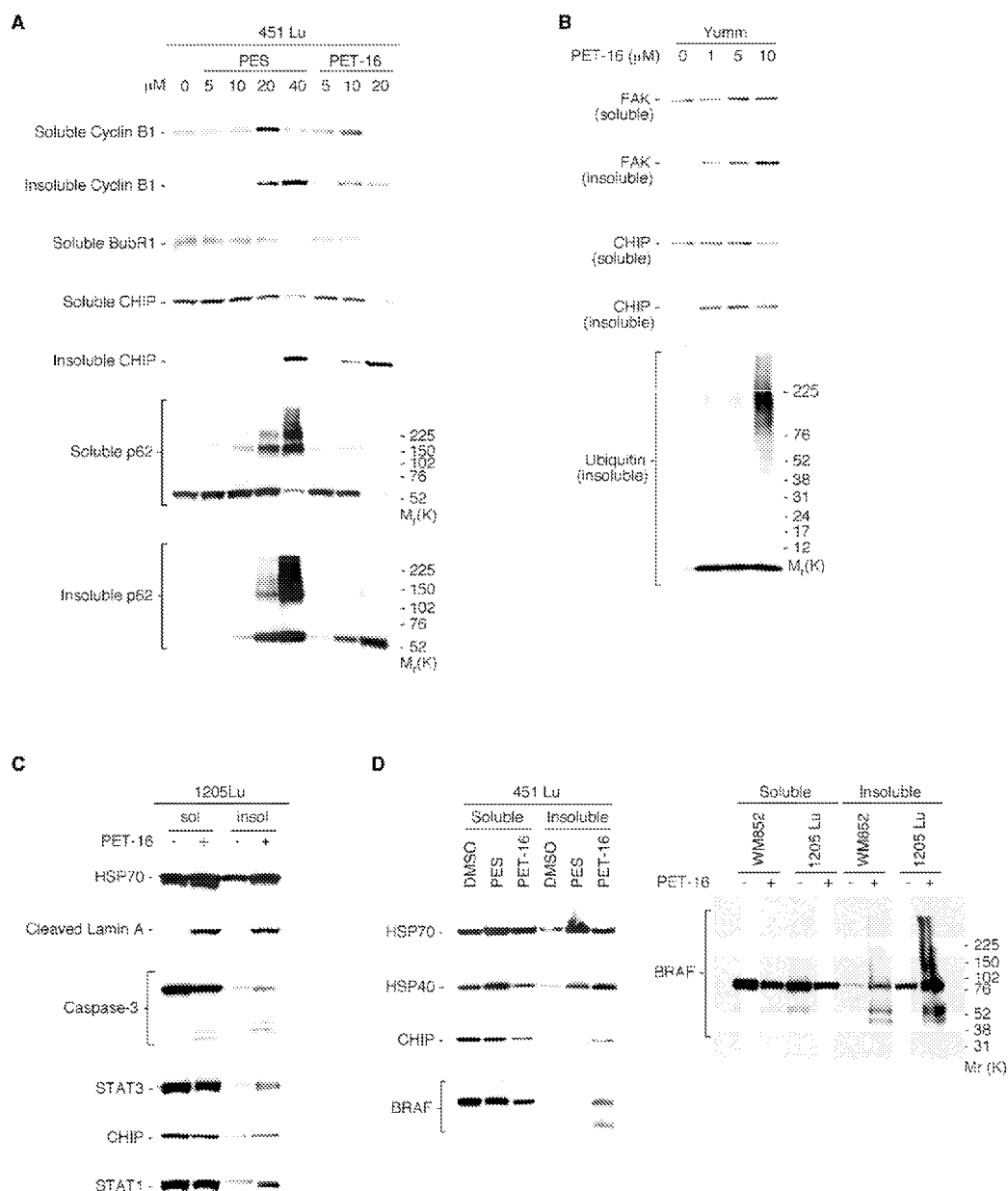

FIG. 10 is a graph demonstrating the cytotoxicity of PET-16 for human melanoma tumor cell lines. MTT assays of human melanoma cell lines, as indicated, treated with the indicated concentration of PET-16 for 72 hours. The corresponding cell survival is normalized to vehicle (DMSO) treatment. Average and standard deviation (s.d.) from three independent experiments are shown. This compound exhibits similar cytotoxic potential against a diverse group of human melanoma cell lines, independent of their genotype.

FIGS. 11A through 11D are Western blots that illustrate that in cells treated with PET-16, HSP70/HSP90 client proteins exhibit altered expression. PET-16 promotes the loss of HSP90/HSP70 client proteins from the soluble fraction and the accumulation of some of these client proteins in the protein detergent-insoluble cellular fraction. Human melanoma cell lines (451 Lu, 1205 Lu and WM852) and mouse melanoma cell line (Yumm), as indicated, were treated with DMSO, PES or PET-16 for 24 hours. Cells were fractionated into detergent-soluble and detergent-insoluble preparations and assayed by Western blot (WB) analysis for the proteins indicated. Note that the HSP70 cochaperones (HSP40 and CHIP), the ubiquitin-binding triage protein (p62/SQSTM1), cell-cycle checkpoint modulators (Cyclin B1 and BubR1), ubiquitin, oncogenic factors critically involved in processes such as tumor growth and metastasis (STAT1, STAT3 and FAK), apoptosis markers (Caspase-3 and Cleaved Lamin A), and melanoma malignancy marker (BRAF/V600E) exhibit altered expression patterns after PET-16 treatment. The expression of many of these proteins is reduced in the soluble cell fractions, and often the abundance increases in the detergent insoluble fractions. This is indicative of loss of function of the client proteins.

Figures 12A, 12B:
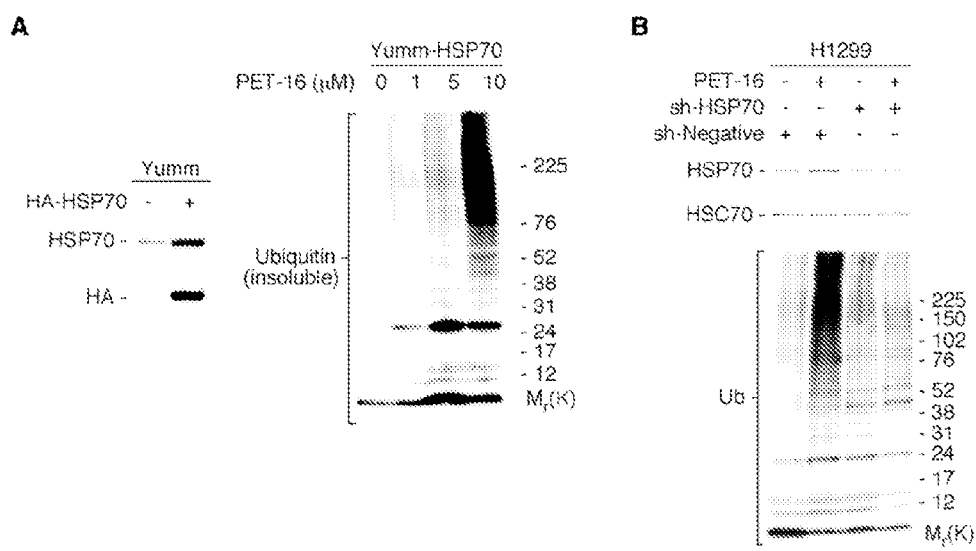
Figures 13A, 13B, 13C, 13D, 13E, 13F:
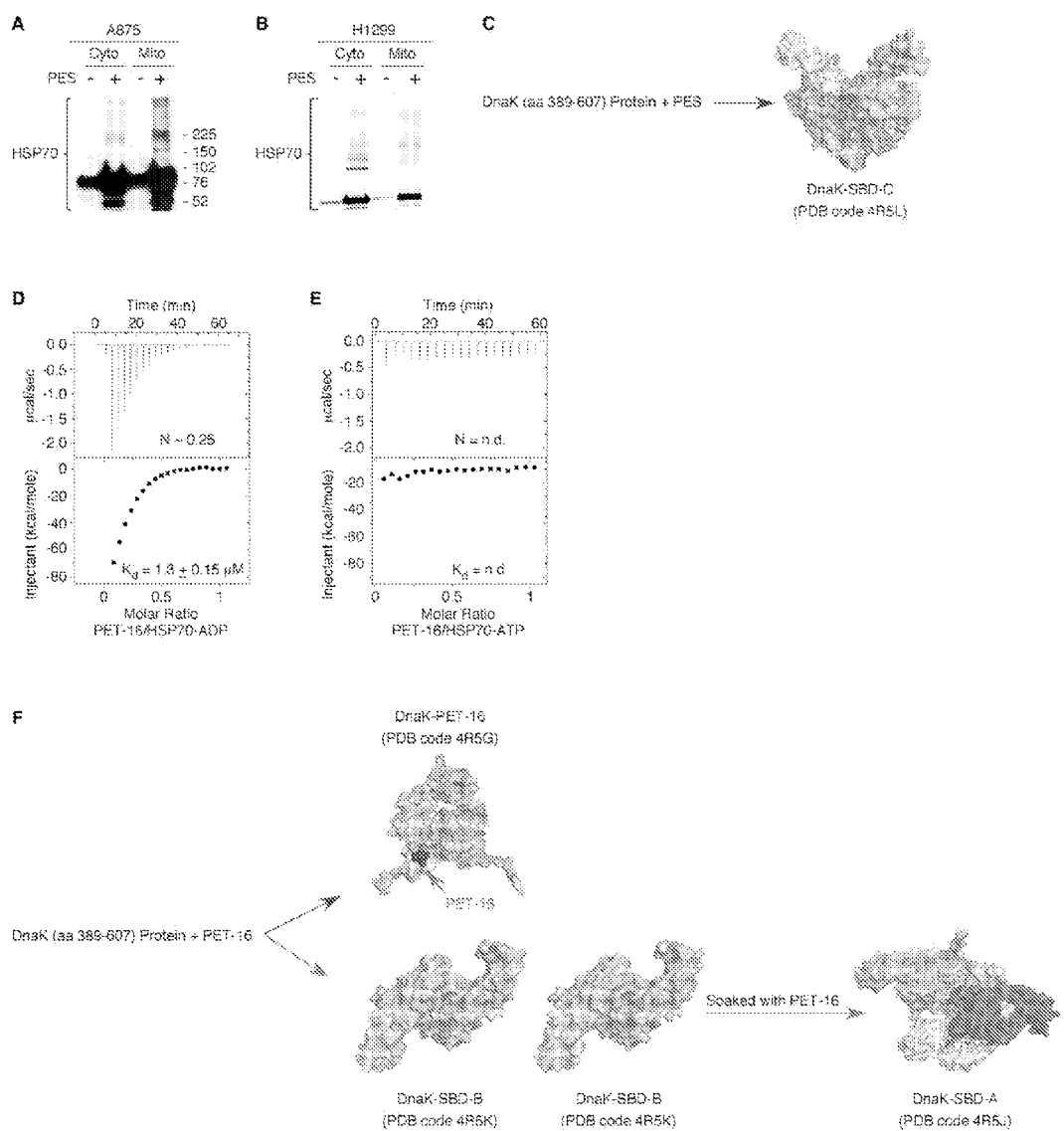

FIGS. 12A and 12B illustrate that PET-16 treatment leads to the accumulation of proteins that are now modifed with ubiquitin, a molecular tag suggesting that the proteins are being targeted for degradation, as expected if the proteins are no longer properly folded because HSP70 function is impaired. PET-16 promotes the accumulation of ubiquitinated polypeptides in an HSP70-dependent manner (FIGS. 12A and 12B) Mouse Yumm melanoma tumor cell line, stably transfected with vector or hemagglutinin (HA)-tagged human full-length HSP70 construct (12A) and human H1299 lung carcinoma cells, transfected with a negative shRNA (sh-Negative) or with HSP70 shRNAs (sh-HSP70) (12B), were treated with DMSO or PET-16, as indicated. Proteins were assayed by WB for ubiquitin in the detergent insoluble fraction (FIGS. 12A and B) and for HSP70 and HSC70 in the detergent-soluble fraction (12B). Note PET-16 treated cells exhibit an accumulation of ubiquitinated proteins, and this is reduced when HSP70 is reduced.

FIGS. 13A through 13F illustrate that PET-16 binds directly to HSP70 and promotes its self-association. (FIG. 13A) Cyto- and mito-extracts from tumor cells treated as indicated were analyzed for molecular chaperones HSP70, HSP90 and HSP40. (FIG. 13B) The indicated subcellular fractions were crosslinked with BMH. HSP70 oligomers were detected by immunoblotting with anti-HSP70 antibody. (FIG. 13C) PES directly promotes tetramerization of DnaK-SBD (aa 389-607), as demonstrated by the crystal structure (PDB code 4R5L). (FIGS. 13D and E) ITC binding isotherms recorded for full-length recombinant human HSP70 protein pretreated either with ADP (FIG. 13D) or ATP (FIG. 13E) and titrated into a solution of PET-16. The data shown here are representative of two independent experiments. Note, PET-16 binds directly to ADP-bound HSP70, but not ATP-bound HSP70. Also, the ITC binding curve (FIG. 13D) supports a stoichiometry (N=0.25) whereby one molecule of PET-16 binds in a complex containing four molecules of ADP-bound HSP70. This contrasts with FIG. 3C, whereby one molecule of PET-16 binds to two molecules of ADP-bound HSP70. This study demonstrates that PET-16 binds directly to ADP-bound HSP70 resulting in its self-oligomerization, and that PET-16 exhibits greater affinity toward tetrameric ADP-bound HSP70 (N=0.25, Kd =1.3+/−0.15 micromolar), than dimeric ADP-bound HSP70 (N=0.5, Kd =3.8+/−1.0 micromolar). (FIG. 13F) PET-16 directly promotes dimerization and tetramerization of DnaK-SBD (aa 389-607), as demonstrated by the dimeric crystal structure (PDB code 4R5G) and the tetrameric crystal structure (PDB code 4R5J).

Figures 14A, 14B:
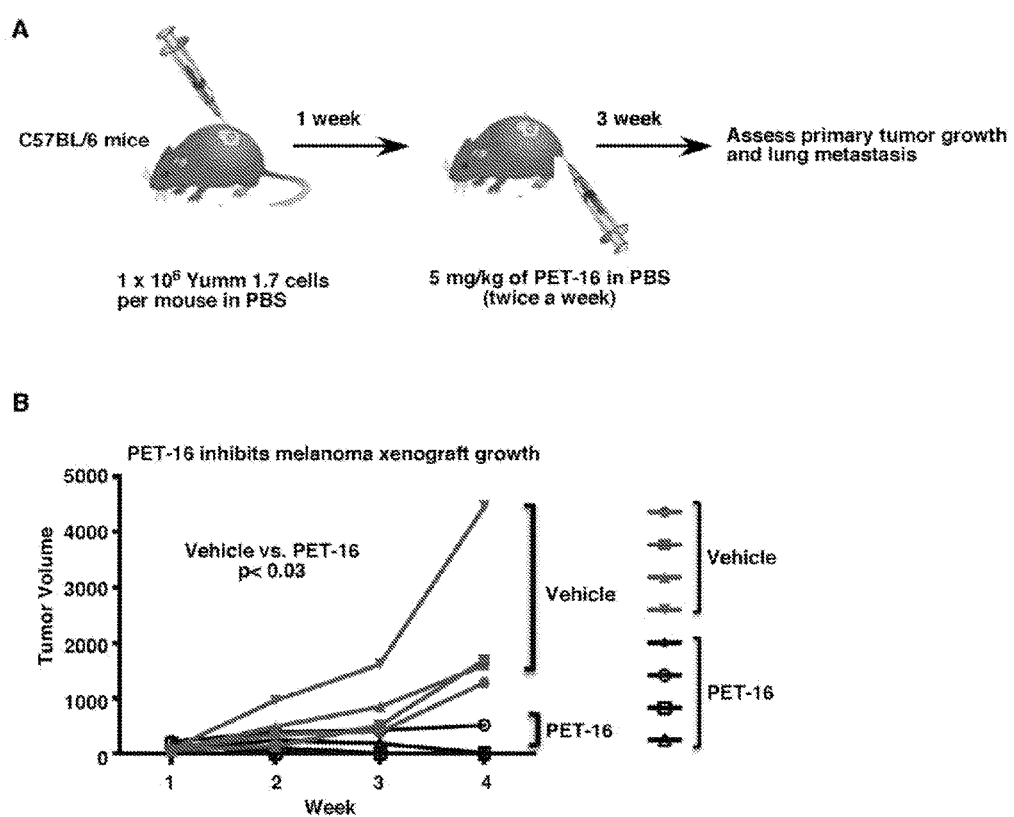

FIGS. 14A and 14B provide evidence that PET-16 impairs melanoma growth in vivo as a single agent. A well-recognized pulmonary metastatic model was utilized in which immunocompetent, wild-type C57BL/6 mice were injected with the metastatic mouse melanoma cell line Yumm 1.7, as indicated. The results of the experiment provide evidence that PET-16 is able to significantly impair the appearance of lung metastases as a single agent. FIG. 14A is a summary of the steps entailed in the model. FIG. 14B shows that PET-16 inhibits melanoma xenograft growth.

DETAILED DESCRIPTION OF THE INVENTION

Described herein is a novel class of selective small molecule modulators of the mammalian stress-inducible molecular chaperone HSP70 and of its bacterial homologue, DnaK. These proteins function as critical regulators of cellular proteostasis, especially during conditions of enhanced stress. Importantly, the inhibitors described herein are unusual in that they bind to the C-terminal domains of HSP70/DnaK within HSP70 residues 386-616 of SEQ ID NO: 2 (comparable DnaK residues 389-607 of SEQ ID NO: 4); the inhibitor binding site is distinct from the substrate binding pocket. The present invention, therefore, provides the first identification and characterization of this critical allosteric site.

As used herein, modulation of HSP70 refers to modulating one or more of nascent protein folding, refolding of misfolded proteins, reducing/preventing denatured/misfolded protein aggregation, modulating assembly/disassembly of protein complexes, targeting proteins for proper intracellular location, targeting altered proteins for degradation by proteasomes, lysosomes or in pathways of autophagy, modulating cell death pathways, chaperone protein binding, client protein binding, modulation of cellular stress response, and modulation of caspase cleavage pathways.

Advantageously, the small molecule compounds discussed herein have a strong dependence on tumor cells, but not normal cells, thereby resulting in the preferential killing of tumor cells relative to normal cells.

Of importance, an allosteric pocket located outside the canonical substrate binding cleft in the C-terminus of DnaK and HSP70 was discovered and is a site of interaction with a compound discussed herein. Previous to the identification of the compounds discussed herein, no natural or synthetic small molecule compounds are known to bind to this previously uncharacterized pocket. As a result of this unprecedented discovery, the inventors were able to identify HSP70 inhibitors, construct novel HSP70 inhibitors, modify the structures of known compounds to bind to this allosteric site, and screen databases or libraries for effective HSP70 inhibitors.

The compounds discussed herein disrupt the HSP70 molecular chaperone machinery, leading to altered substrate fate and an accumulation of misfolded, mislocated, and non-functional proteins. When occupied by a compound described herein, the allosteric pocket in HSP70 and DnaK inhibit chaperone activities resulting in (i) inhibition of malignant cell growth, (ii) inhibition of cytotoxicity of malignant cells (iii) reduced cell cycle progression (iv) altered expression of several proteins contributing to a transformed phenotype and (v) reduction in invasive potential of cancer cells at doses not toxic to normal cells. By doing so, the compounds discussed herein dysregulate cell cycle control, alter autophagy-lysosome systems or impair ubiquitin-proteasome pathways to reduce the ability of tumor cells to maintain protein quality control. Advantageously, the methods for occupying this allosteric pocket with the compounds described herein result in dual inhibition of HSP70 and HSP90 oncogenic pathways and functional depletion of onco-proteins driving malignant processes and cell signaling events. Accordingly, the compounds described herein may be used to induce mitochondrial cell death in transformed cells, e.g., cancer cells, while having minimal or no effect on normal mitochondria. Such methods of using the compounds and methods of designing similarly functional compounds are provided.

A. General Definitions

Unless defined otherwise in this specification, technical and scientific terms used herein have the same meaning as commonly understood by one of ordinary skill in the art and by reference to published texts, which provide one skilled in the art with a general guide to many of the terms used in the present application.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively, i.e., to include other unspecified components or process steps. The words "consist", "consisting", and its variants, are to be interpreted exclusively, rather than inclusively, i.e., to exclude components or steps not specifically recited.

As used herein, the term "about" means a variability of 10% from the reference given, unless otherwise specified.

The term "regulation" or variations thereof as used herein refers to the ability of a compound of formula (I) to inhibit one or more components of a biological pathway.

A "subject" is a mammal, e.g., a human, mouse, rat, guinea pig, dog, cat, horse, cow, pig, or non-human primate, such as a monkey, chimpanzee, baboon or gorilla.

As used herein, "disease", "disorder" and "condition" are used interchangeably, to indicate an abnormal state in a subject.

The term "treating" or "treatment" is meant to encompass administering to a subject a compound described herein for the purposes of amelioration of one or more symptoms of a disease or disorder.

The nucleotide and amino acid sequences of Human Stress-Inducible HSP70 are provided in public databases, such as GenBank Accession Nos. NM_005345.4 (SEQ ID NO: 1) and AAD21816.1 (SEQ ID NO: 2). This amino acid sequence will then provide the reference for the numbering of all of the HSP70 amino acids disclosed in this specification. Similarly, the nucleotide and amino acid sequences of E. coli DnaK are provided in public databases, such as GenBank at Accession Nos. K01298.1 (SEQ ID NO: 3) and AAA23694.1 (SEQ ID NO: 4). This amino acid sequence will then provide the reference for the numbering all of the DnaK amino acids.

B. The Compounds

As used herein and throughout this specification below for ease of review, the phrases "chemical compound" or "compound" are used interchangeably to refer to the specific compounds described herein as well as other compounds or molecules identified through use of the screening assay described in detail below. In one embodiment, the compounds described herein are of formula (I) of the structure:

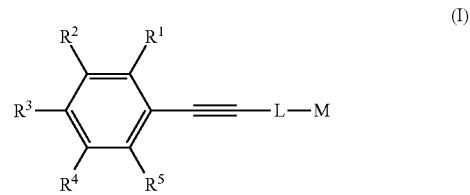

(I)

In this structure, L is absent or a noncleavable organic moiety. The term "noncleavable organic moiety" as used herein refers to a small organic ligand which is not severed from one or both of the alkynyl moiety or "M" group. In one embodiment, the noncleavable organic moiety is not cleaved from the compound when administered to a subject as described below. In another embodiment, the noncleavable organic moiety is not cleaved at cellular uptake through one or more of a cell wall, cell membrane, plasma membrane, or subcellular membrane. In a further embodiment, the noncleavable organic moiety is not cleaved when the compound is delivered through one or more of a cell wall, cell membrane, plasma membrane, or subcellular membrane. In yet another embodiment, the noncleavable moiety is not cleaved when the compound penetrates through one or more of a cell wall, cell membrane, plasma membrane, or subcellular membrane. In one embodiment, L is optionally substituted $C_1$ to $C_{10}$ alkyl, optionally substituted $C_1$ to $C_{10}$ alkenyl, optionally substituted $C_1$ to $C_{10}$ alkynyl, optionally substituted aryl, optionally substituted heteroaryl, optionally substituted heterocycle, optionally substituted $C_1$ to $C_{10}$ alkylsulfonyl, optionally substituted arylamino, optionally substituted heteroarylamino, optionally substituted heterocycleamino, optionally substituted $C_1$ to $C_{10}$ alkylcarbonylamino, optionally substituted alkylsulfonylamino, optionally substituted $C_1$ to $C_{10}$ alkylamino, optionally substituted $C_1$ to $C_{10}$ dialkylamino, optionally substituted $C_1$ to $C_{10}$ amido, optionally substituted $C_1$ to $C_{10}$ carboxy, optionally substituted $C_1$ to $C_{10}$ alkoxycarbonyl, optionally substituted $C_1$ to $C_{10}$ alkylcarbonyl, optionally substituted alkylaminocarbonyl, optionally substituted arylaminocarbonyl, optionally substituted heteroarylaminocarbonyl, optionally substituted heterocycleaminocarbonyl, sulfamido or sulfonamide. In another embodiment, L is optionally substituted $C_1$ to $C_{10}$ alkyl. In a further embodiment, L is $C_1$ to $C_6$ alkyl.

$R^1$ to $R^5$ are, independently, selected from among H, optionally substituted $C_1$ to $C_R$) alkyl, optionally substituted $C_1$ to $C_{10}$ alkenyl, optionally substituted $C_1$ to $C_{10}$ alkynyl, OH, halogen, $NH_2$, optionally substituted aryl, optionally substituted heteroaryl, optionally substituted heterocycle, optionally substituted $C_1$ to $C_{10}$ alkoxy, optionally substituted $C_1$ to $C_{10}$ hydroxyalkyl, optionally substituted aryloxy, optionally substituted heteroaryloxy, optionally substituted heterocycleoxy, optionally substituted $C_1$ to $C_{10}$ alkylthio, optionally substituted $C_1$ to $C_{10}$ alkylsulfonyl, optionally substituted arylamino, optionally substituted heteroarylamino, optionally substituted heterocycleamino, optionally substituted $C_1$ to $C_{10}$ alkylcarbonylamino, optionally substituted alkylsulfonylamino, optionally substituted $C_1$ to $C_{10}$ alkylamino, optionally substituted $C_1$ to $C_{10}$ dialkylamino, optionally substituted $C_1$ to $C_{10}$ amido, $NO_2$, optionally substituted $C_1$ to $C_{10}$ carboxy, optionally substituted $C_1$ to $C_{10}$ alkoxycarbonyl, optionally substituted $C_1$ to $C_{10}$ alkylcarbonyl, optionally substituted $C_1$ to $C_{10}$ alkylcarbonyloxy, optionally substituted alkylaminocarbonyl, optionally substituted arylaminocarbonyl, optionally substituted heteroarylaminocarbonyl, optionally substituted heterocycleaminocarbonyl, phosphate, sulfamido and sulfonamide. In one embodiment, when (i) L is absent, (ii) M is $PPh_3$ or $PPh_2CH_3$ and (iii) the compound is a bromide salt, not all of $R^1$ to $R^5$ are H. In another embodiment, $R^1$ to $R^5$ are H. In another embodiment, $R^1$ to $R^5$ may be H when (i) L is absent, (ii) M is $PPh_3$ or $PPh_2CH_3$ and (iii) the compound is a bromide salt.

M is a ligand which promotes one or more of cellular uptake, delivery, or penetration of a small molecule through one or more of a cell wall, cell membrane, plasma membrane, or subcellular membrane (including lysosomal membrane and mitochondrial membrane). In one embodiment, M is an optionally substituted phosphine. In another embodiment, M is optionally substituted triphenylphosphine. In yet another embodiment, M is triphenylphosphine (TPP). In a further embodiment, M is of the following structure:

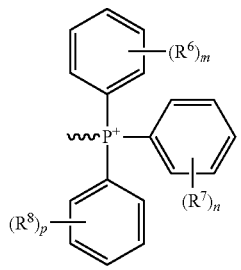

In this structure, m, n, and p are, independently, 0 to 5 or integers there between.

$R^6$, $R^7$, and $R^8$ are, independently, selected from among H, optionally substituted $C_1$ to $C_{10}$ alkyl, optionally substituted $C_1$ to $C_{10}$ alkenyl, optionally substituted $C_1$ to $C_{10}$ alkynyl, OH, halogen, $NH_2$, optionally substituted aryl, optionally substituted heteroaryl, optionally substituted heterocycle, optionally substituted $C_1$ to $C_{10}$ alkoxy, optionally substituted $C_1$ to $C_{10}$ hydroxyalkyl, optionally substituted aryloxy, optionally substituted heteroaryloxy, optionally substituted heterocycleoxy, optionally substituted $C_1$ to $C_{10}$ alkylthio, optionally substituted $C_1$ to $C_{10}$ alkylsulfonyl, optionally substituted arylamino, optionally substituted heteroarylamino, optionally substituted heterocycleamino, optionally substituted $C_1$ to $C_{10}$ alkylcarbonylamino, optionally substituted alkylsulfonylamino, optionally substituted $C_1$ to $C_{10}$ alkylamino, optionally substituted $C_1$ to $C_{10}$ dialkylamino, optionally substituted $C_1$ to $C_{10}$ amido, $NO_2$, optionally substituted $C_1$ to $C_{10}$ carboxy, optionally substituted $C_1$ to $C_{10}$ alkoxycarbonyl, optionally substituted $C_1$ to $C_{10}$ alkylcarbonyl, optionally substituted $C_1$ to $C_{10}$ alkylcarbonyloxy, optionally substituted alkylaminocarbonyl, optionally substituted arylaminocarbonyl, optionally substituted heteroarylaminocarbonyl, optionally substituted heterocycleaminocarbonyl, phosphate, sulfamido and sulfonamide.

In one embodiment, the compound is of formula (II), wherein X is acetate, adipate, alginate, ammonium, ascorbate, aspartate, benzenesulfonate, benzoate, bicarbonate, bisulfate, borate, bromide, bromide chloride, butyrate, camsylate, camphorate, camphorsulfonate, caproate, chloride, citrate, dibromide, dichloride, digluconate, ethylenediamine, fluoride, formate, fumarate, gluconate, glutamate, glutarate, glycerolphosphate, halogen, 2-hydroxyethansulfonate, hemisulfate, heptanoate, hexanoate, iodide, lactate, laurate, maleate, malonate, malate, maleate, mesylate, myristyl methanesulfonate, mesitylenesulfonate, naphthylenesulfonate, napsylate, nicotinate, nitrate, oleate, oxalate, oxylate, palmitate, pamoate, pectinate, persulfate, 3-phenylpropionate, phosphate, picrate, pivalate, propionate, pyruvate, saccharinate, sebacate, stearate, succinate, sulfate, sulfonate, tartrate, tetrafluoroborate, trifluoromethyl sulfonate, tosylate, trichloroacetate, trifluoroacetate, p-toluenesulfonate, undecanoate, valerate, or xinafoate.

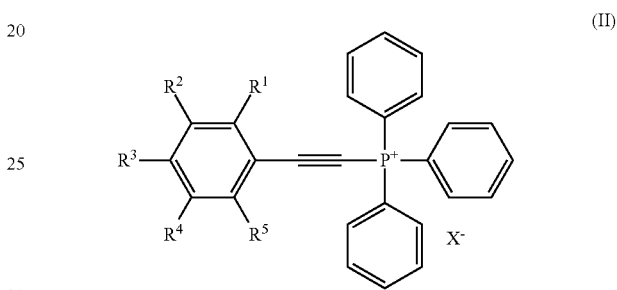

In another embodiment, the compound is of formula (III), wherein q is 1 to 6 and X is acetate, adipate, alginate, ammonium, ascorbate, aspartate, benzenesulfonate, benzoate, bicarbonate, bisulfate, borate, bromide, bromide chloride, butyrate, camsylate, camphorate, camphorsulfonate, caproate, chloride, citrate, dibromide, dichloride, digluconate, ethylenediamine, fluoride, formate, fumarate, gluconate, glutamate, glutarate, glycerolphosphate, halogen, 2-hydroxyethansulfonate, hemisulfate, heptanoate, hexanoate, iodide, lactate, laurate, maleate, malonate, malate, maleate, mesylate, myristyl methanesulfonate, mesitylenesulfonate, naphthylenesulfonate, napsylate, nicotinate, nitrate, oleate, oxalate, oxylate, palmitate, pamoate, pectinate, persulfate, 3-phenylpropionate, phosphate, picrate, pivalate, propionate, pyruvate, saccharinate, sebacate, stearate, succinate, sulfate, sulfonate, tartrate, tetrafluoroborate, trifluoromethyl sulfonate, tosylate, trichloroacetate, trifluoroacetate, p-toluenesulfonate, undecanoate, valerate, or xinafoate.

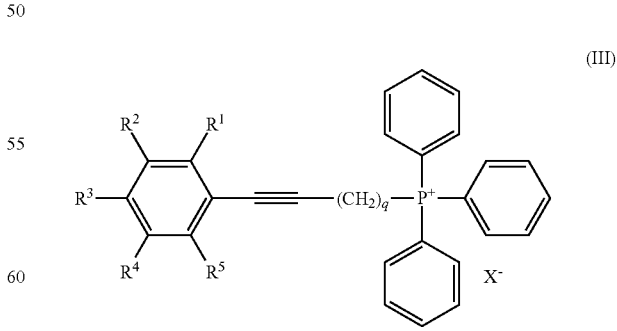

In still another embodiment, the compound is one of the following, wherein, X is acetate, adipate, alginate, ammonium, ascorbate, aspartate, benzenesulfonate, benzoate, bicarbonate, bisulfate, borate, bromide, bromide chloride, butyrate, camsylate, camphorate, camphorsulfonate, caproate, chloride, citrate, dibromide, dichloride, digluconate, ethylenediamine, fluoride, formate, fumarate, gluconate, glutamate, glutarate, glycerolphosphate, halogen, 2-hydroxyethansulfonate, hemisulfate, heptanoate, hexanoate, iodide, lactate, laurate, maleate, malonate, malate, maleate, mesylate, myristyl methanesulfonate, mesitylenesulfonate, naphthylenesulfonate, napsylate, nicotinate, nitrate, oleate, oxalate, oxylate, palmitate, pamoate, pectinate, persulfate, 3-phenylpropionate, phosphate, picrate, pivalate, propionate, pyruvate, saccharinate, sebacate, stearate, succinate, sulfate, sulfonate, tartrate, tetrafluoroborate, trifluoromethyl sulfonate, tosylate, trichloroacetate, trifluoroacetate, p-toluenesulfonate, undecanoate, valerate, or xinafoate.

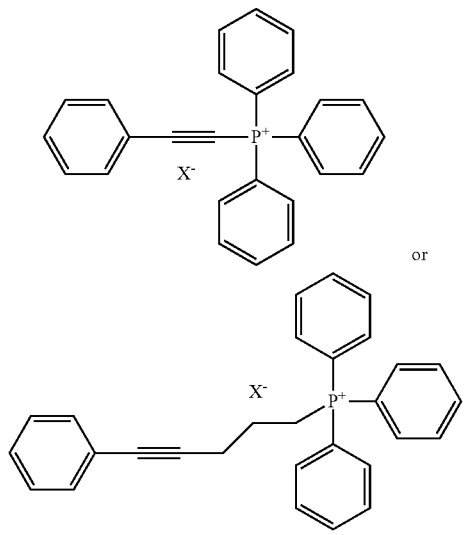

or

In yet another embodiment, the compound is:

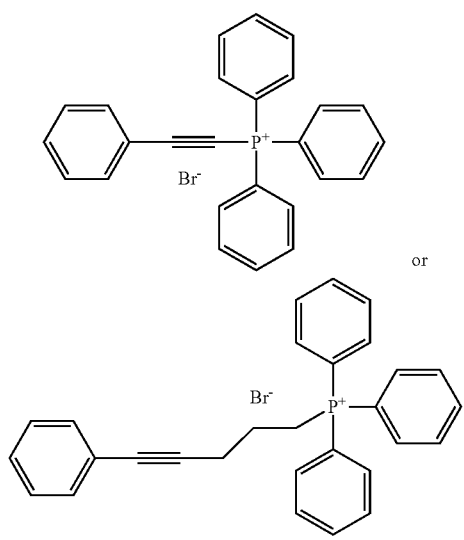

or

In one embodiment, the compounds discussed herein can exist as their corresponding salt, ester, or prodrug. Salts of such compounds can be prepared by reacting the compound with an acid or a base. Examples of salts for use as described herein include acetate, adipate, alginate, ammonium, ascorbate, aspartate, benzenesulfonate, benzoate, bicarbonate, bisulfate, borate, bromide, bromide chloride, butyrate, camsylate, camphorate, camphorsulfonate, caproate, chloride, citrate, dibromide, dichloride, digluconate, ethylenediamine, fluoride, formate, fumarate, gluconate, glutamate, glutarate, glycerolphosphate, halogen, 2-hydroxyethansulfonate, hemisulfate, heptanoate, hexanoate, iodide, lactate, laurate, maleate, malonate, malate, maleate, mesylate, myristyl methanesulfonate, mesitylenesulfonate, naphthylenesulfonate, napsylate, nicotinate, nitrate, oleate, oxalate, oxalate, palmitate, pamoate, pectinate, persulfate, 3-phenylpropionate, phosphate, picrate, pivalate, propionate, pyruvate, saccharinate, sebacate, stearate, succinate, sulfate, sulfonate, tartrate, tetrafluoroborate, trifluoromethyl sulfonate, tosylate, trichloroacetate, trifluoroacetate, p-toluenesulfonate, undecanoate, valerate, or xinafoate salts. In one embodiment, the compound is the acetate, adipate, alginate, ammonium, ascorbate, aspartate, benzenesulfonate, benzoate, bicarbonate, bisulfate, borate, bromide, bromide chloride, butyrate, camsylate, camphorate, camphorsulfonate, caproate, chloride, citrate, dibromide, dichloride, digluconate, ethylenediamine, fluoride, formate, fumarate, gluconate, glutamate, glutarate, glycerolphosphate, halogen, 2-hydroxyethansulfonate, hemisulfate, heptanoate, hexanoate, iodide, lactate, laurate, maleate, malonate, malate, maleate, mesylate, myristyl methanesulfonate, mesitylenesulfonate, naphthylenesulfonate, napsylate, nicotinate, nitrate, oleate, oxalate, oxylate, palmitate, pamoate, pectinate, persulfate, 3-phenylpropionate, phosphate, picrate, pivalate, propionate, pyruvate, saccharinate, sebacate, stearate, succinate, sulfate, sulfonate, tartrate, tetrafluoroborate, trifluoromethyl sulfonate, tosylate, trichloroacetate, trifluoroacetate, p-toluenesulfonate, undecanoate, valerate, or xinafoate.

In a further embodiment, a compound described herein may be a solvate. The term "solvate" as used herein is a physical association or binding of a compound described herein with one or more solvent molecule.

In another embodiment, a compound described herein may be a prodrug. The term prodrug is meant to described a chemical compound, which, when administered in such form, converts to the active moiety in vivo. In one embodiment, the prodrug is in the form of an ester, carbamate, sulfate, ether, oxime, carbonate, among others. In another embodiment, the prodrug is an ester In a further embodiment, a compound described herein also encompasses "metabolites". The term "metabolite" as used herein describes a unique product formed by processing the compound by the cell or subject. In one embodiment, metabolites are formed in vivo.

Some compounds may possess one or more chiral centers. Accordingly, the chemical compounds include each enantiomer, combinations of all possible enantiomers, diastereomers, racemers, and mixtures thereof. Where multiple chiral centers exist in the compounds described herein, also contemplated are each possible combinations of chiral centers within a compound, as well as all possible enantiomeric mixtures thereof. Those skilled in the art can prepare such optically active forms and resolve/synthesize racemic forms from their corresponding optically active forms.

"Alkyl" refers to a hydrocarbon chain that may be straight or branched or contains a cyclic alkyl radical. In one embodiment, an alkyl contains 1 to 10 carbon atoms or integers or ranges there between. Examples of alkyl groups that are hydrocarbon chains include, but are not limited to, methyl, ethyl, propyl, butyl, pentyl, hexyl, heptyl, octyl, nonyl, decyl, and any isomers thereof. Examples of alkyl groups that consist of or contain a cyclic alkyl radical include, but are not limited to, cyclopropyl, cyclobutyl, cyclopentyl, 3,3-dimethylcyclobutyl, (cyclopropyl)methyl, and (cyclopentyl)methyl.

"Alkenyl" refers to hydrocarbon chain which is straight or branched and contains at least one degree of unsaturation, i.e., at least one carbon-carbon double bond in the E or Z conformation. In one embodiment, an alkenyl contains 2 to about 10 carbon atoms or integers or ranges there between. In one embodiment, the alkenyl may contain 1 to 4 double bonds or integers there between. Examples of alkenyl groups include, but are not limited to, ethene, propene, butene, pentene, hexene, heptene, octane, nonene, or decene.

"Alkynyl" refers to hydrocarbon chain which is straight or branched and contains at least one degree of unsaturation, i.e., at least one carbon-carbon triple bond. In one embodiment, an alkynyl contains 2 to about 10 carbon atoms or integers or ranges there between. In one embodiment, the alkynyl contains 1 to 4 double bonds or integers there between. Examples of alkynyl groups include, but are not limited to, ethyne, propene, butyne, pentyne, hexyne, heptyne, octyne, nonyne, or decyne.

"Alkoxy" refers to (alkyl)O, where the alkyl is defined above. In one embodiment, an alkoxy contains 1 to about 10 carbon atoms or integers or ranges there between. Examples of alkoxy include, without limitation, methoxy, ethoxy, propoxy, butoxy, pentoxy, hexoxy, heptoxy, octoxy, nonoxy, or decoxy.

"Hydroxyalkyl" refers to (alkyl)OH, where the alkyl is defined above. The OH moiety of the hydroxyalkyl may be bound to any carbon atom of the alkyl chain. In one embodiment, a hydroxyalkyl contains 1 to about 10 carbon atoms or integers or ranges there between. Examples of hydroxyalkyl include, without limitation, $CH_2OH$, $CH_2CH_2OH$, $CH(OH)CH_3$, $CH_2CH_2CH_2OH$, $CH_2CH(OH)CH_3$, $CH(OH)CH_2CH_3$, $C(OH)(CH_3)_2$, (2-hydroxy)-cyclopentyl, (3-hydroxy)-cyclobutyl, and the like.

"Aryl" refers to an aromatic hydrocarbon group containing carbon atoms in the backbone of the group. In one embodiment, the aryl contains about 5 to about 8 carbon atoms or integers or ranges there between. In one embodiment, the aryl is a phenyl group. In another embodiment, the aryl is naphthyl, 1,2,3,4-tetrahydronaphthyl, or indanyl.

"Halogen" refers to F, Cl, Br and I.

The term "heteroatom" refers to a sulfur, nitrogen, or oxygen atom.

"Heteroaryl" refers to an aromatic 5- or 6-membered ring containing at least one ring heteroatom. In one embodiment, the heteroaryl contains 1 to about 6 carbon atoms or integers or ranges there between. "Heteroaryl" also includes bicyclic aromatic ring systems wherein a heteroaryl group is fused to at least one other cyclic moiety. In one embodiment, a phenyl group is fused to a 5- or 6-membered monocyclic heteroaryl. In another embodiment, a cyclic alkyl is fused to a monocyclic heteroaryl. Examples of heteroaryl groups include, without limitation, furan, thiophene, indole, azaindole, oxazole, thiazole, isoxazole, isothiazole, imidazole, pyridine, pyrimidine, pyrazine, pyridazine, pyrrole, pyrazole, 1,3,4-oxadiazole, 1,2,4-triazole, tetrazole, benzoxazole, benzothiazole, benzofuran, benzisoxazole, benzimidazole, azabenzimidazole, indazole, quinazoline, quinoline, and isoquinoline.

"Heterocycle" refers to a monocyclic or bicyclic group having a heteroatom in at least 1 ring of the heterocycle. In one embodiment, the heterocycle contains 3 to about 7 carbon atoms or integers or ranges there between. Examples of heterocycles include, but are not limited, to aziridine, oxirane, thiirane, morpholine, thiomorpholine, pyrroline, pyrrolidine, azepane, dihydrofuran, THF, dihydrothiophene, tetrahydrothiophene, dithiolane, piperidine, 1,2,3,6-tetrahydropyridine-1-yl, tetrahydropyran, pyran, thiane, thiine, piperazine, homopiperazine, oxazine, azecane, tetrahydroquinoline, perhydroisoquinoline, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo [2.2.2]octane, 2,7-dioxa-5-azabicyclo[2.2.2]octane, 2-oxa-5-azabicyclo [2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo [3.1.1]heptane, 8-oxa-3-azabicyclo[3.2.1]octan-3-yl, 2,5-diazabicyclo[2.2.1]heptane-5-yl, 6-azabicyclo[3.2.1]oct-6-yl, 8-azabicyclo[3.2.1]octan-8-yl, 3-oxa-7,9-diazabicyclo [3.3.1]nonan-9-yl, 9-oxa-3-azabicyclo[3.3.1]nonan-3-yl, 3-oxa-9-azabicyclo [3.3.1]nonan-9-yl, 3,7-dioxa-9-azabicyclo[3.3.1]nonan-9-yl, 3,4-dihydro-2H-1,4-benzoxazin -7-yl, thiazine, dithiane, and dioxane.

"Alkylthio" refers to a (alkyl)S∼ group. Examples of alkylthio include, without limitation, $SCH_3$, $SCH_2CH_3$, $SCH_2CH_2CH_3$, and $SCH_2CH_2CH_2CH_3$.

"Aryloxy" refers to a (aryl)O∼ group. Examples of aryloxy include, without limitation, phenoxy and pentafluorophenoxy.

"Heteroaryloxy" refers to a (heteroaryl)O∼ group. Examples of heteroaryloxy include, but are not limited to, (3-pyridyl)oxy and (4-pyridyl)oxy.

"Heterocycleoxy" refers to a (heterocycle)O∼ group. Examples of heterocycleoxy include, but are not limited to, (4-piperdinyl)oxy.

"Alkylsulfonyl" refers to an (alkyl)$SO_2$∼ group. Examples of alkylsulfonyl include, but are not limited to, $CH_3SO_2$, $CH_3CH_2CH_2SO_2$, $CH_3CH(CH_3)SO_2$, $CH_3CH_2CH_2CH_2SO_2$, $CH_3CH(CH_3)CH_2SO_2$, $(CH_3)_3CSO_2$, and the like.

"Alkylamino" refers to group containing an NH or N group, where the nitrogen atom is attached to 1 or 2 alkyl substituents and is bound through the nitrogen atom. In one embodiment, the alkylamino is a monoalkylamino group, i.e., (alkyl)NH∼ group. In another embodiment, the alkylamino is a dialkylamino group, i.e., (alkyl)(alkyl)N∼ group, where each alkyl group is independently selected. In another embodiment, two alkyl groups may be taken together to form a 3- to 7-membered nitrogen-containing heterocycle wherein up to two of the carbon atoms of the heterocycle can be replaced with N(H), N($C_1$ to $C_6$ alkyl), N(aryl), N(heteroaryl), O, S, S(O), or $S(O)_2$. Examples of alkylamino include, but are not limited to $CH_3NH$, $CH_3CH_2NH$, $CH_3CH_2CH_2NH$, $CH_3CH_2CH_2CH_2NH$, $(CH_3)_2CHNH$, $(CH_3)_2CHCH_2NH$, $CH_3CH_2CH(CH_3)NH$, $(CH_3)_3CNH$, $N(CH_3)_2$, $N(CH_2CH_3)(CH_3)$, $N(CH_2CH_3)_2$, $N(CH_2CH_2CH_3)_2$, $N(CH_2CH_2CH_2CH_3)_2$, $N(CH(CH_3)_2)(CH_3)$, and the like.

"Acylamino" refers to an (aryl)NH∼ group. Examples of arylamino include, but are not limited to, phenyl-amino.

"Heteroarylamino" refers to a (heteroaryl)NH∼ group. Examples of heteroarylamino include, but are not limited to (pyridin-2-yl)amino and (pyrimidin-2-yl)amino "Heterocycleamino" refers to a (heterocycle)NH∼ group. Examples of heterocycleamino include, but are not limited to (piperidin-4-yl)amino.

"Alkylcarbonylamino" refers to an (alkyl)C(O)NH∼ group. Examples of alkylcarbonylamino include, but are not limited to, $CH_3CONH$, $CH_3CH_2CONH$, $CH_3CH_2CH_2CONH$, $CH_3CH(CH_3)CONH$, and the like.

"Alkylsulfonylamino" refers to an (alkyl)$SO_2$NH~ group. Examples of alkylsulfonylamino include, but are not limited to $CH_3SO_2NH$, $CH_3CH_2SO_2NH$, $CH_3CH_2CH_2SO_2NH$, $CH_3CH(CH_3)SO_2NH$, and the like.

"Alkylaminocarbonyl" refers to an (alkyl)NHC(O)~ group. Examples of alkylaminocarbonyl include, but are not limited to, $CH_3NHCO$, $CH_3CH_2NHCO$, $CH_3CH_2CH_2NHCO$, $CH_3CH(CH_3)NHCO$, and the like.

"Arylaminocarbonyl" refers to an (aryl)NHC(O)~ group. Examples of arylaminocarbonyl include, but are not limited to phenyl-NHC(O)—.

"Heteroarylaminocarbonyl" refers to an (heteroaryl)NHC(O)~ group. Examples of heteroarylaminocarbonyl include, but are not limited to (pyridine-4-yl)NHC(O).

"Heterocycleaminocarbonyl" refers to an (heterocycle)NHC(O)~ group. Examples of heterocycleaminocarbonyl include, but are not limited to (tetrahydro-2H-pyran-4-yl)NHC(O).

"Amido," as used herein, refers to the~ N(alkyl)C(O)(alkyl) or ~ alkylN(alkyl)C(O)(alkyl) groups.

"Carboxy" as used herein, refers to a ~ C(O)OH group.

"Alkylcarbonyl" as used herein refers to a ~ C(O)alkyl group.

"Alkoxycarbonyl" as used herein refers to a ~ C(O)alkoxy group.

"Alkylcarbonyloxy" as used herein refers to ~ OC(O)alkyl group.

"Sulfamido" as used herein refers to a ~ $NHSO_2NH_2$ moiety.

"Sulfonamido" refers to a ~ $S(O)_2NH_2$ moiety.

"Phosphate" as used herein refers to a ~ $OP(O)(OH)_2$ moiety, and salts thereof. "Phosphate" also includes organophosphates of the formula ~ $OP(O)(alkoxy)_2$, $OP(O)(alkoxy)(aryloxy)$ or ~ $OP(O)(aryloxy)_2$.

Any of the chemical groups or moieties described above may be unsubstituted or substituted with one or more groups provided that the resultant compound is chemically stable. In one embodiment, the chemical groups or moieties may be substituted with one or more halogen, OH, $NH_2$, $N(C_1$ to $C_3$ alkyl)C(O)($C_1$ to $C_6$ alkyl), NHC(O)($C_1$ to $C_6$ alkyl), NHC(O)H, C(O)$NH_2$, C(O)NH($C_1$ to $C_6$ alkyl), C(O)N($C_1$ to $C_6$ alkyl)($C_1$ to $C_6$ alkyl), CN, $C_1$ to $C_6$ alkoxy, C(O)OH, C(O)O($C_1$ to $C_6$ alkyl), C(O)($C_1$ to $C_6$ alkyl), aryl, heteroaryl, heterocycle, NH($C_1$ to $C_6$ alkyl), N($C_1$ to $C_6$ alkyl)($C_1$ to $C_6$ alkyl), OC(O)($C_1$ to $C_6$ alkyl), or $NO_2$.

Methods useful for making compounds embodied by formula (I) are set forth in the Examples below. One of skill in the art will recognize that the description in the Examples can be adapted to produce the other compounds of formula (I) and pharmaceutically acceptable salts and prodrugs thereof.

C. Crystal Structures

As discussed above, a new chemical scaffold was identified in molecules that interact with the C-terminal region of HSP70 and DnaK and inhibit chaperone function. To better understand the mode of action of these compounds, the X-ray crystal structure of the C-terminal substrate-binding domain (SBD) of *Escherichia coli* DnaK in complex with a compound discussed herein, i.e., PET-16, was identified and molecular modeling of the same was performed. See, also, the additional description of X-ray crystal structure studies detailed in Leu 2014, cited above, and incorporated herein by reference.

As used herein, the term "modeling" includes the analysis of molecular structure based on atomic structural information and interaction models. The term "modeling" also includes conventional numeric-based molecular dynamic and energy minimization models, interactive computer graphic models, modified molecular mechanics models, distance geometry and other structure-based constraint models. Such modeling methods are to design or select chemical entities that possess stereochemical complementary to the $HIS_6$-IEGR-DnaK-PET-16 (referred to here as DnaK-PET-16) complex. By "stereochemical complementarity" is meant that the compound or a portion thereof makes a sufficient number of energetically favorable contacts with the residues of the hydrophobic region.

In one embodiment, molecular modeling includes in silico design which includes directly docking molecules from a three-dimensional structural database, to the hydrophobic site. This method uses geometric criteria to assess the goodness-of-fit of a particular molecule to the site. By doing so, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule). HSP70 inhibitors identified on the basis of geometric parameters can then be modified to satisfy criteria associated with chemical complementarity, such as hydrogen bonding, ionic interactions and Van der Waals interactions. Different scoring functions can be employed to rank and select the best molecule from a database or library.

The crystal structure revealed that PET-16 inserts into a hydrophobic pocket formed by residues located in the interdomain and SBDβ subdomain of both DnaK and HSP70 proteins. This region is distinct from the substrate binding site. This pocket is present in the ADP-bound protein conformation, and is distinct from the site where the substrate binds. This is a previously unknown allosteric site in the C-terminus of the protein.

The term "hydrophobic pocket" or "binding pocket" refers to a region within HSP70, DnaK, the C-terminal SBD of *E. coli* or the C-terminal SBD of mammalian stress-inducible HSP70 that associates with a compound described herein. The term "pocket" includes, without limitation, a cleft, channel, groove, cavity or site. Similarly, the phrase "portion of the hydrophobic pocket", or variations thereof, refers to less than all of the amino acid residues that define the hydrophobic pocket. The structure coordinates of amino acid residues that form part of the hydrophobic pocket may be specific for defining the chemical environment of the hydrophobic pocket. For example, the portion of amino acid residues may be key residues that play a role in the binding of the compounds discussed herein or may be residues that are spatially related and define a three-dimensional compartment of the hydrophobic pocket. The amino acid residues may be contiguous or noncontiguous in primary sequence. In one embodiment, part of the binding pocket has at least two amino acid residues, preferably at least three, six, eight, ten, fourteen or fifteen amino acid residues.

As used herein, the term "atomic coordinates" refers to mathematical coordinates that describe the positions of atoms in crystals formed between *E. coli* DnaK and/or mammalian HSP70 with a compound described herein including X, Y, Z and B for each atom. The diffraction data obtained from the crystals may be used to calculate an electron density map of the repeating unit of the crystal. The electron density maps may be used to establish the positions, i.e., coordinates X, Y and Z, of the individual atoms within the crystal. Atomic coordinates may be loaded onto a machine readable-medium for computational manipulation. In one embodiment, the machine readable media includes, without limitation, non-transient magnetic or optical media and random-access or read-only memory, including tapes, diskettes, hard disks, CD-ROMs and DVDs, flash memory cards or chips, servers and the internet. In another embodiment, the machine is a computer. The atomic coordinates may be used in a computer to generate a representation, e.g., an image, of the three-dimensional structure of the complex formed between a chemical compound discussed herein and DnaK and/or HSP70. The representation may be displayed by the computer and/or represented in an electronic file. The atomic coordinates and models derived therefrom may also be used for selection and X-ray crystallographic analysis of chemical compounds.

Accordingly, a computer for producing a three-dimensional representation of a DnaK-HSP70 inhibitor complex is provided. One of skill in the art would readily be able to select a suitable computer for use herein. In one embodiment, the computer contains a computer-readable data storage medium containing a data storage material encoded with computer-readable data, a working memory for storing instructions for processing the computer-readable data, a central-processing unit coupled to the working memory and to the computer-readable data storage medium for processing the computer-machine readable data into the three-dimensional representation; and a display coupled to the central-processing unit for displaying the three-dimensional representation. The data manipulated therein includes the structure coordinates of a $HIS_6$-IEGR-DnaK-PET-16 (referred to here as DnaK-PET-16) crystal and the structure coordinates of a crystal of the DnaK-HSP70 inhibitor.

Similarly, the machine-readable data storage medium may also be selected by one skilled in the art. In one embodiment, the machine-readable data storage medium contains a data storage material encoded with machine readable data. In another embodiment, the data is defined by at least a portion of the structure coordinates of $HIS_6$-IEGR-DnaK-PET-16 (referred to here as DnaK-PET-16) in Table 1.

The screening/design methods may be implemented in hardware or software, or a combination of both. In one embodiment, the programs and screening methods are implemented using computer programs executed on programmable computers each containing a processor, a data storage system, at least one input device, and at least one output device. Program code is applied to input data to perform the hereinabove described functions and generate output information. The output information is applied to one or more output devices. The computer may be, for example, a personal computer, microcomputer, or workstation of conventional design. Each such computer program may be stored on a storage medium or device, e.g., ROM or magnetic diskette, readable by a general or special purpose programmable computer.

In one embodiment, the HSP70 inhibitor physically and structurally associates with HSP70 or DnaK. In another embodiment, the HSP70 assumes a conformation that allows it to associate with HSP70 or DnaK. Although certain portions of the compound may not directly participate in the binding, those portions may influence the overall conformation of the molecule. Such conformational requirements include the overall three-dimensional structure and orientation of the chemical entity or compound in relation to all or a portion of the hydrophobic site or the spacing between functional groups of the chemical compound.

The crystal structures may be solved using programs and skill in the art. In one embodiment, the crystal structure is solved using molecular replacement optionally in combination with MAD (Multiwavelength Anomalous Dispersion) and/or MIRAS (Multiple Isomorphous Replacement with Anomalous Scattering), among others.

The structures may be then refined using computer software known in the art. In one embodiment, the computer software includes, without limitation, X-PLOR (Meth. Enzymol., vol. 114 & 115, Wyckoff et al., eds., Academic Press (1985)), MLPHARE (Collaborative computational project Number 4. The CCP4 Suite: Programs for Protein Crystallography (1994) Acta Crystallogr. D 50, 760-763) and SHARP (De La Fortelle, 1997, Methods Enzymol. 276: 472-494). The overall figure of merit may be improved by iterative solvent flattening, phase combination and phase extension with the program SOLOMON (Abrahams, 1996, ATPase, Acta Crystallogr. D 52: 110-119), among others.

A person skilled in the art may use one of several methods to screen test compounds for their ability to associate with DnaK or human HSP70 and more particularly with the hydrophobic pocket contained herein. This process may begin by visual inspection of, for example, the active site on the computer screen based on the three dimensional atomic coordinates of $HIS_6$-IEGR-DnaK-PET-16 (referred to here as DnaK-PET-16) complex. Selected chemical entities or test compounds may then be positioned in a variety of orientations. Docking may be accomplished using software such as Quanta and Sybyl. Such programs permit comparisons between different structures, different conformations of the same structure, and different parts of the same structure, followed by energy minimization and molecular dynamics with standard molecular mechanics force fields such as CHARMM and AMBER, among others.

Specialized computer programs may be utilized to select or screen chemical compounds. These include, without limitation, MCSS (Miranker, 1991, Proteins: Structure, Function and Genetics, 11: 29-34); GRID (Goodford, 1985, J. Med. Chem., 28: 849-857) DOCK (Kuntz, 1982, Journal of Molecular Biology, 161: 269-288), and AUTODOCK (Goodsell, 1990, Proteins: Structure. Function, and Genetics, 8: 195-202, among others.

Once suitable chemical compounds have been selected, they may be assembled into a single compound. Assembly may proceed by visual inspection of the relationship of the chemical compounds in relation to the three-dimensional atomic coordinates of the $HIS_6$-IEGR-DnaK-PET-16 (referred to here as DnaK-PET-16) structure. This may be followed by manual model building using software such as Quanta, Sybyl or O (Jones, 1991, Acta Crystallogr. A 47: 110-119). Refinement of the model may be carried out using CNS (Brunger, 1998, Acta Crystallogr. D 54: 905-921]. In addition, programs may be used to connect the individual chemical entities or test compounds. In one embodiment, these programs include, without limitation, 3D Database systems (Martin, 1992, J. Med. Chem., 35: 2145-2154) and CAVEAT (Bartlett, 1989, Royal Chem. Soc. 78:182-196).

Once a chemical compound is identified, the efficiency with which that entity or compound may bind to HSP70 or DnaK may be tested and optimized by computational evaluation. In one embodiment, an efficient HSP70 inhibitor has a dissociation constant ($K_d$) of about 2 to about 20 µM or integers or fractions there between, such as based on ITC studies.

Rather than build an HSP70 inhibitor one chemical entity at a time, other HSP70 inhibitors may be designed as a whole or de novo using either an empty binding site or optionally including some portion(s) of a known inhibitor(s). Such compounds may be designed using programs. In one embodiment, the program is a de novo program. In another embodiment, the program is LEGEND (Nishibata, 1991, Tetrahedron, 47:8985) and LUDI (Bohm, 1992, J. Comp. Aid. Molec. Design, 6:61-78).

The selected/designed compounds may then be tested for their binding efficiency to DnaK or HSP70 via computational evaluations using computer software. Such software may include, without limitation, QUANTA/CHARMM, Insight II/Discover, and/or MODELER. These types of programs may be implemented, e.g., using a workstation.

After selection/design of the HSP70 inhibitor, substitutions may be made among the L, M, and $R^1$-$R^5$ groups for improving or modifying binding properties. These substituted chemical compounds may then be analyzed for efficiency of binding to HSP70 by the same computer methods described above.

The crystals may be obtained using methods known to those skilled in the art of forming crystals. In one embodiment, the crystals are formed using methods of protein crystallization screens, e.g., automated protein crystallization screen maker system, high-throughput robotic protein crystallization system, or automated protein crystallization workstation, among others. In another embodiment, crystals are formed using vapor diffusion, e.g., hanging drop or sitting drop, microbatch, microdialysis, free-interface diffusion, or seeding, among others. Organic and inorganic solvents and protein crystallization additives are utilized optionally in the presence of a seed crystal or HSP70/DnaK-inhibitor protein mixture. In a further embodiment, the crystal is formed at temperatures below, at, or above room temperature. In still another embodiment, the crystals are formed using solutions containing one or both of ammonium sulfate or Bis-Tris. In yet a further embodiment, the crystal may be prepared using hanging-drop crystallization techniques at room temperature using about 1 µL protein and 1 µL of a solution containing about 1.8 M ammonium sulfate and 0.1 M Bis-Tris at a pH of 5.5.

Using such methods as described above and in the examples below, a co-crystal between $HIS_6$-IEGR-DnaK and PET-16 (referred to here as the DnaK-PET-16 structure) was generated and the three-dimensional crystal structure obtained. The co-crystal is a tetragonal crystal in space group $P4_32_12$ with a unit cell dimension of a=91.78, b=91.78 and c=136.89 (see FIGS. 8A-8C). As discussed above, a hydrophobic pocket was identified in this structure. This hydrophobic pocket contains several key points of contact between PET-16 and DnaK. In one embodiment, the hydrophobic pocket contains strand β1 of DnaK. In another embodiment, the strand β1 in the hydrophobic pocket contains amino acid residue L399 of SEQ ID NO: 4. In a further embodiment, the hydrophobic pocket contains loop LL,1 of DnaK. In still another embodiment, loop LL,1 of the hydrophobic pocket contains one or both of amino acid residue L392 or P396 of SEQ ID NO: 4. In yet another embodiment, the hydrophobic pocket contains loop L6,7 of DnaK. In a further embodiment, loop 6,7 of the hydrophobic pocket contains amino acid residue G482 of SEQ ID NO: 4. In yet a further embodiment, the hydrophobic pocket contains loop Lα,β. In another embodiment, loop Lα,β of the hydrophobic pocket contains one or both of amino acid residue A503 and S504 of SEQ ID NO: 4.

This hydrophobic pocket in the C-terminal SBD of DnaK corresponds to a hydrophobic pocket contained in HSP70. In one embodiment, the hydrophobic pocket in HSP70 contains strand β1. In another embodiment, the strand β1 in the hydrophobic pocket in HSP70 contains amino acid residue L401 of SEQ ID NO: 2. In a further embodiment, the hydrophobic pocket in HSP70 contains strand β7. In still another embodiment, strand β7 of the hydrophobic pocket in HSP70 contains amino acid residue G484 of SEQ ID NO: 2. In yet a further embodiment, the hydrophobic pocket in HSP70 contains loop LL,1. In still another embodiment, loop LL,1 of the hydrophobic pocket in HSP70 contains one or both of amino acid residue L394 or P398 of SEQ ID NO: 2. In yet a further embodiment, the hydrophobic pocket in HSP70 contains loop Lα,β. In another embodiment, loop Lα,β of the hydrophobic pocket in HSP70 contains one or both of amino acid residue N505 or D506 of SEQ ID NO: 2. In addition, see FIGS. 3A to 3F, FIGS. 4, 5 and S1-S5 of Leu et al, 2014, cited above, and incorporated by reference herein.

The chemical compounds described herein and those identified using the crystal and the methods described herein may be screened in assays. For example, the screening may be in vitro, in cell culture, and/or in vivo. Biological screening assays may be activity-based response models, binding assays, and/or bacterial, yeast and animal cell lines. Optionally, the assays are automated for high capacity-high throughput screening. Other assays include, without limitation, western blots, size exclusion chromatography, BIAcore biosensors, X-Ray absorption spectrometry, mass spectrometry, electron microscopy, nuclear magnetic resonance (NMR), fluorescence polarization, fluorescence anisotropy, circular dichroism, tryptophan fluorescence, isothermal titration calorimetry, pull-down assays and animal studies, among others.

D. Pharmaceutical Formulations and Methods of Administration

The compounds described herein or obtained via the screening methods or design methods described herein may be formulated as a pharmaceutical composition neat or with one or more excipient for administration. One of skill in the art would readily be able to determine suitable excipients based on the selected compound, patient, administration route, disease/condition being treated, among others. Not only may the composition be solid or liquid, but excipient(s) may be solid and/or liquid carriers. The carriers may be in dry or liquid form and must be pharmaceutically acceptable. The compositions are typically sterile solutions or suspensions.

Suitably, the compounds may be formulated for delivery to a patient by any suitable route including, e.g., transdermal, mucosal (intranasal, buccal, vaginal), oral, parenteral, intravenous, intratumoral, intranodal, among others. A variety of suitable delivery devices can be utilized for these delivery routes and include, without limitation, tablets, caplets, capsules, gel tabs, dispersible powders, granules, suspensions, injectable solutions, transdermal patches, topical creams or gels, and vaginal rings, among others.

In preparing the compositions described herein, the compounds may be combined with one or more excipients. Examples of excipients which may be combined with the compound include, without limitation, solid carriers, liquid carriers, adjuvants, amino acids (glycine, glutamine, asparagine, arginine, lysine), antioxidants (ascorbic acid, sodium sulfite or sodium hydrogen-sulfite), binders (gum tragacanth, acacia, starch, gelatin, polyglycolic acid, polylactic acid, poly-d,l-lactide/glycolide, polyoxaethylene, polyoxapropylene, polyacrylamides, polymaleic acid, polymaleic esters, polymaleic amides, polyacrylic acid, polyacrylic esters, polyvinylalcohols, polyvinylesters, polyvinylethers, polyvinylimidazole, polyvinylpyrrolidon, or chitosan), buffers (borate, bicarbonate, Tris-HCl, citrates, phosphates or other organic acids), bulking agents (mannitol or glycine), carbohydrates (such as glucose, mannose, or dextrins), clarifiers, coatings (gelatin, wax, shellac, sugar or other biological degradable polymers), coloring agents, complexing agents (caffeine, polyvinylpyrrolidone, β-cyclodextrin or hydroxypropyl-β-cyclodextrin), compression aids, diluents, disintegrants, dyes, emulsifiers, emollients, encapsulating materials, fillers, flavoring agents (peppermint or oil of wintergreen or fruit flavor), glidants, granulating agents, lubricants, metal chelators (ethylenediamine tetraacetic acid (EDTA)), osmo-regulators, pH adjustors, preservatives (benzalkonium chloride, benzoic acid, salicylic acid, thimerosal, phenethyl alcohol, methylparaben, propylparaben, chlorhexidine, sorbic acid, hydrogen peroxide, chlorobutanol, phenol or thimerosal), solubilizers, sorbents, stabilizers, sterilizer, suspending agent, sweeteners (mannitol, sorbitol, sucrose, glucose, mannose, dextrins, lactose or aspartame), surfactants, syrup, thickening agents, tonicity enhancing agents (sodium or potassium chloride) or viscosity regulators. See, the excipients in "Handbook of Pharmaceutical Excipients", 5$^{th}$ Edition, Eds.: Rowe, Sheskey, and Owen, APhA Publications (Washington, D.C.), 2005 and U.S. Pat. No. 7,078,053, which are incorporated herein by reference. The selection of the particular excipient is dependent on the nature of the compound selected and the particular form of administration desired.

Optional surfactants may include, without limitation, pluronics, PEG, sorbitan esters, polysorbates (polysorbate 20, polysorbate 80), triton, tromethamine, tyloxapal, lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids (1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid), taurocholic, acid, taurodeoxycholic acid, bile acids and their salts (cholic acid, deoxycholic acid and sodium glycocholates), sodium caprate, sodium laurate, sodium oleate, sodium lauryl sulfate, sodium cetyl sulfate, sulfated castor oil, sodium dioctylsulfosuccinate, cocamidopropylbetaine, laurylbetaine, fatty alcohols, cholesterols, glycerol mono- or -distearate, glycerol mono- or -dioleate and glycerol mono- or -dipalmitate, and polyoxyethylene stearate.

Optional adjuvants may include, without limitation, flavoring agents, coloring agents, preserving agents, and antioxidants, e.g., vitamin E, ascorbic acid, butylatedhydroxytoluene (BHT) and butylatedhydroxyanisole (BHA).

When the route of administration is oral, the composition may be any suitable conventional form, including, without limitation, the form of a capsule, caplet, gel tab, dispersible powder, granule, suspension, liquid, thin film, chewable tablet, rapid dissolve tablet, medical lollipop, or fast melt. In one embodiment, the composition is a liquid. In a further embodiment, the composition is a solid. In another embodiment, the composition is a suspension. One of skill in the art would readily be able to formulate the compositions discussed herein in any one of these forms.

Solid carriers include, without limitation, starch, lactose, dicalcium phosphate, microcrystalline cellulose, sucrose and kaolin, calcium carbonate, sodium carbonate, bicarbonate, lactose, calcium phosphate, gelatin, magnesium stearate, stearic acid, or talc.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier utilized in the injectable form may be a solvent or dispersion medium containing, e.g., water, ethanol (e.g., glycerol, propylene glycol and liquid polyethylene glycol), suitable mixtures thereof, and vegetable oil.

Liquid carriers may be utilized in preparing solutions, suspensions, emulsions, syrups and elixirs. In one embodiment, the compound is dissolved in a liquid carrier. In another embodiment, the compound is suspended in a liquid carrier. In one embodiment, the liquid carrier includes, without limitation, water, e.g., sterile water, Ringer's solution, isotonic sodium chloride solution, neutral buffered saline, saline mixed with serum albumin, organic solvents (such as ethanol, glycerol, propylene glycol, liquid polyethylene glycol, dimethylsulfoxide (DMSO)), oils (vegetable oils such as fractionated coconut oil, arachis oil, corn oil, peanut oil, and sesame oil; oily esters such as ethyl oleate and isopropyl myristate; and any bland fixed oil including synthetic mono- or diglycerides), fats, fatty acids (include, without limitation, oleic acid find use in the preparation of injectables), cellulose derivatives such as sodium carboxymethyl cellulose, surfactants, or artificial cerebrospinal fluid.

Such pharmaceutical preparations may contain, e.g., about 25, 30, 35, 40, 45, 50, 55, 60, 65, 70, 75, 80, 85, to about 90% of the compound in combination with the carrier.

The composition may also be utilized as an inhalant or aerosol. When administered as an inhalant, the composition may be in fluid unit doses using the compound and a vehicle for delivery by an atomizing spray pump or by dry powder for insufflation. When administered as an aerosol, the composition may be in a pressurized aerosol container together with a gaseous or liquefied propellant, e.g., dichlorodifluoromethane, carbon dioxide, nitrogen, propane, and the like. Also optionally provided is the delivery of a metered dose in one or more actuations. When the composition is administered intranasally, the administration may be performed using a mist or spray. In another embodiment, solutions can be nebulized.

The compounds may also be administered parenterally or intraperitoneally as solutions, suspensions, dispersions, or the like. As used herein, parenteral administration includes intravenous, intramuscular, subcutaneous, rectal, intraocular, intrasynovial, transepithelial including transdermal, ophthalmic, sublingual buccal, topical (dermal, ocular, rectal) and nasal inhalation (insufflation aerosol).

The compounds discussed herein may further be formulated to provide for the controlled or sustained release of the product which can then be delivered via a depot injection with an agent. In one embodiment, the compounds may be formulated with injectable microspheres, bio-erodible particles, polymeric compounds (polylactic or polyglycolic acid), beads, liposomes, or implantable drug delivery devices.

The compounds may also be administered via a vaginal ring or transdermal patch.

The pharmaceutical formulations discussed may be stored as a solution, suspension, gel, emulsion, solid, dehydrated solid, or lyophilized powder. Such formulations can be stored either in a ready-to-use form or in a form requiring reconstitution prior to administration. The formulations may also be contained with a container having a sterile access port, for example, an intravenous solution bag or vial having a stopper pierceable by a hypodermic injection needle.

D. Additional Pharmaceutical Reagents

One or more of the compounds discussed herein may be administered in combination with other pharmaceutical agents, as well as in combination with each other. The term "pharmaceutical" agent as used herein refers to a chemical compound which results in a pharmacological effect in a patient. A "pharmaceutical" agent can include any biological agent, chemical agent, or applied technology which results in a pharmacological effect in the subject.

In one embodiment, the compound is combined with one or more of these pharmaceutical agents, i.e., delivered to the patient concurrently. In another embodiment, the compound is administered to the patient concurrently therewith one or more of these pharmaceutical agents. In a further embodiment, the compound is administered prior to one or more of these pharmaceutical agents. In still another embodiment, the compound is administered subsequent to one or more of these pharmaceutical agents.

These pharmaceutical agents may be selected by one of skilled in the art and thereby utilized in combination with the compounds of formula (I). Examples of these additional agents include, without limitation, cytokines (interferon (α, β, γ) and interleukin-2), lymphokines, growth factors, antibiotics, bacteriostatics, enzymes (L-asparaginase), biological response modifiers (interferon-alpha; IL-2; G-CSF; and GM-CSF), differentiation agents (retinoic acid derivatives), radiosensitizers (metronidazole, misonidazole, desmethylmisonidazole, pimonidazole, etanidazole, nimorazole, RSU 1069, E09, RB 6145, SR4233, nicotinamide, 5-bromodeoxyuridine, 5-iododeoxyuridine, bromodeoxycytidine), hormones (adrenocorticosteroids, prednisone, dexamethasone, aminoglutethimide), progestins (hydroxyprogesterone caproate, medroxyprogesterone acetate, megestrol acetate), estrogens (diethylstilbestrol, ethynyl estradiol/equivalents), antiestrogens (tamoxifen), androgens (testosterone propionate, fluoxymesterone), antiandrogens (flutamide, gonadotropin-releasing hormone analogs, leuprolide), photosensitizers (hematoporphyrin derivatives, Photofrin®, benzoporphyrin derivatives, Npe6, tin etioporphyrin, pheoboride-α, bacteriochlorophyll-α, naphthalocyanines, phthalocyanines, and zinc phthalocyanines), proteosome inhibitors (bortezomib), tyrosine kinase inhibitors (imatinib mesylate, dasatinib, nilotinib, MK-0457, and Omacetaxine), immunotherapeutics, vaccines, biologically active agents, or HSP90 inhibitors.

The compositions described herein contain a compound of formula (I) as described above and a genotoxic agent. The term "genotoxic agent" as used herein refers to a chemical compound, environmental agent, and/or external stimulation which is damaging to DNA. In one embodiment, the genotoxic agent causes mutations in DNA. In a further embodiment, the genotoxic agent treats preferentially kills cancer over healthy cells of a patient. In another embodiment, the genotoxic agent enhances the effectiveness of a compound described herein.

In one embodiment, the genotoxic agent is a chemotherapeutic. Examples of chemotherapeutics which may be utilized as described herein include, without limitation cisplatin, 5-fluorouracil, cyclophosphamide, oncovin, vincristine, prednisone, or rituximab.

In a further embodiment, the genotoxic agent includes an HSP90 inhibitor. Examples of HSP90 inhibitors which may be utilized as described herein include, without limitation, a geldanamycin (GA)-derived mitochondrial matrix inhibitor, a Gamintrinib, Gamitrinib-G4, Gamitrinib-G3, Gamitrinib-G2, Gamitrinib-G1, Gamitrinib-TPP, and Gamitrinib-TPP-OH. See the HSP90 inhibitors described in International Patent Publication No. WO-2013/123151, which is incorporated by reference herein.

In another embodiment, the genotoxic agent is a BRAF inhibitor. Examples of BRAF inhibitor which may be utilized as described herein include, without limitation, sorafenib, vemurafenib, RAF-265 and XL281, PLX4032, dabrafenib, BMS-908662, LGX818, PLX3603, RO5185426, and GSK2118436.

In still a further embodiment, the genotoxic agent is a growth factor receptor inhibitor. Examples of growth factor receptor inhibitors which may be utilized as described herein include, without limitation, trastuzumab, pertuzumab, lapatinib, erlotinib, gefitinib, and Erbitux® antibody.

In yet another embodiment, the genotoxic agent is an immune checkpoint blockade inhibitor. Examples of immune checkpoint blockade inhibitors which may be utilized as described herein include, without limitation, an anti-PD1, PDL1, or CTLA4 immune checkpoint blockade inhibitor. In one embodiment, the immune checkpoint blockade inhibitor is ipilmumab.

In a further embodiment, the genotoxic agent is a proteasome inhibitor. Examples of proteasome inhibitors which may be utilized as described herein include, without limitation, bortezomib, carfilzomib, NPI-0052, MLN9708, CEP-18770, and ONX0912.

In one embodiment, the pharmaceutical composition contains a compound described herein and a chemotherapeutic. Alternatively, the compounds may be administered with a chemotherapeutic for treatment of the diseases described herein. One of skill in the art would readily be able to select a chemotherapeutic for formulations with or administration with one or more of the compounds based on the cancer being treated, patient physical condition, among others factors. In one embodiment, the chemotherapeutic is selected from among cisplatin, carboplatin, 5-fluorouracil, cyclophosphamide, oncovin, vincristine, prednisone, or rituximab, mechlorethamine, cyclophosphamide, ifosfamide, melphalan, chlorambucil, carmustine, lomustine, semustine, thriethylenemelamine, triethylene thiophosphoramide, hexamethylmelamine altretamine, busulfan, triazines dacarbazine, methotrexate, trimetrexate, fluorodeoxyuridine, gemcitabine, cytosine arabinoside, 5-azacytidine, 2,2'-difluorodeoxycytidine, 6-mercaptopurine, 6-thioguanine, azathioprine, 2'-deoxycoformycin, erythrohydroxynonyladenine, fludarabine phosphate, 2-chlorodeoxyadenosine, camptothecin, topotecan, irinotecan, paclitaxel, vinblastine, vincristine, vinorelbine, docetaxel, estramustine, estramustine phosphate, etoposide, teniposide, mitoxantrone, mitotane, or aminoglutethimide.

In another embodiment, the compound is formulated in a pharmaceutical composition with, or administered in a method for treating a disease with an antibiotic. Antibiotics may include, without limitation, actimomycin D, daunomycin (rubidomycin), doxorubicin (adriamycin), mitoxantrone, idarubicin, bleomycins, plicamycin (mithramycin), mitomycin C, dactinomycin, cephalosporins, aminoglycosidics, nitrofurans, vancomycin, monobactams, co-trimoxazole, metronidazole, carbacephem, carbapenems, glycopeptides, macrolides (azithromycin, clarithromycin, dirhromycin, erythromycin, roxithromycin, telithromycin), monobactams, penicillins, quinolones (fluoroquinolines), sulfonamides, tetracyclines, arsphenamine, chloramphenicol, clindamycin, lincomycin, ethambutol, fosfomycin, fusidic acid, furazolidone, isoniazid, linezolid, detronidazole, mupirocin, platensimycin, pyrazinamide, quinupristin/dalfopristin, rifampin/rifampicin, or tinidazole.

Another agent that may be formulated in a pharmaceutical composition with, or administered in a method of treating disease, with a compound described herein is a bacteriostatic agent. A bacteriostatic agent may be selected from among, without limitation, tetracyclines, sulphonamides, spectinomycins, trimethoprims, chloramphenicols, macrolides and lincosamide.

The compound may also be formulated or administered with a biologically active agent. In one embodiment, the biologically active agent is ribavirin, polymerase inhibitors, small interfering RNA compound, anti-sense oligonucleotide, nucleotide analog, nucleoside analog, immunoglobulin, hepatoprotectant, anti-inflammatory agent, antiviral, anti-infective compounds and biological agents useful for antibody mediated therapy. In another embodiment, the biologically active agent is cetuximab, trastuzumab, and Remicade™.

The compounds described herein may also be formulated with or co-administered in a method for treating disease with an HSP90 inhibitor and/or a heat treatment sufficient to induce a heat shock response. Examples of HSP90 inhibitors may include, without limitation, geldanamycin, radicicol, 17-AAG, KOS-953, 17-DMAG, CNF-101, CNF-1010, 17-AAG-nab, NCS-683664, Mycograb, CNF-2024, PU3, PU24FC1, VER49009, IPI-504, SNX-2112 and STA-9090.

Still other adjunctive therapies for use with the methods and compositions described herein include non-chemical therapies. In one embodiment, the adjunctive therapy includes, without limitation, radiation, acupuncture, surgery, chiropractic care, passive or active immunotherapy, X-ray therapy, ultrasound, diagnostic measurements, e.g., blood testing. In one embodiment, these therapies are be utilized to treat the patient. In another embodiment, these therapies are utilized to determine or monitor the progress of the disease, the course or status of the disease, relapse or any need for booster administrations of the compounds discussed herein.

One of skill in the art would be able to determine the amount of these pharmaceutical agents to administer in combination with a compound of formula (I). In one embodiment, lower doses of the compounds of formula (I) are required when administered in combination with an additional pharmacologically active reagent. In a further embodiment, the combination of the compound of formula (I) with another pharmacological agent or treatment protocol permits lower than usual dosages of the additional pharmacological agent to achieve the desired therapeutic effect. In another embodiment, the combination of the compound of formula (I) with another pharmacological agent or treatment protocol permits adjustment of the additional protocol regimen to achieve the desired therapeutic effect. In yet a further embodiment, the combination of the compound of formula (I) with another pharmacological agent or treatment protocol permits lower doses of the compounds to achieve the desired therapeutic effect.

E. Treatment Methods

In recognizing the need in the art for therapies for treating diseases mediated by HSP70, the inventors identified the small molecules discussed herein. The compounds of formula (I) unexpectedly bind to the C-terminal domain of HSP70 or the C-terminal domain of DnaK. In one embodiment, these compounds are useful in the treatment of neoplastic disease. The terms "neoplastic disease" and "cancer" are used interchangeably herein and refer to a disease or condition in which a patient has an abnormal mass of tissue due to an abnormal proliferation of cells. The abnormal proliferation of cells may result in a localized lump, be present in the lymphatic system, or may be systemic. In one embodiment, the neoplastic disease is benign. In another embodiment, the neoplastic disease is pre-malignant, i.e., potentially malignant neoplastic disease. In a further embodiment, the neoplastic disease is malignant, i.e., cancer. In one embodiment, the neoplastic disease includes, without limitation, epithelial cancer, Merkel cell carcinoma, liver cancer, cervical cancer, anal cancer, penile cancer, vulvar cancer, vaginal cancer, breast cancer, ovarian cancer, uterine cancer, skin cancer, melanoma, oral cancer, colon cancer, neck cancer, head cancer, eye cancer, Kaposi's sarcoma, leukemia, nasopharyngeal carcinoma, mesothelioma, bone cancer, brain cancer, prostate cancer, testicular cancer, pancreatic cancer, hepatocellular carcinoma, lung cancer, or lymphoma. In another embodiment, the neoplastic disease includes ovarian cancer, skin cancer, melanoma, oral cancer, or colon cancer. Still other HSP70-related neoplastic diseases are anticipated to respond to the methods and compositions described herein.

Advantageously, the compounds of formula (I) are selective to HSP70 containing cells and have low toxicity to non-transformed cells. The term "low toxicity" as used herein refers to an $IC_{50}$ of about 100 μM or integers or fractions less than 100 μM. These characteristics ensure that these compounds do not affect the healthy cells of the patient and permit more effective treatment. Further, the patient experiences considerably fewer side effects due to this selective cancer targeting regimen. This finding is integral in the treatment of certain cancers which are linked to HSP70 and for which there are no known small molecule drug therapies.

The inventors found that the compounds of formula (I) are highly selective in killing HSP70 containing cells alone or in combination with an additional pharmaceutical agent discussed above. In one embodiment, the compounds of formula (I) additively or synergistically function with the additional pharmaceutical agents in the methods described herein.

Accordingly, methods of inhibiting HSP70 or DnaK in a mammalian subject in need thereof are provided. Such subjects can be those suffering from a cancer referenced above. The methods are also useful in reducing HSP70 in mitochondria, which is advantageous since mitochondria are key factors in the regulation of cell death pathways of cancer cells.

These methods include administering a compound which co-crystallizes with HSP70 or DnaK to a subject in need thereof. In one embodiment, the compound contacts the hydrophobic pocket in HSP70 and binds to one or more amino acids in strand β1, strand β7, loop LL,1, and loop Lα,β of the SBDβ of human HSP70 as described above. In another embodiment, the compound contacts the hydrophobic pocket in HSP70 and binds to one or more amino acids in strand β1, loop LL,1, loop L6,7 and loop Lα,β of DnaK. In yet a further embodiment, the compound is a compound of formula (I) as described above.

Additional steps in the methods of treatment discussed may be performed. In one embodiment, the method also includes performing a competitive fluorescence polarization assay, nuclear magnetic resonance (NMR), isothermal titration calorimetry, pull-down assays, fluorescence anisotropy, circular dichroism or tryptophan fluorescence to test for binding of the HSP70 inhibitor to HSP70. In another embodiment, the method also includes computationally evaluating the structural fit of the HSP70 inhibitor in the hydrophobic pocket. In yet a further embodiment, the method further includes testing the HSP70 inhibitor for cell death in cancer cells using a growth inhibition assay that measure a cancer phenotype.

In yet another embodiment, the compounds may be utilized to impair cancer spread, or metastases. Methods of using the compounds for this purpose are described as are methods of designing and screening similarly functional compounds for this use.

The efficacy of the compounds discussed herein may be determined or estimated based on the corresponding $IC_{50}$ values. In one embodiment, a higher $IC_{50}$ correlates with a less potent compound. In another embodiment, a lower $IC_{50}$ correlates with a more potent compound. In a further embodiment, the compounds discussed herein have $IC_{50}$ values of about 5 µM or integers or fractions less than about 5 µM.

The effective dosage or amount of the compounds may vary depending on the particular compound employed, the mode of administration, the type and severity of the condition being treated, and subject being treated as determined by the subject's physician. In one embodiment, the effective amount is about 0.1 to about 50 mg/kg. In another embodiment, the effective amount is about 0.5 to about 40 mg/kg. In a further embodiment, the effective amount is about 0.7 to about 30 mg/kg. In still another embodiment, the effective amount is about 1 to about 20 mg/kg. In yet a further embodiment, the effective amount is about 0.001 mg/kg to 1000 mg/kg body weight. In another embodiment, the effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.25 mg/kg, about 0.1 mg/kg, about 100 µg/kg, about 75 µg/kg, about 50 µg/kg, about 25 µg/kg, about 10 µg/kg, or about 1 µg/kg. However, the effective amount of the compound can be determined by the attending physician and depends on the condition treated, the compound administered, the route of delivery, age, weight, severity of the patient's symptoms and response pattern of the patient.

The effective amount of the compound may be provided on regular schedule, i.e., daily, weekly, monthly, or yearly basis or on an irregular schedule with varying administration days, weeks, months, etc. Alternatively, the effective amount to be administered may vary. In one embodiment, the effective amount for the first dose is higher than the effective amount for one or more of the subsequent doses. In another embodiment, the effective amount for the first dose is lower than the effective amount for one or more of the subsequent doses. The number and frequency of dosages corresponding to a completed course of therapy will be determined according to the judgment of a health-care practitioner. The effective amounts described herein refer to total amounts administered for a given time period; that is, if more than one compound or a pharmaceutically acceptable salt thereof is administered, the effective amounts correspond to the total amount administered.

These dosage regimens may be adjusted to provide the optimal therapeutic response. For example, several divided doses of each component may be administered daily or the dose may be proportionally increased or reduced as indicated by the exigencies of the therapeutic situation. In one embodiment, the compounds or compositions discussed herein may be administered on a daily, monthly, or yearly basis. In one embodiment, daily administration is once. In another embodiment, daily administration includes divided units which are administered over the course of each day.

F. Screening Methods

To enable identification of new chemical entities or compositions that induce the EBV lytic cycle, the inventors developed a method for screening assay. Due to the need for improved efficacious therapeutics with lower toxicity and a decreased potential for recurrence of HSP70 related, this screening method may be performed for the high throughput screening of thousands of compounds.

The discovery of the hydrophobic pocket discussed above permits the screening of chemical compounds to identify potential HSP70 and/or DnaK inhibitors. Such a screening method includes first determining the three-dimensional structure of a complex containing a HSP70 inhibitor and DnaK by X-ray diffraction to produce atomic coordinates. A three dimensional model of this complex is generated utilizing thee atomic coordinates or portions thereof. The three dimensional model is then compared with a three dimensional model for a $HIS_6$-IEGR-DnaK-PET-16 (referred to here as DnaK-PET-16) complex as discussed above. In one embodiment, the three dimensional model for the complex is compared with the hydrophobic pocket in the three dimensional model for a DnaK-PET-16 complex. In another embodiment, the HSP70 inhibitor binds in the hydrophobic pocket in the three-dimensional structure of the complex.

The method optionally includes identifying a test compound as an inhibitor. In one embodiment, the identification is performed by detecting binding of the test compound within the hydrophobic pocket to one or more of amino acid residues L401, G484, N505, D506, L394, and P398 of SEQ ID NO: 2 (HSP70). In another embodiment, identification is performed by detecting binding of the test compound within the pocket to one or more of amino acid residues L399, L392, P396, G482, A503 and S504 of SEQ ID NO: 4 (DnaK).

G. Additional Treatment Protocols

The compounds and methods described herein may also be utilized for inhibiting or reducing bacterial growth in a subject in need thereof. The compounds and methods may also be utilized to design and use the same to inhibit the functions of DnaK in bacteria. The compounds are effective in reducing bacterial load of a variety of bacteria including, without limitation, *Escherichia coli*, *Salmonella*, *Staphylococcus aureus*, *Syphilis*, *Streptococcus pneumoniae*, *Tuberculosis*, or *Yersinia pseudotuberculosis*. In one embodiment, the bacterium is *E. coli*.

The phrase "inhibit bacterial growth" as used herein refers to preventing bacterial growth in or on a subject. Similarly, the phrase "reduce bacterial growth" as used herein refers to reducing or eliminating the bacterial load in or on a subject infected with a bacterium. Accordingly, the method may optionally include the administration of an antimicrobial and/or bacteriostatic agent set forth above.

H. Kits Containing The Compounds

Also provided are kits or packages of pharmaceutical formulations a compound of formula (I) optionally together with one or more additional reagent described above. Advantageously, for use in the kits, the compound is formulated for the desired delivery vehicle and route. In one embodiment, the kit is also includes a chemotherapeutic agent described above.

The kit may contain packaging or a container with the compound of formula (I). Optionally, the kit may further contain dosing instructions and/or an insert regarding the compound, instructions for monitoring circulating levels of the compound, and materials for performing such assays including, e.g., reagents, well plates, containers, markers, labels, applicators, needles, syringes, syringe, pipette, forcep, measuring spoon, eye dropper and other appropriate packaging and instructions for use. One of skill in the art would readily be able to select other components to include in the kits as determined by the delivery route. A number of packages or kits are known in the art and include, without limitation, labeled blister package, dial dispenser package, or bottle.

The compounds of formula (I) or compositions containing same can be a single dose or for continuous or periodic discontinuous administration, optionally administration instructions for a predetermined length of time or as prescribed and/or placebos during periods when the compound of formula (I) is not delivered.

In one embodiment, a kit is provided and contains a compound of formula (I) in a first dosing unit. The compound of formula (I) may be in the presence or absence of one or more of excipients or additional pharmaceutical agents described above in additional dosing units. In one embodiment, a second dosing unit is included and genotoxic agent.

I. Embodiments Described Herein

In one aspect, a compound of formula (I) of the following is provided or a pharmaceutically acceptable salt, prodrug, solvate, or metabolite thereof is provided. In this structure, L is absent or a noncleavable organic moiety. M is a ligand which promotes one or more of cellular uptake, delivery, or penetration of a small molecule through one or more of a cell wall, cell membrane, plasma membrane, or subcellular membrane. $R^1$ to $R^5$ are, independently, H, optionally substituted $C_1$ to $C_{10}$ alkyl, optionally substituted $C_1$ to $C_{10}$ alkenyl, optionally substituted $C_1$ to $C_{10}$ alkynyl, OH, halogen, $NH_2$, optionally substituted aryl, optionally substituted heteroaryl, optionally substituted heterocycle, optionally substituted $C_1$ to $C_{10}$ alkoxy, optionally substituted $C_1$ to $C_{10}$ hydroxyalkyl, optionally substituted aryloxy, optionally substituted heteroaryloxy, optionally substituted heterocycleoxy, optionally substituted $C_1$ to $C_{10}$ alkylthio, optionally substituted $C_1$ to $C_{10}$ alkylsulfonyl, optionally substituted $C_1$ to $C_{10}$ alkylcarbonylamino, optionally substituted alkylsulfonylamino, optionally substituted $C_1$ to $C_{10}$ alkylamino, optionally substituted $C_1$ to $C_{10}$ dialkylamino, optionally substituted arylamino, optionally substituted heteroarylamino, optionally substituted heterocycleamino, optionally substituted $C_1$ to $C_{10}$ amido, $NO_2$, optionally substituted $C_1$ to $C_{10}$ carboxy, optionally substituted $C_1$ to $C_{10}$ alkoxycarbonyl, optionally substituted $C_1$ to $C_{10}$ alkylcarbonyl, optionally substituted $C_1$ to $C_{10}$ alkylcarbonyloxy, optionally substituted alkylaminocarbonyl, optionally substituted arylaminocarbonyl, optionally substituted heteroarylaminocarbonyl, optionally substituted heterocycleaminocarbonyl, sulfamido or sulfonamide. When (i) L is absent, (ii) M is $PPh_3$ or $PPh_2CH_3$ and (iii) the compound is a bromide salt, not all of $R^1$ to $R^5$ are H.

(I)

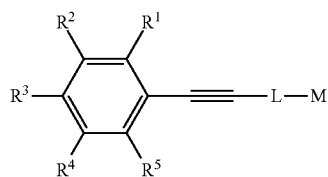

In one embodiment, M is an optionally substituted phosphine. In another embodiment, L is optionally substituted $C_1$ to $C_{10}$ alkyl, optionally substituted $C_1$ to $C_{10}$ alkenyl, optionally substituted $C_1$ to $C_{10}$ alkynyl, optionally substituted aryl, optionally substituted heteroaryl, optionally substituted heterocycle, optionally substituted $C_1$ to $C_{10}$ alkylsulfonyl, optionally substituted heteroarylamino, optionally substituted arylamino, optionally substituted heterocycleamino, optionally substituted $C_1$ to $C_{10}$ alkylcarbonylamino, optionally substituted alkylsulfonylamino, optionally substituted $C_1$ to $C_{10}$ alkylamino, optionally substituted $C_1$ to $C_{10}$ dialkylamino, optionally substituted $C_1$ to $C_{10}$ amido, optionally substituted $C_1$ to $C_{10}$ carboxy, optionally substituted $C_1$ to $C_{10}$ alkoxycarbonyl, optionally substituted $C_1$ to $C_{10}$ alkylcarbonyl, optionally substituted alkylaminocarbonyl, optionally substituted arylaminocarbonyl, optionally substituted heteroarylaminocarbonyl, optionally substituted heterocycleaminocarbonyl, sulfamido or sulfonamide. In a further embodiment, L is optionally substituted $C_1$ to $C_{10}$ alkyl. In yet another embodiment, L is $C_1$ to $C_6$ alkyl. In a further embodiment, M is optionally substituted triphenylphosphine. In still a further embodiment, M is triphenylphosphine. In another embodiment, M is of the following structure. In this embodiment, m, n, and p are, independently, 0 to 5. $R^6$, $R^7$, and $R^8$ are, independently, H, optionally substituted $C_1$ to $C_{10}$ alkyl, optionally substituted $C_1$ to $C_{10}$ alkenyl, optionally substituted $C_1$ to $C_{10}$ alkynyl, OH, halogen, $NH_2$, optionally substituted aryl, optionally substituted heteroaryl, optionally substituted heterocycle, optionally substituted $C_1$ to $C_{10}$ alkoxy, optionally substituted $C_1$ to $C_{10}$ hydroxyalkyl, optionally substituted aryloxy, optionally substituted heteroaryloxy, optionally substituted heterocycleoxy, optionally substituted $C_1$ to $C_{10}$ alkylthio, optionally substituted $C_1$ to $C_{10}$ alkylsulfonyl, optionally substituted $C_1$ to $C_{10}$ alkylcarbonylamino, optionally substituted alkylsulfonylamino, optionally substituted $C_1$ to $C_{10}$ alkylamino, optionally substituted $C_1$ to $C_{10}$ dialkylamino, optionally substituted arylamino, optionally substituted heteroarylamino, optionally substituted heterocycleamino, optionally substituted $C_1$ to $C_{10}$ amido, $NO_2$, optionally substituted $C_1$ to $C_{10}$ carboxy, optionally substituted $C_1$ to $C_{10}$ alkoxycarbonyl, optionally substituted $C_1$ to $C_{10}$ alkylcarbonyl, optionally substituted $C_1$ to $C_{10}$ alkylcarbonyloxy, optionally substituted alkylaminocarbonyl, optionally substituted arylaminocarbonyl, optionally substituted heteroarylaminocarbonyl, optionally substituted heterocycleaminocarbonyl, phosphate, sulfamido or sulfonamide.

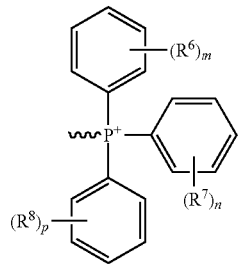

In another aspect, a compound of formula (II) is provided, wherein X is acetate, adipate, alginate, ammonium, ascorbate, aspartate, benzenesulfonate, benzoate, bicarbonate, bisulfate, borate, bromide, bromide chloride, butyrate, camsylate, camphorate, camphorsulfonate, caproate, chloride, citrate, dibromide, dichloride, digluconate, ethylenediamine, fluoride, formate, fumarate, gluconate, glutamate, glutarate, glycerolphosphate, halogen, 2-hydroxyethansulfonate, hemisulfate, heptanoate, hexanoate, iodide, lactate, laurate, maleate, malonate, malate, maleate, mesylate, myristyl methanesulfonate, mesitylenesulfonate, naphthylenesulfonate, napsylate, nicotinate, nitrate, oleate, oxalate, oxalate, palmitate, pamoate, pectinate, persulfate, 3-phenylpropionate, phosphate, picrate, pivalate, propionate, pyruvate, saccharinate, sebacate, stearate, succinate, sulfate, sulfonate, tartrate, tetrafluoroborate, trifluoromethyl sulfonate, tosylate, trichloroacetate, trifluoroacetate, p-toluenesulfonate, undecanoate, valerate, or xinafoate.

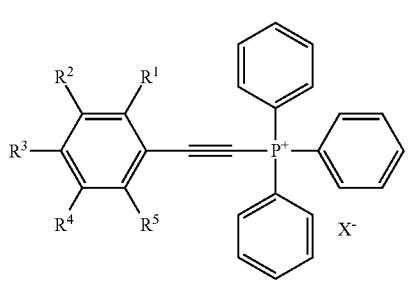

(II)

In a further aspect, a compound of formula (III) is provided, wherein q is 1 to 6 and X is acetate, adipate, alginate, ammonium, ascorbate, aspartate, benzenesulfonate, benzoate, bicarbonate, bisulfate, borate, bromide, bromide chloride, butyrate, camsylate, camphorate, camphorsulfonate, caproate, chloride, citrate, dibromide, dichloride, digluconate, ethylenediamine, fluoride, formate, fumarate, gluconate, glutamate, glutarate, glycerolphosphate, halogen, 2-hydroxyethansulfonate, hemisulfate, heptanoate, hexanoate, iodide, lactate, laurate, maleate, malonate, malate, maleate, mesylate, myristyl methanesulfonate, mesitylenesulfonate, naphthylenesulfonate, napsylate, nicotinate, nitrate, oleate, oxalate, oxylate, palmitate, pamoate, pectinate, persulfate, 3-phenylpropionate, phosphate, picrate, pivalate, propionate, pyruvate, saccharinate, sebacate, stearate, succinate, sulfate, sulfonate, tartrate, tetrafluoroborate, trifluoromethyl sulfonate, tosylate, trichloroacetate, trifluoroacetate, p-toluenesulfonate, undecanoate, valerate, or xinafoate.

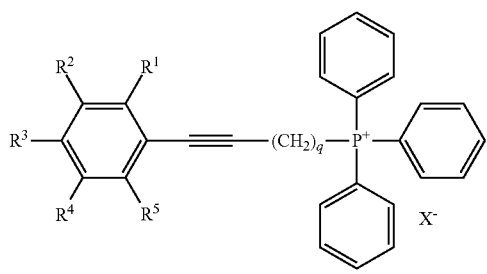

(III)

In still another aspect, the compound described herein is one of the following, wherein X is acetate, adipate, alginate, ammonium, ascorbate, aspartate, benzenesulfonate, benzoate, bicarbonate, bisulfate, borate, bromide, bromide chloride, butyrate, camsylate, camphorate, camphorsulfonate, caproate, chloride, citrate, dibromide, dichloride, digluconate, ethylenediamine, fluoride, formate, fumarate, gluconate, glutamate, glutarate, glycerolphosphate, halogen, 2-hydroxyethansulfonate, hemisulfate, heptanoate, hexanoate, iodide, lactate, laurate, maleate, malonate, malate, maleate, mesylate, myristyl methanesulfonate, mesitylenesulfonate, naphthylenesulfonate, napsylate, nicotinate, nitrate, oleate, oxalate, oxylate, palmitate, pamoate, pectinate, persulfate, 3-phenylpropionate, phosphate, picrate, pivalate, propionate, pyruvate, saccharinate, sebacate, stearate, succinate, sulfate, sulfonate, tartrate, tetrafluoroborate, trifluoromethyl sulfonate, tosylate, trichloroacetate, trifluoroacetate, p-toluenesulfonate, undecanoate, valerate, or xinafoate.

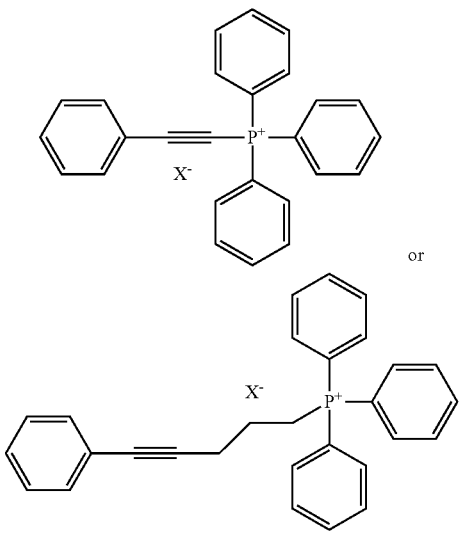

or

In yet a further aspect, a composition is provided and contains a genotoxic agent and a compound of formula (I) or a pharmaceutically acceptable salt, prodrug, solvate, or metabolite thereof. In this structure, L is absent or a non-cleavable organic moiety. M is a ligand which promotes one or more of cellular uptake, delivery, or penetration of a small molecule through one or more of a cell wall, cell membrane, plasma membrane, or subcellular membrane. $R^1$ to $R^5$ are, independently, H, optionally substituted $C_1$ to $C_{10}$ alkyl, optionally substituted $C_1$ to $C_{10}$ alkenyl, optionally substituted $C_1$ to $C_{10}$ alkynyl, OH, halogen, $NH_2$, optionally substituted aryl, optionally substituted heteroaryl, optionally substituted heterocycle, optionally substituted $C_1$ to $C_{10}$ alkoxy, optionally substituted $C_1$ to $C_{10}$ hydroxyalkyl, optionally substituted aryloxy, optionally substituted heteroaryloxy, optionally substituted heterocycleoxy, optionally substituted $C_1$ to $C_{10}$ alkylthio, optionally substituted $C_1$ to $C_{10}$ alkylsulfonyl, optionally substituted arylamino, optionally substituted heteroarylamino, optionally substituted heterocycleamino, optionally substituted $C_1$ to $C_{10}$ alkylcarbonylamino, optionally substituted alkylsulfonylamino, optionally substituted $C_1$ to $C_{10}$ alkylamino, optionally substituted $C_1$ to $C_{10}$ dialkylamino, optionally substituted $C_1$ to $C_{10}$ amido, $NO_2$, optionally substituted $C_1$ to $C_{10}$ carboxy, optionally substituted $C_1$ to $C_{10}$ alkoxycarbonyl, optionally substituted $C_1$ to $C_{10}$ alkylcarbonyl, optionally substituted $C_1$ to $C_{10}$ alkylcarbonyloxy, optionally substituted alkylaminocarbonyl, optionally substituted arylaminocarbonyl, optionally substituted heteroarylaminocarbonyl, optionally substituted heterocycleaminocarbonyl, phosphate, sulfamido or sulfonamide.

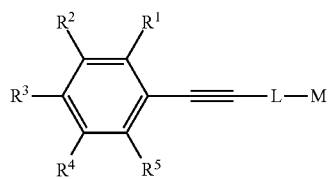

(I)

In still another aspect, a method of inhibiting HSP70 or DnaK is provided and includes administering a compound which co-crystallizes with HSP70 or DnaK to a subject in need thereof. In one embodiment, the compound has the structure of formula (I).

In a further aspect, a method of reducing HSP70 in mitochondria of a cancer cell is provided and includes administering a compound which co-crystallizes with HSP70 or DnaK to a subject in need thereof. In one embodiment, the compound has the structure of formula (I).

In another aspect, a method of treating malignant neoplastic disease is provided and includes administering a compound which co-crystallizes with HSP70 or DnaK to a subject in need thereof. In one embodiment, the compound has the structure of formula (I). In another embodiment, the malignant neoplastic disease is epithelial cancer, Merkel cell carcinoma, liver cancer, cervical cancer, anal cancer, penile cancer, vulvar cancer, vaginal cancer, breast cancer, ovarian cancer, uterine cancer, skin cancer, melanoma, oral cancer, colon cancer, neck cancer, head cancer, eye cancer, Kaposi's sarcoma, leukemia, nasopharyngeal carcinoma, mesothelioma, bone cancer, brain cancer, prostate cancer, testicular cancer, pancreatic cancer, hepatocellular carcinoma, lung cancer, or lymphoma.

In still a further aspect, a method of inhibiting or reducing bacterial growth is provided and includes administering a compound which co-crystallizes with HSP70 or DnaK to a subject in need thereof. In one embodiment, the compound has the structure of formula (I). In another embodiment, the bacterium is *Escherichia coli, Salmonella, Staphylococcus aureus, Syphilis, Streptococcus pneumoniae, Tuberculosis*, or *Yersinia pseudotuberculosis*. In a further embodiment, the method further includes administering a genotoxic agent.

In yet another aspect, a method for screening for a HSP70 inhibitor or DnaK inhibitor is provided and includes (a) determining the three-dimensional structure of a complex of a HSP70 inhibitor and DnaK by X-ray diffraction to produce atomic coordinates, (b) constructing a three dimensional model of the complex utilizing the atomic coordinates or portions thereof, and (c) comparing the three dimensional model with a three dimensional model for a $HIS_6$-IEGR-DnaK-PET-16 (referred to here as DnaK-PET-16) complex, wherein the DnaK-PET-16 complex contains a hydrophobic pocket and wherein the HSP70 inhibitor binds in the hydrophobic pocket in the three-dimensional structure of the complex. In one embodiment, the method further includes (d) identifying a test compound as an inhibitor by detecting binding of the test compound within the pocket to one or more of amino acid residues L401, G484, N505, D506, L394, and P398 of SEQ ID NO: 2 (HSP70). In another embodiment, the method further includes (e) identifying a test compound as an inhibitor by detecting binding of the test compound within the pocket to one or more amino acid residues L399, L392, P396, G482, A503 and S504 of SEQ ID NO: 4 (DnaK).

In a further aspect, a method for inhibiting HSP70 is provided, wherein HSP70 contains a hydrophobic pocket formed by residues in strand β1, strand β7, loop LL,1, and loop Lα,β of the substrate-binding domain β of human HSP70. The method includes contacting the hydrophobic pocket with a ligand which binds to strand β1, strand β7, loop LL,1, and loop Lα,β of the substrate-binding domain β of human HSP70 of the hydrophobic pocket. In one embodiment, the hydrophobic pocket is formed by amino acid residues in strand β1, strand β7, loop LL,1, and loop Lα,β of the substrate-binding domain β of human HSP70 of SEQ ID NO: 2. In another embodiment, the residue in strand β1 contains L401 of SEQ ID NO: 2, the residue in strand β7 contains G484 of SEQ ID NO: 2, the residue in loop LL,1 contains one or both of L394 or P398 of SEQ ID NO: 2, the residue in loop Lα,β contains one or both of N505 or D506 of SEQ ID NO: 2, or combinations thereof. In a further embodiment, the hydrophobic pocket is formed by amino acid residues in strand β1, loop LL,1, loop L6,7 and loop Lα,β of the DnaK-PET-16 complex. In still another embodiment, the residue in strand β1 contains L399 of SEQ ID NO: 4, the residue in loop LL,1 contains one or both of L392 or P396 of SEQ ID NO: 4, the residue in loop L6,7 contains G482 of SEQ ID NO: 4, the residue in loop Lα,β contains one or both of A503 and S504 of SEQ ID NO: 4, or combinations thereof. In yet another embodiment, the method further includes (d) performing a competitive fluorescence polarization assay, nuclear magnetic resonance (NMR), isothermal titration calorimetry, fluorescence anisotropy, circular dichroism, tryptophan fluorescence or pull-down assays to test for binding of the HSP70 inhibitor to HSP70. In a further embodiment, the method includes (e) computationally evaluating the structural fit of the HSP70 inhibitor in the hydrophobic pocket. In another embodiment, the method includes (f) testing the HSP70 inhibitor for cell death in cancer cells using a growth inhibition assay that measure a cancer phenotype.

In still another aspect, a computer for producing a three-dimensional representation of a DnaK-HSP70 inhibitor complex is provided and contains (a) a computer-readable data storage medium containing a data storage material encoded with computer-readable data containing (i) the structure coordinates of a DnaK-PET-16 crystal and (ii) the structure coordinates of a crystal of the DnaK-HSP70 inhibitor, (b) a working memory for storing instructions for processing the computer-readable data, (c) a central-processing unit coupled to the working memory and to the computer-readable data storage medium for processing the computer-machine readable data into the three-dimensional representation, and (d) a display coupled to the central-processing unit for displaying the three-dimensional representation.

In still another aspect, a machine-readable data storage medium is provided and contains a data storage material encoded with machine readable data, wherein the data is defined by at least a portion of the structure coordinates of the $HIS_6$-IEGR-DnaK-PET-16 (referred to here as DnaK-PET-16) structure in Table 1.

In a further aspect, a three-dimensional structure of a hydrophobic pocket in HSP70 is provided and includes (i) strand β1 containing amino acid residue L401 of SEQ ID NO: 2, (ii) strand β7 containing amino acid residue G484 of SEQ ID NO: 2, (iii) loop LL,1 containing one or both of amino acid residues L394 or P398 of SEQ ID NO: 2, and (iv) loop Lα,β containing one or both of amino acid residues N505 or D506 of SEQ ID NO: 2.

In yet another aspect, a three-dimensional structure of a hydrophobic pocket in DnaK is provided and includes (i) strand β1 containing amino acid residue L399 of SEQ ID NO: 4, (ii) loop LL,1 containing one or both of amino acid residues L392 or P396 of SEQ ID NO: 4, (iii) loop L6,7 containing amino acid residue G482 of SEQ ID NO: 4, and (iv) loop Lα,β containing one or both of amino acid residues A503 and S504 of SEQ ID NO: 4.

K. Examples (i) Reagents and Antibodies

The primary and secondary antibodies were described in Leu 2009 and Leu 2011. Sulfo-NHS-SS-Biotin (Biotin) and PES (2-Phenylethynesulfonamide or Pifithrin-µ) were purchased from Pierce Biotechnology, Inc. (Rockford, Ill.) and EMD Millipore Chemicals, Inc. (Billerica, Mass.), respectively. The HSP70 antibodies used for the affinity purification studies were from Enzo Life Sciences, Inc. (Farmingdale, N.Y., USA). The other antibodies were obtained from Cell Signaling Technology, Inc. (Danvers, Mass., USA).

(ii) Immunoblotting, Immunoprecipitation, B-PES Pull-Down Assays, Mass Spectrometry and Electron Microscopy Western blotting, immunoprecipitations and B-PES pull down assays were performed as described in Leu 2009 and Leu 2011. Preparation of biotin-conjugated PES was described in Leu 2009 and Leu 2011; Balaburski, 2013. Liquid chromatography-tandem mass spectrometry was performed by the Genomics Institute and Abramson Cancer Center Proteomics Core Facility at the Perelman School of Medicine, University of Pennsylvania. Electron microscopy (EM) and EM imaging were performed by The Electron Microscopy Resource Laboratory, Biomedical Research Core Facilities, at the Perelman School of Medicine, University of Pennsylvania.

(iii) Plasmids and Proteins

The human stress-inducible HSP70 (residues 1-641 or 386-616 of SEQ ID NO: 2) and E. coli DnaK (residues 1-638, 389-607, or 393-507 of SEQ ID NO: 4) were cloned into the pET25 vector (EMD Millipore Chemicals, Inc., Billerica, Mass., USA) between the NdeI and XhoI restriction sites. The full-length HSP70 and DnaK mutants were constructed by PCR-based site-directed mutagenesis using the QuikChange™ Site-Directed Mutagenesis Kit (Agilent Technologies, Inc., Santa Clara, Calif., USA). All plasmid inserts were verified by DNA sequencing. All HSP70 and DnaK variants were produced with a N-terminal $His_6$-tag in the E. coli BL21 Star (DE3) strain (Invitrogen catalog number C6010-03). The resulting strains were grown at 37° C. in LB medium containing 50 µg/mL of carbenicillin (Sigma-Aldrich Co., St. Louis, Mo., USA). At an $OD_{600}$ about 0.3 to about 0.5, protein expression was induced with 0.5 mM isopropyl-β-D-thiogalactopyranoside (IPTG), and cells were subsequently grown at 25° C. for about 16 h. Cells were collected by centrifugation and resuspended in the Bugbuster® Master Mix (EMD Millipore Chemicals catalog number 71456-4), supplemented with protease inhibitors, 1 mM diethiothreitol (DTT) and 20 mM imidazole. The $His_6$-tagged fusion proteins were isolated on $Ni^{2+}$-chelating resins (Ni-NTA Superflow, Qiagen catalog number 30410) by standard procedures. When necessary, size-exclusion chromatography on a Superdex® 200 or a Superose® 6 10/300 GL columns (GE Healthcare) analytical column pre-equilibrated with 1× Dulbecco's Phosphate Buffered Saline (DPBS—Invitrogen 14190-136), 1 mM Tris-HCl (pH 7.4) or 10 mM Tris-HCl (pH 7) was used as the final purification step. The purified DnaK proteins were dialyzed thoroughly against 1× DPBS with 5 mM DTT at 4° C., for crystallization trials involving the small molecule inhibitor PET-16. For isothermal titration calorimetry studies, all HSP70 and DnaK variants were dialyzed extensively against the buffers as noted below under the section entitled "Isothermal Titration calorimetry Studies". The dialyzed proteins were subsequently microcentrifuged at 15,000×g for 5 min at 4° C. and aliquots of the soluble proteins were stored at −80° C.

The parental HSP70 construct was purchased from the OriGene Technologies, Inc. catalog # SC116766. The parental DnaK construct was a published construct generated by Dr. Lila Gierasch (University of Massachusetts Amherst). However, the recombinant proteins derived from both parental constructs failed to co-crystallize with PET-16. Both DnaK and HSP70 constructs were genetically manipulated/ modified to facilitate co-crystallization. The exogenous residues are underlined. Notably, co-crystals of DnaK-PET-16 were obtained using the purified $HIS_6$-IEGR-DnaK (residues 389-607) protein (SEQ ID NO: 5). In contrast, both DnaK (residues 389-607) protein as well as $HIS_6$-IE-DnaK (residues 389-607) protein failed to co-crystallize with PET-16 (sequence not shown). Co-crystals of substrate bound HSP70 were obtained using the $HIS_6$-HSP70 (residues 386-616) protein (SEQ ID NO: 6), but not HSP70 (residues 386-616) protein and $HIS_6$-HSP70 (residues 391-615) protein. All plasmid inserts were verified by DNA sequencing at the DNA Sequencing Facility, Perelman School of Medicine at the University of Pennsylvania. The predicted protein sequences were confirmed by comparison to protein sequences in the NCBI website (http://blast.ncbi.nlm.nih-.gov/Blast.cgi). The PET-16 contacting residues are highlighted in grey. The residues that were added to facilitate co-crystallization are underlined.

HIS6-IEGR-DnaK (residues 389-607)
(SEQ ID NO: 5)
MHHHHHHIEGRVLLLDVTPLSLGIETMGGVMTTLIAKNTTIPTKHSQVFST

AEDNQSAVTIHVLQGERKRAADNKSLGQFNLDGINPAPRGMPQIEVTFDID

ADGILHVSAKDKNSGKEQKITIKASSGLNEDEIQKMVRDAEANAEADRKFE

ELVQTRNQGDHLLHSTRKQVEEAGDKLPADDKTAIESALTALETALKGEDK

AAIEAKMQELAQVSQKLMEIAQQQHA

HIS6-HSP70 (residues 386-616)
(SEQ ID NO: 6)
MHHHHHHENVQDLLLLDVAPLSLGLETAGGVMTALIKRNSTIPTKQTQIFT

TYSDNQPGVLIQVYEGERAMTKDNNLLGRFELSGIPPAPRGVPQIEVTFDI

DANGILNVTATDKSTGKANKITITNDKGRLSKEEIERMVQEAEKYKAEDEV

QRERVSAKNALESYAFNMKSAVEDEGLKGKISEADKKKVLDKCQEVISWLD

ANTLAEKDEFEHKRKELEQVCNPIISGLYQGAGG (iv) Protein Crystallization and Structure Determination Crystals of HIS6-IEGR-DnaK-PET-16 (referred to here as DnaK-PET-16) were prepared by mixing 400 µM of HIS6-IEGR-DnaK (residues 389-607 of SEQ ID NO: 5) with 4 mM PET-16. The protein mixtures were preheated to 42° C. for 15 minutes and gradually cooled to room temperature. The protein preparations were microcentrifuged at 15,000×g for 5 min at room temperature, and the soluble protein complexes were subjected to the crystallization screening using the hanging-drop vapor diffusion method. The drops were set up with 1 µL protein plus 1 µL reservoir solution at room temperature.

Crystals of HIS6-IEGR-DnaK grown in the presence of PET-16 were obtained from a solution of 1.8 M ammonium sulfate and 0.1 M Bis-Tris, pH 5.5 at room temperature. The HIS6-IEGR-DnaK-PET-16 (referred to here as DnaK-PET- 16) crystals were harvested into the reservoir solution with the addition of glycerol (25% v/v) and flash-frozen in liquid nitrogen.

All diffraction data sets were collected at the National Synchrotron Light Source (Brookhaven National Laboratory) and processed with HKL® 2000 software. The HIS$_6$-IEGR-DnaK-PET-16 (referred to hereafter as DnaK-PET-16) data sets were collected on the Beamline™ X25 instrument. The crystal structures were determined by molecular replacement with Phaser® program, using the structure of DnaK-NRLLLTG (PDB code 1DKY) as a search model, with the NRLLLTG peptide (SEQ ID NO: 7) extracted from the search model. The structures of the proteins were refined and manually adjusted using the high resolution native dataset by iterative cycles of refinement with Phenix.refine® (Afonine, 2012), and model building was performed using the Crystallographic Object-Oriented Toolkit program (COOT—Emsley and Cowtan, 2004). The PET-16 ligand was modeled into the corresponding electron density maps after refinement of the protein had converged. The final model, and the modeled PET-16 inhibitor, was checked for errors with a composite omit map generated by AutoBuild in the Phenix® suite (Adams, 2010). Data collection and refinement statistics are shown in Table 1. All the structural figures were prepared using PyMOL (http://www.pymol.org/) (Delano, 2002).

TABLE 1

Data Collection and Refinement Statistics of the Crystallographic DnaK-PET-16 Structure

| Data Collection | |
|---|---|
| Space group | P4$_3$2$_1$2 |
| Cell dimensions | |
| a, b, c (Å) | 91.78, 91.78, 136.89 |
| α, β, γ (°) | 90.00, 90.00, 90.00 |
| Wavelength | 1.1 |
| Resolution (Å) | 45-3.45 (3.57-3.45) |
| R$_{merge}$ | 9.9 (49.0) |
| I/σ (I) | 15.0 (2.5) |
| Data completeness (%) | 99.7 (99.9) |
| Redundancy | 5.0 (5.3) |
| No. reflections | 8281 |
| Refinement Statistics | |
| Resolution (Å) | 45-3.45 (3.57-3.45) |
| No. reflections | 8148 |
| R$_{work}$/R$_{free}$ | 28.43/32.82 |
| No. atoms | 2831 |
| Protein | 2803 |
| Ligand/ion | 27 |
| Water | 1 |
| Average B-factor (Å$^2$) | 43.46 |
| r.m.s deviations | |
| Bond lengths (Å) | 0.0045 |
| Bond angles (°) | 1.081 | r.m.s., root-mean-square deviation. Values in parentheses are for the highest resolution shell.

(vi) Isothermal Titration Calorimetry Studies

All ITC experiments were performed using a MicroCal VP-ITC isothermal titration calorimeter (MicroCal). Both full-length HSP70 and DnaK proteins and DnaK (aa 393-507) proteins were prepared in 1 mM Tris-HCl (pH 7.4) buffer containing 3% dimethylsulfoxide (DMSO). The HSP70 (aa 386-616) protein was prepared in buffer containing 3% DMSO and 10 mM Tris-HCl, pH 7. The syringe was loaded with purified protein in either 1 mM Tris-HCl (pH 7.4) buffer containing 3% DMSO or 10 mM Tris-HCl (pH 7) buffer containing 3% DMSO. The sample cell of the calorimeter was loaded with PES, PET-16 or NRLLLTG (SEQ ID NO: 7) prepared in the same buffer. All solutions were degassed for 5 min.

The titrations involving the full-length purified proteins were performed at 25° C. with injection volumes of 12 μL and a spacing of 300 s. The titrations involving the purified HSP70 (aa 386-616) and DnaK (aa 393-507) were performed at 42° C. with injection volumes of 12 μL and a spacing of 300 s. Heat from the pre-injection was not used during fitting. The data were fit using a one-site binding model available in the Origin® ITC data analysis software (MicroCal Origin® V5.0, MicroCal Software, Northampton, Mass.). Error values obtained from the MicroCal Origin® V5.0 software were averaged and reported.

Example 1

Identification of an Effective New Small Molecule Inhibitor of Mammalian HSP70 and Bacterial DnaK Using structure-activity relationship assays, an initial small scale screen of related compounds that contain one or more moieties in common with PES/PES-Cl (FIG. 1D) was performed. This approach was informative, and pointed to the phenyl group (aromatic moiety) and acetylene linker as key features for the biological activity of these molecules (FIG. 1A).

This approach was validated and resulted in the design of two analogs that interact with HSP70. Both of these compounds exhibit cytotoxicity values in the very low μM range. One such molecule is triphenyl(phenylethynyl)phosphonium bromide ($C_{26}H_{20}BrP$; MW 443.327) referred to as PET-16 (FIG. 1E). PET-16 contains a phenyl group, an acetylene linker and a triphenylphosphine moiety (TPP). To date, no compounds containing the TPP substituent have been reported to bind selectively and directly to DnaK and HSP70.

Based on the X-ray structure of DnaK-PET-16, two new analogs were designed, synthesized and characterized. These compounds are PET-3C (FIG. 1F), which is able to bind to HSP70; and PET-DR (FIG. 1G), which is negative for this ability.

Example 2

Cell Viability Analysis Confirms that PET-16 is Preferentially Cytotoxic to Tumor Cells of Diverse Origin It was found that concentrations of PET-16 that inhibit the viability of a broad range of tumor cell lines have little effect on non-transformed cells, such as fibroblasts or primary melanocytes (FIGS. 2A and 2B). For example, the IC$_{50}$ for PET-16 in several of the melanoma cell lines examined was about 0.5-1.5 μM (FIG. 2A). In addition, because bacteria rely on a functional DnaK system to survive stresses such as elevated temperatures, the effects of PET-16 on E. coli were tested. It was found that this small molecule impaired bacterial growth (FIGS. 2C and 2D); it also caused cell filamentation and reduced viability, a phenotype that is identical to that of many DnaK mutants. In contrast, the TPP moiety alone had little discernible effect on the viability of mammalian tumor cells (FIG. 2B) and had no negative effect on the growth of E. coli (FIG. 2D).

Example 3

PET-16 Directly Binds to a C-Terminal Region of HSP70 and of DnaK

To assess whether there was a direct molecular interaction between PET-16 and HSP70/DnaK, isothermal titration calorimetry (ITC) was employed. Full-length recombinant proteins of HSP70 (aa 1-641) as well as DnaK (aa 1-638) were pretreated either with ADP or ATP, to assess the interaction of PET-16 with different nucleotide-bound states of the protein. In addition to PET-16, PES and a well-studied, synthesized client protein peptide (NRLLLTG—SEQ ID NO: 7) of HSP70/DnaK, previously shown to complex with a defined canonical substrate binding pocket of the SBD were also assayed. See, Bertelsen, "Solution Confirmation of wild-type E. coli HSP70 (DnaK) Chaperone Complexed with ADP and Substrate", PNAS, 106(21): 8471-8476 (May 26, 2009) and incorporated by reference herein.

ITC analyses revealed that the peptide and the two small molecules PES and PET-16 exhibit a strong preference for the ADP-bound forms of HSP70, with $K_d$ values of about 10 µM, 5.7 µM and 3.8 µM, respectively, (FIGS. 3A-C). Similarly, the interactions of PES and PET-16 with the ADP-bound form of DnaK were determined to be about 6.8 µM and about 6 µM, respectively, (FIGS. 3D and 3E). In contrast, the interaction of the compounds PES and PET-16 with the ATP-bound versions of HSP70 or DnaK was notably reduced (FIGS. 3F-H). These data support a model that PET-16 behaves as allosteric modulators that preferentially target the ADP-bound conformation of HSP70/DnaK.

ITC binding curves also indicate that one PET-16 molecule binds in a complex containing two molecules of ADP-bound HSP70/DnaK (FIGS. 3C and 3E). PET-16 also binds to the C-terminal domain of HSP70 (residue 386-616), exhibiting a $K_d$ of about 2.9 µM (FIG. 3I). In contrast, the TPP moiety alone does not bind to either HSP70 or DnaK SBD (FIG. 3J).

Upon performing the ITC analysis, it was discovered that pre-incubation of HSP70 with PES markedly reduced the binding affinity of protein for PET-16 (FIG. 3K). In the converse situation, pre-saturation of HSP70 with PET-16 also impaired the interaction of protein with PES. These data are most consistent with the premise that these chemically related compounds bind to the same site of the HSP70 protein. To further assess this possibility in vivo, biotin-tagged PES (B-PES, FIG. 1B) was employed in a pull-down assay. In this assay, cultured tumor cells were pretreated with PET-16 for 1 h prior to the addition of B-PES. B-PES-containing complexes were then captured using Avidin beads and then examined for the presence of HSP70 by immunoblotting. It was found that pretreating cells with PET-16 clearly reduced the amount of HSP70 found in complex with B-PES (FIG. 3L); these results are consistent with the ITC data (FIG. 3K), suggesting that the two compounds likely target the same binding site.

Example 4

PET-16 Impairs Protein Quality Control

Using a number of approaches, it was confirmed that binding of PET-16 to HSP70 would impair proteostasis, as expected for an HSP70 inhibitor. As one example, electron microscopy analysis (EM) of cells treated with this compound provides evidence of altered autophagy and impaired proteostasis (FIG. 4A). The evidence includes (i) the appearance of multiple single- and double-membrane structures indicative of altered autophagy (ii) an accumulation of multiple vacuoles, (iii) the appearance of granular and aggregated masses within vacuoles and throughout the cell, and (iv) loss of membrane structures and mitochondria. In addition, western blot analysis revealed an increase in the appearance of the autophagy marker, processed LC3II, following treatment of cells with PET-16 (FIGS. 4B and 4C).

This data also demonstrates that treating cells with PET-16 also leads to reduced interactions between HSP70 and many client/substrate proteins. This is illustrated by immunoprecipitation-western blot (IP-WB) analysis; here whole cell lysates were immunoprecipitated with antibody to HSP70, and co-precipitating proteins visualized by Coomassie staining It is evident that PET-16 treatment results in loss of interactions between HSP70 and many polypeptides (FIGS. 4D and 4E).

An inhibition of the chaperone functions of HSP70 by PET-16 is expected to alter the localization and/or stability of many client proteins, promoting functional inactivation. For example, mutations in the BRAF protein kinase frequently occur in tumors such as melanoma. The mutant form of this protein is an HSP70 client protein. It was demonstrated by western blot analysis that protein samples from PET-16 treated melanoma tumor cells exhibit a reduction in expression of BRAF(V600E) protein abundance in the soluble fraction; this was accompanied by a notable increase of the protein in the detergent-insoluble fraction, indicative of functional inactivation. These data support the conclusion that by interacting with HSP70, PET-16 alters key chaperone functions of this cancer-critical survival protein, contributing to death of tumor cells. In addition to BRAF(V600E), PET-16 leads to altered expression of several other proteins (such as Integrin β1, AKT and EGFR) and mitochondrial proteins (such as Hexokinase II, Cyclophilin D and Cytochrome C) (FIGS. 4F-I); this is indicative of impaired overall cellular proteostasis.

Moreover, activation of cytokine signaling pathways, including those regulated by STAT proteins (signal transducer and activators of transcription) is associated with the initiation, progression and drug resistance of many tumor types, such as melanomas. STAT3 and STAT1 activation can occur in response to cytokines like IL-6. It was found that IL-6 promotes phosphorylation of both of these proteins in many of the melanoma cell lines that were examined. Notably, in each case examined, an IL-6 mediated phosphorylation of these proteins is inhibited by pre-treating the cells with PET-16. Representative data are in FIG. 4J, for STAT3, and similar results were obtained for STAT1. These results provide evidence that inhibiting HSP70 by PET-16 impairs the function of these critical signaling factors.

Lysosomes contain a number of enzymes, including cathepsin proteases that help in the turnover of macromolecules and organelles during normal metabolism and during autophagy. To further explore the effects of PET-16 on autophagic flux, the expression of the lysosomal cysteine peptidase cathepsin L, which plays an important role in the degradation of lysosomal cargo, was examined Like other members of this protein family, cathepsin L is synthesized as an inactive precursor that undergoes proteolytic processing to the mature, active form during transport to the acidic environment of the endosomal/lysosomal compartment through autoprocessing or cleavage by other cathepsins. It was found that PET-16 caused an accumulation of the precursor procathepsin L and a markedly reduced abundance of the smaller, mature form of the enzyme (FIG. 4K); this points to an impaired processing of this lysosomal enzyme and impaired lysosomal function needed for the process of autophagy.

Because ubiquitin often serves as a covalent tag to mark proteins for degradation, an accumulation of ubiquitinated polypeptides also is indicative of impaired proteostasis. Here, too, immunoblot analysis of lysates from PET-16 treated cells reveals an accumulation of a heterogeneous population of ubiquitinated polypeptides, especially in the detergent insoluble cell fraction (FIG. 4L).

Example 5

PET-16 Inhibits HSP70-Client Cyclophilin D and Reduces ATP Production in Tumor Cells Although a significant fraction of HSP70 protein resides in the cytoplasm, it also has documented roles in the nucleus, plasma membrane, lysosomes, and it is found extracellularly. It is known that the stress-inducible HSP70 is an ARF-interacting protein in the mitochondria of tumor cells. However, its potential activities at that location have not been investigated. Mitochondria are key factors in the regulation of cell death pathways, metabolism and energy generation, including ATP production. Consequently, a sustained disruption of the structural and functional integrity of these organelles is cytotoxic. PET-16, which contains the mitochondrial targeting motif TPP, was utilized to begin to address an important unresolved aspect of HSP70 biology and tumor pathology, namely its potential role in mitochondria.

This investigation was initiated by using subcellular fractionation assays to isolate mitochondria from several human tumor cell lines. During the course of these studies, a number of cell lines were utilized to assure consistency, and the results obtained have been reproducible among all cell lines sampled. As an example, western blot analyses of mitochondrial proteins isolated from the H1299 lung, and the MIA PaCa-2 pancreatic, carcinoma cell lines confirmed that a fraction of the stress-inducible HSP70 protein is constitutively present in these tumor cell organelles (FIGS. 5A-C). In contrast to tumor cells, normal cells lack appreciable levels of HSP70 in both the mitochondria and cytoplasmic preparations; this is illustrated by western blot analysis of proteins isolated from normal mouse liver (FIGS. 5C and 5D). As normal cells have very little, if any, HSP70 protein expressed, this provides a therapeutic window for treating tumor cells by preferentially targeting this molecular chaperone, HSP70. As some of the controls for the integrity of the mitochondrial fractions, western blot analysis was performed for the mitochondrial chaperone GRP75 (mortalin, HSPA9) and the outer mitochondrial membrane protein BAK. Both GRP75 and BAK were readily detected in the mitochondrial fractions from tumor and normal cells. Consistent with previous studies, the data also show that the constitutively expressed 90 kDa molecular chaperone, HSP90, is present at relatively low levels in most normal mitochondria, but is abundantly present in both the cytoplasm and mitochondria of tumor cells (FIGS. 5C and 5D). HSP105 exhibits a similar pattern to that of HSP90 (FIG. 5D). Such data are part of accumulating evidence that, while molecular chaperones generally serve compartment-specific, perhaps non-redundant, roles in unstressed normal cells, some of these proteins are differentially exploited in tumor cells likely to oversee critical protein homeostasis within certain organelles.

Cyclophilin D (Cyp-D) binds to the mitochondrial molecular motor $F_oF_1$-ATP synthase; the latter catalyzes the synthesis of ATP from ADP and phosphate. Cyp-D also modulates the mitochondrial permeability transition pore (mPTP), a well-characterized key effector of mitochondrial-mediated cell death. Purified mitochondria prepared from H1299 lung carcinoma cell line was incubated with increasing amounts of PET-16 or PES. PET-16, but not DMSO or PES, significantly reduced the abundance of Cyp-D in the soluble-protein fraction (FIG. 5E), consistent with functional inactivation. PET-16 exposure lead to a clear decrease in cellular ATP levels in tumor cells, indicative of impaired mitochondrial bioenergetics (FIG. 5F). In contrast, primary melanocytes and nontransformed human fibroblasts (IMR90) exhibited no decrease in total ATP levels (FIG. 5F). These results indicate that PET-16 impairs mitochondrial bioenergetics in tumor cells, but not that of normal cells.

Example 6

PET-16 Synergizes with BRAF Inhibitors

The BRAF protein is involved in sending signals inside cells, which are involved in directing cell growth. Mutations in the serine-threonine kinase BRAF occur frequently in many human cancers, contributing to tumorigenesis. While mutant BRAF(V600E)-selective inhibitors have shown clinical efficacy, most patients eventually develop drug resistance. Interestingly, many of the signaling mediators that have been implicated in development of BRAF inhibitor acquired and intrinsic resistance are clients of the HSP70 chaperone machinery.

It was determined if a combination of PET-16 together with a BRAF-inhibitor will synergize to enhance melanoma tumor cell death. It was then confirmed that PET-16 is able to synergize with PLX4032 (Vemurafenib), a V600 mutant BRAF inhibitor approved by the FDA for the treatment of late-stage melanoma (FIG. 6). In contrast, PES-Cl did not synergize with PLX4032 (Vemurafenib) (FIG. 6).

Example 7

PET-16 Impairs Metastasis in a Metastatic Mouse Model of Melanoma

The inhibitory effect of PET-16 on metastasis was tested in vivo, a well-recognized pulmonary metastatic model was utilized in which immunocompetent, wild-type C57BL/6 mice were injected with the highly metastatic mouse melanoma cell line B16 (FIG. 7). These results illustrate that PET-16 significantly reduced the extent of lung metastases and may have benefit as an anti-metastatic agent.

Example 8

Crystallographic Data on the DnaK-SBD in Complex with PET-16

Although several HSP70 compounds that interact with the N-terminal NBD domain of HSP70 have been identified, there is essentially no X-ray co-crystallographic data on HSP70 proteins complexed with small molecule modulators that specifically bind to the C-terminal domain of HSP70. Such data are needed to provide additional insight about mechanisms of HSP70-client interaction, occurring at the C-terminus. To better understand the structural basis for how these small molecules target the C-terminus of HSP70/

DnaK, crystals of protein-inhibitor complexes suitable for analysis by X-ray crystallography were generated. Accordingly crystals of the SBD of DnaK (aa 389-607) were obtained in the presence of PET-16 in the $P4_32_12$ space group. The crystals contained two molecules (referred to as Molecule A (MolA) and Molecule B (MolB)) per asymmetric unit cell and diffracted to a nominal resolution of 3.45 Å (FIG. 8A). Both molecules are highly similar to previously determined DnaK SBD structures, each containing the canonical SBDβ (residues 393-507) and SBDα. During and following refinement, additional difference density was detected in MolB, but not MolA, that occupies a hydrophobic pocket formed by residues in strand β1 (L399) and loops LL,1 (L392 and P396), L6,7 (G482) and Lα,β (A503 and S504) of the DnaK-PET-16 complex (FIGS. 8A-C). This PET-16 binding pocket in the DnaK-PET-16 complex corresponds to a hydrophobic cleft flanked by residues located on strands β1 (L401) and β7 (G484) and loops LL,1 (L394 and P398) and Lα,β (N505 and D506) of the SBDβ subdomain of the human stress-inducible HSP70 (FIG. 8D). Notably, this additional electron density in MolB of the DnaK-PET-16 complex was modeled as PET-16, with the electron-rich phosphine in the region of greatest electron density and the phenyl group and acetylene linker pointing into the hydrophobic pocket and the TPP pointing out towards solvent, which was consistent with additional rounds of crystallographic refinement (FIGS. 8B and 8C). Also, in MolB, the interaction between the modeled PET-16 and loops LL,1 and Lα,β brings residue L392 closer to residues A503 and S504 by about 3.5 Å and about 3.1 Å, respectively, relative to their positions in MolA. Since loop Lα,β bridges SBDβ to SBDα and that the loop LL,1 connects NBD to SBDβ, it is reasonable to speculate that the interaction of PET-16 with this particular region may impede the conformational flexibility, and NBD-SBD crosstalk, needed for proper chaperone function. Indeed, as discussed above (FIG. 4), PET-16 reduces the cellular interactions between HSP70 and substrates. Taken together, our crystallographic data unveiled a previously unrecognized allosteric pocket in the C-terminal domain of DnaK/HSP70 molecule; this binding site does not overlap with the canonical substrate peptide-binding pocket.

Example 9

Mutational Analysis Supports the Site of Interaction of PET-16 with DnaK and HSP70

The information from crystal structure analysis pointed to particular amino acid residues as potential contact sites for interaction with PET-16. Single point mutants were thereby introduced in the context of a full-length DnaK protein, as well as at the corresponding residues within HSP70; these mutant proteins were analyzed by ITC for ability to bind to PET-16. The DnaK mutations included residues L392D, P396L, L399R, G482D, A503D and S504A; those in HSP70 were L394D, P398L, L401R, G484D, N505D and D506A. As used herein, a change in an amino acid in a sequence is denoted by the original amino acid, followed by its amino acid number in the sequence, and finally followed by the amino acid change in the sequence. For example, L392D refers to replacement of the Leu (L) at amino acid position 392 with Asp (D).

Based on ITC analysis (Tables 2A and 2B), the presence of each of these mutations reduced the affinity of the proteins for interaction with PET-16; an interaction between HSP70/DnaK and the small molecule was most notably impaired by mutations in loop Lα,β (A503D and S504A in DnaK; N505D and D506A in HSP70) and the SBDβ site (P396L, L399R and G482D in DnaK; P398L, L401R and G484D in HSP70). Tables 2A and 2B provide data which illustrates the binding of PET-16 directly to C-terminal substrate binding domain of ADP-bound DnaK and ADP-bound HSP70. Shown are the ITC-derived binding constants ($K_d$ values) from assays of PET-16 incubated with wild-type and mutated full-length ADP-DnaK (Table 2A) and ADP-HSP70 proteins (Table 2B). There is an impaired interaction between PET-16 and ATP-bound HSP70 (Table 2B). These data provide additional support for the previously unidentified modulatory binding site of PET-16 within the C-terminal domain of DnaK (FIGS. 8A-C) and HSP70 (FIG. 8D).

Amino acids L392, P396, L399, G482, A503, and S504 are key residues that contact PET-16 in DnaK. The former four residues are conserved and correspond to residues L394, P398, L401, and G484 in HSP70. Like A503 and S504 in DnaK, residues N505 and D506 in HSP70 also form the entrance to a conserved inhibitor binding pocket. In sum, the data obtained in these mutagenesis studies described herein and in Leu et al, 2014, cited herein and incorporated by reference, support the information provided by the X-ray crystal structure of DnaK-PET-16; they suggest that residues L394, P398, L401, G484, N505, and D506 in HSP70, as well as the corresponding residues in DnaK, represent important elements for the interaction of PET-16 and PES.

TABLE 2A

| ADP-DnaK | PET-16 ($K_d$, μM) |
| --- | --- |
| WT | 6.0 ± 1.8 |
| L392D | 37.9 ± 4.6 |
| P396L | 53.5 ± 9.9 |
| L399R | 69.7 ± 2.7 |
| G482D | 38.1 ± 4.6 |
| A503D | 77.5 ± 2.1 |
| S504A | 49.6 ± 1.3 |

TABLE 2B

| | PET-16 ($K_d$, μM) | NRLLLTG ($K_d$, μM) |
| --- | --- | --- |
| ADP-HSP70 | | |
| WT | 3.8 ± 1.0 | 10.0 ± 3.2 |
| L394D | 30.8 ± 0.6 | |
| P398L | 23.4 ± 1.2 | |
| L401R | 43.2 ± 9.9 | |
| G484D | 98.8 ± 5.1 | |
| N505D | 146.7 ± 6.5 | |
| D506A | 112.0 ± 3.8 | |
| ATP-HSP70 | | |
| WT | 130 ± 8.3 | 1248 ± 15 |

Example 10

Identification of a Novel PET-16 Analog

Based on data from X-ray crystallography analyses, PET-16 was modified to generate a novel analog, referred to here as PET-3C (FIG. 1F). An additional analog, referred to here as PET-DR (FIG. 1G) that is predicted to be too bulky to bind to the identified PET-16 hydrophobic groove, was also generated. Using ITC, it was confirmed that PET-3C preferentially interacted with the ADP-HSP70 with a with $K_d$ value of about 4.9 μM (FIG. 9A); in contrast, this analog exhibits notably reduced interaction with the ATP-bound conformation of HSP70 (FIG. 9B). Interestingly, and in contrast to PET-16, PET-3C binds much less well to DnaK under the same conditions (compare FIGS. 9C and 3E). PET-3C preferentially kills tumor cells relative to non-transformed cells (FIG. 9D), consistent with its ability to bind to HSP70. It is much less effective in inhibiting *E. coli* growth (FIGS. 9E and 9F), a property that is consistent with its impaired interaction with ADP-bound DnaK (FIG. 9C). The compound PET-DR does not exhibit a good binding affinity for HSP70 or DnaK (FIGS. 9G and 9H). PET-DR is also not effectively cytotoxic for tumor cells and has little effect on *E. coli*. Mutagenesis studies in conjunction with isothermal titration calorimetry provided additional support that PET-3C binds to the same hydrophobic pocket as PET-16 (Table 3). Interactions between HSP70 and PET-3C were markedly impaired by mutations L394D, P398L, L401R, G484D, N505D and D506A in HSP70.

Specifically, Table 3 provides data illustrating that PET-3C binds to the PET-16 hydrophobic pocket located in the C-terminal domain of HSP70. ITC-derived binding constants ($K_d$ values) from assays of PET-3C incubated with wild-type and mutated full-length ADP-HSP70 proteins are provided. There is impaired interaction between PET-3C and ATP-bound HSP70, between PET-DR and ADP-HSP70, and between PET-DR and ATP-HSP70.

TABLE 3

|  | PET-3C ($K_d$, μM) | PET-DR ($K_d$, μM) |
| --- | --- | --- |
| ADP-HSP70 | | |
| WT | 4.9 ± 2.1 | 61.0 ± 8.2 |
| L394D | 30.3 ± 5.0 | |
| P398L | 37.2 ± 1.7 | |
| L401R | 60.4 ± 3.9 | |
| G484D | 97.9 ± 2.9 | |
| N505D | 90.8 ± 1.9 | |
| D506A | 85.0 ± 2.3 | |
| ATP-HSP70 | | |
| WT | 71.7 ± 4.8 | 191 ± 38 |

In conclusion, we generated crystals of the C terminal domain of DnaK, both alone and in complex with either a peptide substrate or inhibitor. Our data provide evidence that the small molecule PET-16, described herein, represents an inhibitor class that binds within a conserved C-terminal binding pocket of the HSP70 and DnaK proteins; this pocket is distinct from the site of chaperone—substrate interaction and is evident only in the non-ATP-bound protein conformation. Changes in local protein environment are apparent in the PET-16-bound versus unbound state. Previous investigations, using either mutation analyses or structural studies, have established the importance of the residues within loops LL,1, L6,7, and Lα,β of DnaK for allosteric coupling of NBD and SBD, the interaction of chaperone with the critical HSP40 cochaperone, or overall bacterial viability. By binding to this well-conserved C-terminal binding pocket, the inhibitors disrupt the conformational flexibility between the SBDα-SBDβ and/or NBD-SBD interface needed for allosteric regulation and proper chaperone function. These small molecules reduce the survival of mammalian tumor cells, impair bacterial growth, modulate cellular interactions between HSP70 and cochaperones, and alter interactions with substrates. Without wishing to be bound by theory, the combined data support that by locking (or prolonging) HSP70 and DnaK in a particular conformational state, these small molecules negatively impact the substrate binding/release cycle of HSP70 and DnaK allostery. Indeed, the inhibitors may function in a manner that may impart a "gain-of-function" phenotype, resulting in the accumulation of aggregates and misfolded proteins in detergent insoluble cell fractions, optionally in association with the chaperone itself. Also, while PES and PET-16 share many properties, ongoing investigations point to differences as well. It is anticipated that the various mutant forms of DnaK and HSP70 generated in this investigation, as well as the inhibitor compounds described, will have direct utility for future in vitro and in vivo studies aimed at dissecting the role of the binding region and particular amino acid residues in chaperone activities, such as allostery regulation, substrate binding/release, and interaction with particular cochaperone mediators. The compositions and methods described herein represent a timely and useful molecular platform to inform the structure-based design of additional modulators that preferentially target the C-terminal binding pocket of HSP70 and DnaK proteins to alter the chaperone—client network, with application to human disease.

All publications cited in this specification, particularly U.S. Provisional Patent Application No. 61/944,798 and Leu, J I et al, 2014 ACS Chem. Biol. 9:2508-2516, are incorporated herein by reference. While the invention has been described with reference to particular embodiments, it will be appreciated that modifications can be made without departing from the spirit of the invention. Such modifications are intended to fall within the scope of the appended claims.

DOCUMENTS

Adams, Afonine, Bunkóczi, Chen, Davis, Echols, Headd, Hung, Kapral, Grosse-Kunstleve (2010) PHENIX: a comprehensive Python-based system for macromolecular structure solution. Acta Crystallogr. D Biol. Crystallogr. 66, 213-221.

Afonine, Grosse-Kunstleve, Echols, Headd, Moriarty, Mustyakimov, Terwilliger, Urzhumtsev, Zwart, and Adams (2012) Towards automated crystallographic structure refinement with phenix.refine. Acta Crystallogr. D Biol. Crystallogr. 68, 352-367.

Balaburski, Leu, Beeharry, Hayik, Andrake, Zhang, Herlyn, Villanueva, Dunbrack, Yen (2013) A modified HSP70 inhibitor shows broad activity as an anticancer agent. Mol. Cancer Res. 11, 219-229.

Bertelsen, Chang, Gestwicki, and Zuiderweg (2009) Solution conformation of wild-type *E. coli* Hsp70 (DnaK) chaperone complexed with ADP and substrate. Proc. Natl. Acad. Sci. USA 106, 8471-8476.

Brodsky and Chiosis (2006) Hsp70 molecular chaperones: emerging roles in human disease and identification of small molecule modulators. Curr. Top. Med. Chem. 6, 1215-1225.

Chang, Miyata, Ung, Bertelsen, McQuade, Carlson, Zuiderweg, and Gestwicki (2011) Chemical screens against a reconstituted multiprotein complex: myricetin blocks DnaJ regulation of DnaK through an allosteric mechanism. Chem. Biol. 18, 210-221.

Daugaard, Rohde, and Jäättelä (2007) The heat shock protein 70 family: highly homologous proteins with overlapping and distinct functions. FEBS Lett. 581, 3702-3710.

DeLano (2002) The PyMOL Molecular Graphics System. http://www.pymol.org.

Iki, Yoshikawa, Nishikior, Jaudal, Matsumoto-Yokoyama, Mitsuhara, Meshi, and Ishikawa (2010) In vitro assembly of plant RNA-induced silencing complexes facilitated by molecular chaperone HSP90. Mol. Cell 39, 282-291.

Iwasaki, Kobayashi, Yoda, Sakaguchi, Katsuma, Suzuki, Tomari (2010) Hsc70/Hsp90 chaperone machinery mediates ATP-dependent RISC loading of small RNA duplexes. Mol. Cell 39, 292-299.

Kettern, Dreiseidler, Tawo, and Höhfeld (2010) Chaperone-assisted degradation: multiple paths to destruction. Biol. Chem. 391, 481-489.

Kim, Hipp, Hayer-Hartl, and Hartl (2013) Molecular chaperone functions in protein folding and proteostasis. Ann. Rev. Biochem. 82, 323-355.

Kityk, Kopp, Sinning, and Mayer (2012) Structure and dynamics of the ATP-bound open conformation of Hsp70 chaperones. Mol. Cell 48, 863-874.

Kwak and Tomari (2012) The N domain of argonaute drives duplex unwinding during RISC assembly. Nat. Struct. Mol. Biol. 19, 145-151.

Leu, Pimkina, Frank, Murphy, and George (2009) A small molecule inhibitor of inducible heat shock protein 70. Mol. Cell 36, 15-27.

Leu, Pimkina, Pandey, Murphy, and George (2011) HSP70 inhibition by the small-molecule 2-phenylethynesulfonamide impairs protein clearance pathways in tumor cells. Mol. Cancer Res. 9, 936-947.

Liu, B., Han, Y., and Qian, S. B. (2013) Cotranslational response to proteotoxic stress by elongation pausing of ribosomes. Mol. Cell 49, 453-463.

Mayer and Bukau (2005) Hsp70 chaperones: cellular functions and molecular mechanism. Cell Mol. Life Sci. 62, 670-684.

Mayer (2013) Hsp70 chaperone dynamics and molecular mechanism. Trends Biochem. Sci. 38,507-514.

McCoy, Grosse-Kunstleve, Adams, Winn, Storoni, and Read (2007) Phaser crystallographic software. J. Appl. Crystallogr. 40, 658-674.

Millard, Pathania, Shabaik, Taheri, Deng, and Neamati (2010) Preclinical evaluation of novel triphenylphosphonium salts with broad-spectrum activity. PLoS ONE 5(10).

Morishima, Lau, Peng, Miyata, Gestwicki, Pratt, and Osawa (2011) Heme-dependent activation of neuronal nitric oxide synthase by cytosol is due to an Hsp70-dependent, thioredoxin-mediated thiol-disulfide interchange in the heme/substrate binding cleft. Biochemistry 50:7146-7156.

Murphy (2013) The HSP70 family and cancer. Carcinogenesis. 34, 1181-1188.

Nylandsted, Gyrd-Hansen, Danielewicz, Fehrenbacher, Lademann, Hoyer-Hansen, Weber, Multhoff, Rohde, and Jäättelä (2004) Heat shock protein 70 promotes cell survival by inhibiting lysosomal membrane permeabilization. J. Exp. Med. 200, 425-435.

Otwinowski and Minor (1997) Processing of X-ray diffraction data collected in oscillation mode. Methods Enzymol. 276, 307-326.

Patury, Miyata, and Gestwicki (2009) Pharmacological targeting of the Hsp70 chaperone. Curr. Top. Med. Chem. 9, 1337-1351.

Pellecchia, Montgomery, Stevens, Vander Kooi, Feng, Gierasch, and Zuiderweg (2000) Structural insights into substrate binding by the molecular chaperone DnaK. Nat. Struct. Biol. 7, 298-303.

Powers, Jones, Barillari, Westwood, van Montfort, and Workman (2010) Targeting HSP70: the second potentially druggable heat shock protein and molecular chaperone. Cell Cycle 9, 1542-1550.

Qi, Sarbeng, Liu, Le, Xu, Xu, Yang, Wong, Vorvis, Hendrickson (2013) Allosteric opening of the polypeptide-binding site when an Hsp70 binds ATP. Nat. Struct. Mol. Biol. 20, 900-907.

Rérole, Gobbo, De Thonel, Schmitt, Pais de Barros, Hammann, Lanneau, Fourmaux, Deminov, Micheau (2011) Peptides and aptamers targeting HSP70: a novel approach for anticancer chemotherapy. Cancer Res. 71, 484-495.

Rodina, Patel, Kang, Patel, Baaklini, Wong, Taldone, Yan, Yang, Maharaj (2013) Identification of an Allosteric Pocket on Human Hsp70 Reveals a Mode of Inhibition of This Therapeutically Important Protein. Chem. Biol. 20, 1469-1480.

Rousaki, Miyata, Jinwal, Dickey, Gestwicki, Zuiderweg (2011) Allosteric drugs: the interaction of antitumor compound MKT-077 with human Hsp70 chaperones. J. Mol. Biol. 411, 614-632.

Ryhänen, Hyttinen, Kopitz, Rilla, Kuusisto, Mannermaa, Viiri, Holmberg, Immonen, Men (2009) Crosstalk between Hsp70 molecular chaperone, lysosomes and proteasomes in autophagy-mediated proteolysis in human retinal pigment epithelial cells. J. Cell. Mol. Med. 13, 3616-3631.

Schlecht, Scholz, Dahmen, Wegener, Sirrenberg, Musil, Bomke, Eggenweiler, Mayer, Bukau (2013) Functional analysis of hsp70 inhibitors. PLoS One. 8(11):e78443.

Smith, Hartley, and Murphy (2011) Mitochondria-targeted small molecule therapeutics and probes. Antioxid. Redox Signal 15, 3021-3038.

Swain, Dinler, Sivendran, Montgomery, Stotz, and Gierasch (2007) Hsp70 chaperone ligands control domain association via an allosteric mechanism mediated by the interdomain linker. Mol. Cell 26, 27-39.

Wang, Kurochkin, Pang, Hu, Flynn, and Zuiderweg (1998) NMR solution structure of the 21 kDa chaperone protein DnaK substrate binding domain: a preview of chaperone-protein interaction. Biochemistry 37, 7929-7940.

Zahn, Berthold, Kieslich, Knappe, Hoffmann, and Sträter (2013) Structural studies on the forward and reverse binding modes of peptides to the chaperone DnaK. J. Mol. Biol. 425, 2463-2479

Zhu, Zhao, Burkholder, Gragerov, Ogata, Gottesman, and Hendrickson (1996) Structural analysis of substrate binding by the molecular chaperone DnaK. Science 272, 1606-1614.

Zhuravleva, Clerico, and Gierasch (2012) An interdomain energetic tug-of-war creates the allosterically active state in Hsp70 molecular chaperones. Cell 151, 1296-1307.

What is claimed is:

1. A method of inhibiting heat shock protein (HSP) 70 or DnaK, comprising administering a compound to a subject in need thereof, wherein the compound is triphenyl (phenyl ethynyl) phosphonium bromide (PET-16), and wherein diseases treatable by such inhibition include melanoma or lung carcinoma.

2. The method according to claim 1, further comprising administering a genotoxic agent, which is radiation, which enhances the effectiveness of said compound.

3. The method according to claim 2, wherein said genotoxic agent is administered prior to, concurrently with, or subsequent to administration of the compound.

4. The method according to claim 1, wherein said compound is administered in a pharmaceutically acceptable carrier or excipient.

5. The method according to claim 1, wherein the compound is triphenyl (phenyl ethynyl) phosphonium bromide (PET-16) and said disease is a melanoma.

6. The method according to claim 1, wherein the compound is triphenyl (phenyl ethynyl) phosphonium bromide (PET-16) and said disease is lung carcinoma.

* * * * *

SEQUENCE LISTING

<160> NUMBER OF SEQ ID NOS: 7

<210> SEQ ID NO 1
<211> LENGTH: 1926
<212> TYPE: DNA

<213> ORGANISM: Homo sapiens

<400> SEQUENCE: 1

```
atggccaaag ccgcggcgat cggcatcgac ctgggcacca cctactcctg cgtgggggtg      60
ttccaacacg gcaaggtgga gatcatcgcc aacgaccagg gcaaccgcac cacccccagc     120
tacgtggcct tcacggacac cgagcggctc atcggggatg cggccaagaa ccaggtggcg     180
ctgaacccgc agaacaccgt gtttgacgcg aagcggctga tcggccgcaa gttcggcgac     240
ccggtggtgc agtcggacat gaagcactgg cctttccagg tgatcaacga cggagacaag     300
cccaaggtgc aggtgagcta caaggggac accaaggcat ctaccccga ggagatctcg       360
tccatggtgc tgaccaagat gaaggagatc gccgaggcgt acctgggcta cccggtgacc     420
aacgcggtga tcaccgtgcc ggcctacttc aacgactcgc agcgccaggc caccaaggat     480
gcgggtgtga tcgcggggct caacgtgctg cggatcatca cgagcccac ggccgccgcc      540
atcgcctacg gcctggacag aacgggcaag ggggagcgca acgtgctcat ctttgacctg     600
ggcggggca ccttcgacgt gtccatcctg acgatcgacg acggcatctt cgaggtgaag      660
gccacggccg ggacacccca cctgggtggg gaggactttg acaacaggct ggtgaaccac     720
ttcgtggagg agttcaagag aaaacacaag aaggacatca gccagaacaa gcgagccgtg     780
aggcggctgc gcaccgcctg cgagagggcc aagaggaccc tgtcgtccag cacccaggcc     840
agcctggaga tcgactccct gtttgagggc atcgacttct acacgtccat caccagggcg     900
aggttcgagg agctgtgctc cgacctgttc cgaagcaccc tggagcccgt ggagaaggct     960
ctgcgcgacg ccaagctgga caaggcccag attcacgacc tggtcctggt cgggggctcc    1020
acccgcatcc ccaaggtgca gaagctgctg caggacttct tcaacgggcg cgacctgaac    1080
aagagcatca ccccgacga ggctgtggcc tacggggcgg cggtgcaggc ggccatcctg    1140
atggggggaca agtccgagaa cgtgcaggac ctgctgctgc tggacgtggc tcccctgtcg    1200
ctggggctgg agacgccgg aggcgtgatg actgccctga tcaagcgcaa ctccaccatc    1260
cccaccaagc agacgcagat cttcaccacc tactccgaca accaacccgg ggtgctgatc    1320
caggtgtacg agggcgagag ggccatgacg aaagacaaca atctgttggg gcgcttcgag    1380
ctgagcggca tccctccggc ccccaggggc gtgccccaga tcgaggtgac cttcgacatc    1440
gatgccaacg gcatcctgaa cgtcacggcc acgacaaga gcaccggcaa ggccaacaag    1500
atcaccatca ccaacgacaa gggccgcctg agcaaggagg agatcgagcg catggtgcag    1560
gaggcggaga agtacaaagc ggaggacgag gtgcagcgcg agagggtgtc agccaagaac    1620
gccctggagt cctacgcctt caacatgaag agcgccgtgg aggatgaggg gctcaagggc    1680
aagatcagcg aggccgacaa gaagaaggtg ctggacaagt gtcaagaggt catctcgtgg    1740
ctggacgcca acaccttggc cgagaaggac gagtttgagc acaagaggaa ggagctggag    1800
caggtgtgta cccccatcat cagcggactg taccagggtg ccggtggtcc cggggcctggg   1860
ggcttcgggg ctcagggtcc caagggaggg tctgggtcag ccccaccat tgaggaggta    1920
gattag                                                                1926
```

<210> SEQ ID NO 2
<211> LENGTH: 641
<212> TYPE: PRT
<213> ORGANISM: Homo sapiens

<400> SEQUENCE: 2

Met Ala Lys Ala Ala Ala Ile Gly Ile Asp Leu Gly Thr Thr Tyr Ser

-continued

```
1               5                   10                  15
Cys Val Gly Val Phe Gln His Gly Lys Val Glu Ile Ile Ala Asn Asp
                20                  25                  30
Gln Gly Asn Arg Thr Thr Pro Ser Tyr Val Ala Phe Thr Asp Thr Glu
                35                  40                  45
Arg Leu Ile Gly Asp Ala Ala Lys Asn Gln Val Ala Leu Asn Pro Gln
                50                  55                  60
Asn Thr Val Phe Asp Ala Lys Arg Leu Ile Gly Arg Lys Phe Gly Asp
65                              70                  75                  80
Pro Val Val Gln Ser Asp Met Lys His Trp Pro Phe Gln Val Ile Asn
                        85                  90                  95
Asp Gly Asp Lys Pro Lys Val Gln Val Ser Tyr Lys Gly Asp Thr Lys
                        100                 105                 110
Ala Phe Tyr Pro Glu Glu Ile Ser Ser Met Val Leu Thr Lys Met Lys
                        115                 120                 125
Glu Ile Ala Glu Ala Tyr Leu Gly Tyr Pro Val Thr Asn Ala Val Ile
                130                 135                 140
Thr Val Pro Ala Tyr Phe Asn Asp Ser Gln Arg Gln Ala Thr Lys Asp
145                 150                 155                 160
Ala Gly Val Ile Ala Gly Leu Asn Val Leu Arg Ile Ile Asn Glu Pro
                        165                 170                 175
Thr Ala Ala Ile Ala Tyr Gly Leu Asp Arg Thr Gly Lys Gly Glu
                180                 185                 190
Arg Asn Val Leu Ile Phe Asp Leu Gly Gly Gly Thr Phe Asp Val Ser
                        195                 200                 205
Ile Leu Thr Ile Asp Asp Gly Ile Phe Glu Val Lys Ala Thr Ala Gly
                210                 215                 220
Asp Thr His Leu Gly Gly Glu Asp Phe Asp Asn Arg Leu Val Asn His
225                 230                 235                 240
Phe Val Glu Glu Phe Lys Arg Lys His Lys Lys Asp Ile Ser Gln Asn
                        245                 250                 255
Lys Arg Ala Val Arg Arg Leu Arg Thr Ala Cys Glu Arg Ala Lys Arg
                        260                 265                 270
Thr Leu Ser Ser Ser Thr Gln Ala Ser Leu Glu Ile Asp Ser Leu Phe
                275                 280                 285
Glu Gly Ile Asp Phe Tyr Thr Ser Ile Thr Arg Ala Arg Phe Glu Glu
                290                 295                 300
Leu Cys Ser Asp Leu Phe Arg Ser Thr Leu Glu Pro Val Glu Lys Ala
305                 310                 315                 320
Leu Arg Asp Ala Lys Leu Asp Lys Ala Gln Ile His Asp Leu Val Leu
                        325                 330                 335
Val Gly Gly Ser Thr Arg Ile Pro Lys Val Gln Lys Leu Leu Gln Asp
                        340                 345                 350
Phe Phe Asn Gly Arg Asp Leu Asn Lys Ser Ile Asn Pro Asp Glu Ala
                355                 360                 365
Val Ala Tyr Gly Ala Ala Val Gln Ala Ala Ile Leu Met Gly Asp Lys
                370                 375                 380
Ser Glu Asn Val Gln Asp Leu Leu Leu Leu Asp Val Ala Pro Leu Ser
385                 390                 395                 400
Leu Gly Leu Glu Thr Ala Gly Gly Val Met Thr Ala Leu Ile Lys Arg
                        405                 410                 415
Asn Ser Thr Ile Pro Thr Lys Gln Thr Gln Ile Phe Thr Thr Tyr Ser
                        420                 425                 430
```

Asp Asn Gln Pro Gly Val Leu Ile Gln Val Tyr Glu Gly Glu Arg Ala
            435                 440                 445

Met Thr Lys Asp Asn Asn Leu Leu Gly Arg Phe Glu Leu Ser Gly Ile
        450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
            565                 570                 575

Val Ile Ser Trp Leu Asp Ala Asn Thr Leu Ala Glu Lys Asp Glu Phe
        580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
        610                 615                 620

Gln Gly Pro Lys Gly Gly Ser Gly Ser Gly Pro Thr Ile Glu Glu Val
625                 630                 635                 640

Asp

<210> SEQ ID NO 3
<211> LENGTH: 1917
<212> TYPE: DNA
<213> ORGANISM: Escherchia coli

<400> SEQUENCE: 3
atgggtaaaa taattggtat cgacctgggt actaccaact cttgtgtagc gattatggat     60
ggcaccactc tcgcgtgct ggagaacgcc gaaggcgatc gcaccacgcc ttctatcatt    120
gcctataccc aggatggtga actctagtt ggtcagccgg ctaaacgtca ggcagtgacg    180
aacccgcaaa cactctgtt tgcgattaaa cgcctgattg gtcgccgctt ccaggacgaa    240
gaagtacagc gtgatgtttc catcatgccg ttcaaaatta ttgctgctga taacggcgac    300
gcatgggtcg aagttaaagg ccagaaaatg caccgccgc agatttctgc tgaagtgctg    360
aaaaaaatga gaaaaccgc tgaagattac ctgggtgaac ggtaactga agctgttatc    420 accgtaccgg catactttaa cgatgctcag cgtcaggcaa ccaaagacgc aggccgtatc    480
gctggtctgg aagtaaaacg tatcatcaac gaaccgaccg cagctgcgct ggcttacggt    540
ctggacaaag cactggcaa ccgtactatc gcggtttatg acctgggtgg tggtactttc    600
gatatttcta ttatcgaaat cgacgaagtt gacggcgaaa aaaccttcga agttctggca    660
accaacggtg ataccccacct ggggggtgaa gacttcgaca gccgtctgat caactatctg    720
gttgaagaat caagaaaga tcagggcatt gacctgcgca cgatccgct ggcaatgcag    780 cgcctgaaaa agcggcaga aaagcgaaa atcgaactgt cttccgctca gcagaccgac    840
gttaacctgc catacatcac tgcagacgcg accggtccga acacatgaa catcaaagtg    900

```
actcgtgcga aactggaaag cctggttgaa gatctggtaa accgttccat tgagccgctg    960
aaagttgcac tgcaggacgc tggcctgtcc gtatctgata tcgacgacgt tatcctcgtt   1020
ggtggtcaga ctcgtatgcc aatggttcag aagaaagttg ctgagttctt tggtaaagag   1080
ccgcgtaaag acgttaaccc ggacgaagct gtagcaatcg gtgctgctgt tcagggtggt   1140
gttctgactg gtgacgtaaa agacgtactg ctgctggacg ttaccccgct gtctctgggt   1200
atcgaaacca tgggcggtgt gatgacgacg ctgatcgcga aaaacaccac tatcccgacc   1260
aagcacagcc aggtgttctc taccgctgaa gacaaccagt ctgcggtaac catccatgtg   1320
ctgcagggtg aacgtaaacg tgcggctgat aacaaatctc tgggtcagtt caacctagat   1380
ggtatcaacc cggcaccgcg cggcatgccg cagatcgaag ttaccttcga tatcgatgct   1440
gacggtatcc tgcacgtttc cgcgaaagat aaaaacagcg gtaaagagca aagatcacc   1500
atcaaggctt cttctggtct gaacgaagat gaaatccaga aatggtacg cgacgcagaa   1560
gctaacgccg aagctgaccg taagtttgaa gagctggtac agactcgcaa ccagggcgac   1620
catctgctgc acagcacccg taagcaggtt gaagaagcag gcgacaaact gccggctgac   1680
gacaaaactg ctatcgagtc tgcgctgact gcactggaaa ctgctctgaa aggtgaagac   1740
aaagccgcta tcgaagcgaa aatgcaggaa ctggcacagg tttcccagaa actgatggaa   1800
atcgcccagc agcaacatgc ccagcagcag actgccggtg ctgatgcttc tgcaaacaac   1860
gcgaaagatg acgatgttgt cgacgctgaa tttgaagaag tcaaagacaa aaaatga     1917
```

<210> SEQ ID NO 4  
<211> LENGTH: 638  
<212> TYPE: PRT  
<213> ORGANISM: Escherichia coli

<400> SEQUENCE: 4

```
Met Gly Lys Ile Ile Gly Ile Asp Leu Gly Thr Thr Asn Ser Cys Val
1               5                   10                  15

Ala Ile Met Asp Gly Thr Thr Pro Arg Val Leu Glu Asn Ala Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
    50                  55                  60

Thr Leu Phe Ala Ile Lys Arg Leu Ile Gly Arg Arg Phe Gln Asp Glu
65                  70                  75                  80

Glu Val Gln Arg Asp Val Ser Ile Met Pro Phe Lys Ile Ile Ala Ala
                85                  90                  95

Asp Asn Gly Asp Ala Trp Val Glu Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Leu Asp Lys Gly Thr Gly Asn Arg Thr Ile Ala Val
            180                 185                 190
```

```
Tyr Asp Leu Gly Gly Gly Thr Phe Asp Ile Ser Ile Ile Glu Ile Asp
            195                 200                 205

Glu Val Asp Gly Glu Lys Thr Phe Glu Val Leu Ala Thr Asn Gly Asp
        210                 215                 220

Thr His Leu Gly Gly Glu Asp Phe Asp Ser Arg Leu Ile Asn Tyr Leu
225                     230                 235                 240

Val Glu Glu Phe Lys Lys Asp Gln Gly Ile Asp Leu Arg Asn Asp Pro
                245                 250                 255

Leu Ala Met Gln Arg Leu Lys Glu Ala Glu Lys Ala Lys Ile Glu
            260                 265                 270

Leu Ser Ser Ala Gln Gln Thr Asp Val Asn Leu Pro Tyr Ile Thr Ala
        275                 280                 285

Asp Ala Thr Gly Pro Lys His Met Asn Ile Lys Val Thr Arg Ala Lys
        290                 295                 300

Leu Glu Ser Leu Val Glu Asp Leu Val Asn Arg Ser Ile Glu Pro Leu
305                     310                 315                 320

Lys Val Ala Leu Gln Asp Ala Gly Leu Ser Val Ser Asp Ile Asp Asp
                325                 330                 335

Val Ile Leu Val Gly Gly Gln Thr Arg Met Pro Met Val Gln Lys Lys
            340                 345                 350

Val Ala Glu Phe Phe Gly Lys Glu Pro Arg Lys Asp Val Asn Pro Asp
        355                 360                 365

Glu Ala Val Ala Ile Gly Ala Ala Val Gln Gly Gly Val Leu Thr Gly
        370                 375                 380

Asp Val Lys Asp Val Leu Leu Leu Asp Val Thr Pro Leu Ser Leu Gly
385                     390                 395                 400

Ile Glu Thr Met Gly Gly Val Met Thr Thr Leu Ile Ala Lys Asn Thr
                405                 410                 415

Thr Ile Pro Thr Lys His Ser Gln Val Phe Ser Thr Ala Glu Asp Asn
            420                 425                 430

Gln Ser Ala Val Thr Ile His Val Leu Gln Gly Glu Arg Lys Arg Ala
        435                 440                 445

Ala Asp Asn Lys Ser Leu Gly Gln Phe Asn Leu Asp Gly Ile Asn Pro
450                     455                 460

Ala Pro Arg Gly Met Pro Gln Ile Glu Val Thr Phe Asp Ile Asp Ala
465                     470                 475                 480

Asp Gly Ile Leu His Val Ser Ala Lys Asp Lys Asn Ser Gly Lys Glu
                485                 490                 495

Gln Lys Ile Thr Ile Lys Ala Ser Ser Gly Leu Asn Glu Asp Glu Ile
            500                 505                 510

Gln Lys Met Val Arg Asp Ala Glu Ala Asn Ala Glu Ala Asp Arg Lys
        515                 520                 525

Phe Glu Glu Leu Val Gln Thr Arg Asn Gln Gly Asp His Leu Leu His
        530                 535                 540

Ser Thr Arg Lys Gln Val Glu Glu Ala Gly Asp Lys Leu Pro Ala Asp
545                     550                 555                 560

Asp Lys Thr Ala Ile Glu Ser Ala Leu Thr Ala Leu Glu Thr Ala Leu
                565                 570                 575

Lys Gly Glu Asp Lys Ala Ala Ile Glu Ala Lys Met Gln Glu Leu Ala
            580                 585                 590

Gln Val Ser Gln Lys Leu Met Glu Ile Ala Gln Gln His Ala Gln
        595                 600                 605

Gln Gln Thr Ala Gly Ala Asp Ala Ser Ala Asn Asn Ala Lys Asp Asp
```

```
              610                 615                 620
Asp Val Val Asp Ala Glu Phe Glu Glu Val Lys Asp Lys Lys
625                 630                 635

<210> SEQ ID NO 5
<211> LENGTH: 230
<212> TYPE: PRT
<213> ORGANISM: Escherichia coli

<400> SEQUENCE: 5

Met His His His His His Ile Glu Gly Arg Val Leu Leu Leu Asp
1               5                   10                  15

Val Thr Pro Leu Ser Leu Gly Ile Glu Thr Met Gly Gly Val Met Thr
                20                  25                  30

Thr Leu Ile Ala Lys Asn Thr Thr Ile Pro Thr Lys His Ser Gln Val
                35                  40                  45

Phe Ser Thr Ala Glu Asp Asn Gln Ser Ala Val Thr Ile His Val Leu
        50                  55                  60

Gln Gly Glu Arg Lys Arg Ala Ala Asp Asn Lys Ser Leu Gly Gln Phe
65                  70                  75                  80

Asn Leu Asp Gly Ile Asn Pro Ala Pro Arg Gly Met Pro Gln Ile Glu
                85                  90                  95

Val Thr Phe Asp Ile Asp Ala Asp Gly Ile Leu His Val Ser Ala Lys
                100                 105                 110

Asp Lys Asn Ser Gly Lys Glu Gln Lys Ile Thr Ile Lys Ala Ser Ser
            115                 120                 125

Gly Leu Asn Glu Asp Glu Ile Gln Lys Met Val Arg Asp Ala Glu Ala
    130                 135                 140

Asn Ala Glu Ala Asp Arg Lys Phe Glu Glu Leu Val Gln Thr Arg Asn
145                 150                 155                 160

Gln Gly Asp His Leu Leu His Ser Thr Arg Lys Gln Val Glu Glu Ala
                165                 170                 175

Gly Asp Lys Leu Pro Ala Asp Asp Lys Thr Ala Ile Glu Ser Ala Leu
                180                 185                 190

Thr Ala Leu Glu Thr Ala Leu Lys Gly Glu Asp Lys Ala Ala Ile Glu
            195                 200                 205

Ala Lys Met Gln Glu Leu Ala Gln Val Ser Gln Lys Leu Met Glu Ile
    210                 215                 220

Ala Gln Gln Gln His Ala
225                 230

<210> SEQ ID NO 6
<211> LENGTH: 238
<212> TYPE: PRT
<213> ORGANISM: Homo sapiens

<400> SEQUENCE: 6

Met His His His His His Glu Asn Val Gln Asp Leu Leu Leu Leu
1               5                   10                  15

Asp Val Ala Pro Leu Ser Leu Gly Leu Glu Thr Ala Gly Gly Val Met
                20                  25                  30

Thr Ala Leu Ile Lys Arg Asn Ser Thr Ile Pro Thr Lys Gln Thr Gln
                35                  40                  45

Ile Phe Thr Thr Tyr Ser Asp Asn Gln Pro Gly Val Leu Ile Gln Val
        50                  55                  60

Tyr Glu Gly Glu Arg Ala Met Thr Lys Asp Asn Asn Leu Leu Gly Arg
```

```
                65                  70                  75                  80
            Phe Glu Leu Ser Gly Ile Pro Pro Ala Pro Arg Gly Val Pro Gln Ile
                            85                  90                  95

Glu Val Thr Phe Asp Ile Asp Ala Asn Gly Ile Leu Asn Val Thr Ala
                            100                 105                 110

Thr Asp Lys Ser Thr Gly Lys Ala Asn Lys Ile Thr Ile Thr Asn Asp
                            115                 120                 125

Lys Gly Arg Leu Ser Lys Glu Glu Ile Glu Arg Met Val Gln Glu Ala
                            130                 135                 140

Glu Lys Tyr Lys Ala Glu Asp Glu Val Gln Arg Glu Arg Val Ser Ala
            145                 150                 155                 160

Lys Asn Ala Leu Glu Ser Tyr Ala Phe Asn Met Lys Ser Ala Val Glu
                            165                 170                 175

Asp Glu Gly Leu Lys Gly Lys Ile Ser Glu Ala Asp Lys Lys Lys Val
                            180                 185                 190

Leu Asp Lys Cys Gln Glu Val Ile Ser Trp Leu Asp Ala Asn Thr Leu
                            195                 200                 205

Ala Glu Lys Asp Glu Phe Glu His Lys Arg Lys Glu Leu Glu Gln Val
                210                 215                 220

Cys Asn Pro Ile Ile Ser Gly Leu Tyr Gln Gly Ala Gly Gly
            225                 230                 235

<210> SEQ ID NO 7
<211> LENGTH: 7
<212> TYPE: PRT
<213> ORGANISM: Escherichia coli

<400> SEQUENCE: 7

Asn Arg Leu Leu Leu Thr Gly
1               5
```